United States Patent
Ishimaru et al.

(10) Patent No.: US 9,244,345 B1
(45) Date of Patent: Jan. 26, 2016

(54) NON-IONIC PHOTO-ACID GENERATING POLYMERS FOR RESIST APPLICATIONS

(71) Applicants: International Business Machines Corporation, Armonk, NY (US); Central Glass Co., Ltd., Ube-shi, Yamaguchi (JP)

(72) Inventors: Takehisa Ishimaru, San Jose, CA (US); Satoru Narizuka, San Jose, CA (US); Daniel P. Sanders, San Jose, CA (US); Ratnam Sooriyakumaran, San Jose, CA (US); Hoa D. Truong, Los Altos, CA (US); Rudy J. Wojtecki, San Jose, CA (US); Manabu Yasumoto, Kawagoe (JP)

(73) Assignees: International Business Machines Corporation, Armonk, NY (US); Central Glass Co., LTD., Ube-Shi, Yamaguchi (JP)

( * ) Notice: Subject to any disclaimer, the term of this patent is extended or adjusted under 35 U.S.C. 154(b) by 0 days.

(21) Appl. No.: 14/534,824

(22) Filed: Nov. 6, 2014

(51) Int. Cl.
G03F 7/004 (2006.01)
G03F 7/039 (2006.01)
G03F 7/30 (2006.01)
G03F 7/20 (2006.01)
G03F 7/32 (2006.01)
C07D 221/14 (2006.01)
C08F 220/52 (2006.01)
C08F 220/70 (2006.01)
G03F 7/38 (2006.01)
C07C 309/65 (2006.01)
C07C 309/73 (2006.01)
C08F 226/06 (2006.01)

(52) U.S. Cl.
CPC ............ *G03F 7/0045* (2013.01); *C07C 309/65* (2013.01); *C07C 309/73* (2013.01); *C07D 221/14* (2013.01); *C08F 220/52* (2013.01); *C08F 220/70* (2013.01); *C08F 226/06* (2013.01); *G03F 7/0397* (2013.01); *G03F 7/2041* (2013.01); *G03F 7/30* (2013.01); *G03F 7/322* (2013.01); *G03F 7/325* (2013.01); *G03F 7/38* (2013.01)

(58) Field of Classification Search
None
See application file for complete search history.

(56) References Cited

U.S. PATENT DOCUMENTS

| | | | |
|---|---|---|---|
| 6,136,501 A | 10/2000 | Trefonas, III et al. | |
| 6,965,040 B1 | 11/2005 | Gao et al. | |
| 7,014,980 B2 | 3/2006 | Allen et al. | |
| 7,378,683 B2 | 5/2008 | Endoh et al. | |
| 7,812,105 B2 | 10/2010 | Nagai et al. | |
| 8,057,985 B2 | 11/2011 | Ohashi et al. | |
| 8,329,377 B2 | 12/2012 | Takemoto et al. | |
| 8,680,100 B2 | 3/2014 | Jiang et al. | |
| 2011/0319652 A1 | 12/2011 | Jodry et al. | |
| 2012/0171616 A1 | 7/2012 | Thackeray et al. | |
| 2012/0328985 A1 | 12/2012 | Kato et al. | |
| 2013/0071789 A1 | 3/2013 | Iwashita et al. | |
| 2013/0122427 A1* | 5/2013 | Kataoka et al. | G03F 7/004 430/285.1 |
| 2013/0143159 A1 | 6/2013 | Iwashita et al. | |
| 2013/0260313 A1 | 10/2013 | Allen et al. | |

OTHER PUBLICATIONS

Deruiter, J., Principles of Drug Action 1, Spring 2005, Amides, downloaded from the internet at "www.auburn.edu/~deruija/pda1_amides.pdf" on Sep. 22, 2014.

Fielding et al., "Synthesis and reactions of 4-sulpho-2,3,5,6,-tetrafluorobenzoic acid" Journal of Fluorine Chemistry, 59 (1992), pp. 15-31.

Gronheid, et al., "Resolution—linewidth roughness—sensitivity performance tradeoffs for an extreme ultraviolet polymer bound photo-acid generator resist", J. Micro/Nanolith. MEMS MOEMS 10(1), 013017 (Jan.-Mar. 2011).

Hinsberg, et al., "Effect of Resist Components on Image Spreading During Postexposure Bake of Chemically Amplified Resists", Advances in Resist Technology and Processing XVII, Francis M. Houlihan, Editor, Proceedings of SPIE vol. 3999 (2000), pp. 148-160.

McGeary, et al., "An 'inside-out' approach to suramin analogues", Tetrahedron 65 (2009) 3990-3997; available online Mar. 21, 2009.

Thackeray, j. W., "Materials challenges for sub-20-nm lithography", J. Micro/Nanolith. MEMS MOEMS 10(3), 033009 (Jul.-Sep. 2011).

Xu, et al., "Novel polymeric nonionic photoacid generators and corresponding polymer Langmuir—Blodgett (LB) films for photopatterning", Journal of Photochemistry and Photobiology A: Chemistry 219 (2011) 50-57; Available online Feb. 1, 2011.

Yamamoto, et al., "Study on Dissolution Behavior of Polymer-bound and Polymer-blended Photo-acid Generator (PAG) Resists", Advances in Resist Materials and Processing Technology XXX, edited by Mark H. Somervell, Thomas I. Wallow, Proc. of SPIE vol. 8682, 86821B • © 2013 SPIE.

* cited by examiner

*Primary Examiner* — Sin Lee
(74) *Attorney, Agent, or Firm* — Michael R. Roberts

(57) ABSTRACT

Photo-acid generating vinyl polymerizable monomers (PAG monomers) were prepared comprising sulfonate ester groups of N-hydroxide imides. The photo-acid generating portion of the PAG monomer is linked to a polymerizable portion of the monomer by an amide linking group. Photo-acid generating polymers (PAG polymers) of the PAG monomers show high sensitivity to extreme ultraviolet radiation (13.5 nm) and much less sensitivity to far ultraviolet wavelengths (193 nm, 248 nm). The PAG polymers also exhibit thermal and chemical amplification properties useful for forming high resolution positive tone or negative tone lithographic resist patterns.

37 Claims, 24 Drawing Sheets

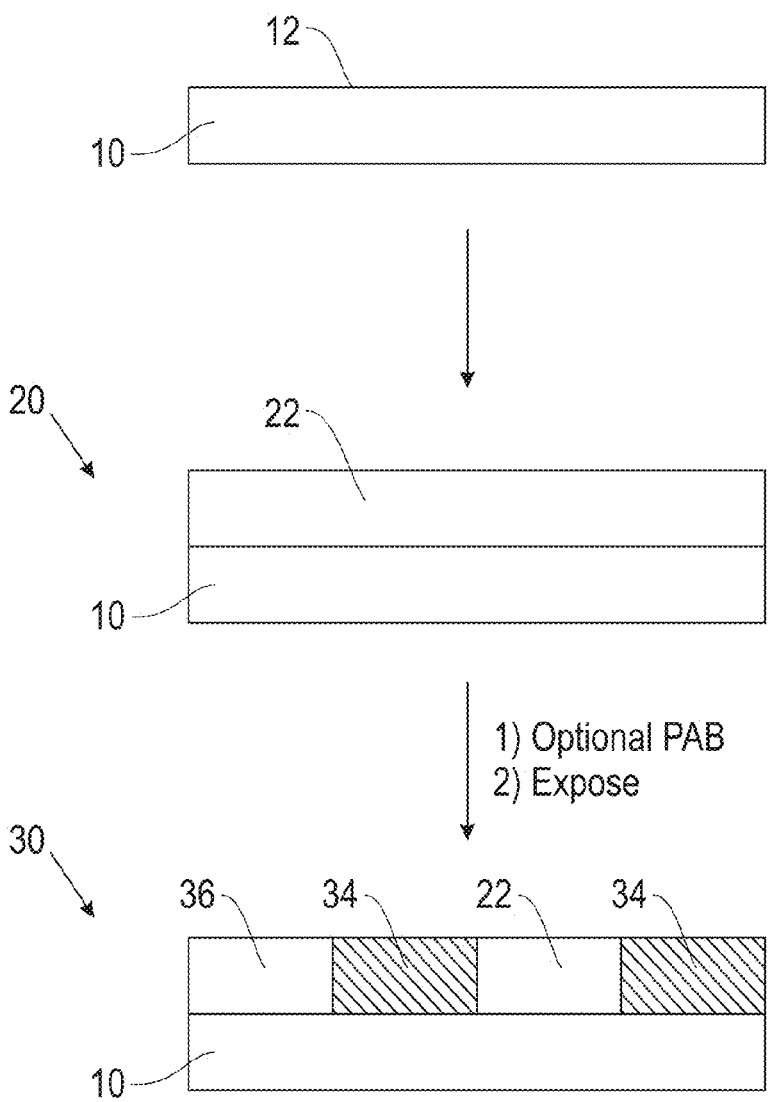

NON-IONIC PHOTO-ACID GENERATING POLYMERS FOR RESIST APPLICATIONS

PARTIES TO A JOINT RESEARCH AGREEMENT

This invention was made under a joint research agreement between International Business Machines Corporation and Central Glass Co., Ltd.

BACKGROUND

The present invention relates to non-ionic photo-acid generating polymers for resist applications, and more specifically, to non-ionic photo-acid generating polymers for extreme ultraviolet lithography bearing pendant sulfonate esters of N-hydroxy imides.

Extreme Ultraviolet (EUV) lithography is expected to succeed current 193 nm immersion lithography combined with multiple exposure enhancements as the next generation printing technique for sub-40 nm features. EUV radiation, with a shorter wavelength of 13.5 nm, is expected to achieve finer features without the need for multiple exposures. However, more advances in more powerful light sources, EUV masks, and resists are needed for commercialization of EUV lithography.

In recent years, considerable effort has gone into the development of resists for EUV applications. However, a majority of EUV resists are modified resists for 193 nm and 248 nm lithography.

The most efficient resists for 193 nm and 248 nm lithography are based on chemical amplification, where an initial relatively low dose of radiation induces formation of a catalyst, often a strong acid. Each molecule of the catalyst induces a relatively large number of chemical events, thereby chemically amplifying the effect of the exposure. For example, chemical amplification of a positive tone resist can involve converting aqueous base insoluble groups of exposed areas to aqueous base soluble groups. In the case of negative tone resists, chemical amplification can involve crosslinking reactions in the exposed areas.

Currently favored positive resist compositions comprise acid-labile groups (e.g., carboxylic esters of tertiary alcohols). Prior to exposure, a layer comprising the resist composition is insoluble in aqueous base developer. During exposure to radiation, a photo-acid generator (PAG), which is present in the layer, produces strong acid. The photogenerated acid catalyzes the deprotection of the acid-labile groups of the exposed portions of the layer during a post exposure bake (PEB). The PEB renders exposed portions of the layer soluble in an aqueous base developer, allowing formation of a positive tone image.

A drawback of resists for 248 nm, 193 nm and E-beam applications is referred to as "image blur" (see, e.g., Hinsberg et al., Proc. SPIE, (2000), 3999, 148). Image blur is generally thought to result from two contributing factors: gradient-driven acid diffusion and reaction propagation, the result being a distortion in the developable image compared to the projected aerial image transferred onto the film. This becomes critical in EUV applications because of the need for very small features with low line edge roughness (LER).

Polymers comprising covalently bound photo-acid generator moieties (i.e., polymer-bound PAGs) were developed to control the gradient-driven acid diffusion. Many current EUV resist compositions now include a polymer-bound PAG, in which the acid functional groups generated during exposure are covalently linked to the polymer.

Many widely reported polymers comprising bound PAG groups for EUV applications are ionic in nature. The PAG moiety comprises a negative charged sulfonate group (*—$SO_3^{-1}$), which is covalently linked to the polymer, and a positive charged counter ion (e.g., triphenylsulfonium, iodonium, diphenyliodonium). U.S. Pat. No. 8,057,985 B2 to Ohashi, et al., discloses examples of polymer-bound ionic PAG groups. These type of polymers have limitations due to low incorporation of PAG bound repeating units (<5 mol %), higher polydispersity, and poorer solubility in casting solvents. These limitations prevent further improvements in resolution and LER using PAG-bound polymers.

A limited number of non-ionic PAG-bound polymers have been reported (U.S. Pat. No. 7,812,105 B2, U.S. Pat. No. 8,329,377 B2, US20120328985 A1). However, the thermal stability of these polymers and the ability to achieve high resolution (sub-40 nm) lithographic performance of formulations comprising these polymers have not been reported.

Another issue that affects the performance of the current EUV resists is their sensitivity to out-of-band radiation (150-400 nm) that is emitted by the light source along with the desired 13.5 nm radiation. The sensitivity of these resists to out-of-band (OOB) radiation is due to the fact that the resists were modified from 193 nm and 248 nm resists that have onium salt PAGs. The effect of OOB radiation is exemplified by the resist thickness loss that results in profile degradation.

Therefore, there is a need to develop high resolution EUV resists that are less sensitive to OOB radiation and provide improved LER.

SUMMARY

Accordingly, a compound is disclosed of formula (1):

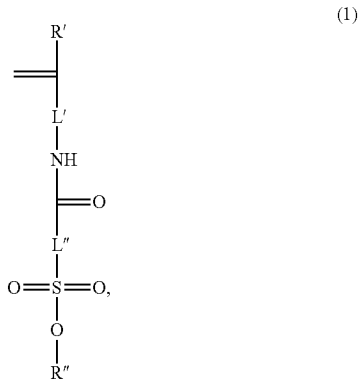

wherein

R' is a monovalent radical selected from the group consisting of H, F, $C_1$-$C_3$ alkyl groups, fluorine-containing $C_1$-$C_3$ alkyl groups, and cyano, L' and L" are independently divalent radicals comprising 1 to 10 carbons, a carbon of L" is linked to the carbonyl,

*—$SO_3$—R" represents a sulfonate ester of an N-hydroxy imide, the compound is capable of polymerization, and the compound is capable of generating an acid upon exposure to radiation.

Also disclosed is a photo-acid generating polymer (PAG polymer), comprising a non-ionic first repeating unit of formula (11):

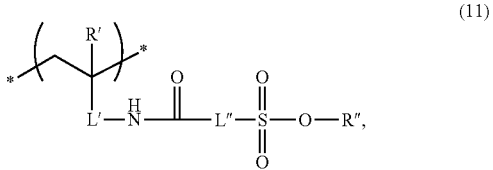

(11)

wherein

R' is a monovalent radical selected from the group consisting of H, F, $C_1$-$C_3$ alkyl, fluorine-containing $C_1$-$C_3$ alkyl groups, and cyano, L' and L" are independently divalent radicals comprising 1 to 10 carbons, a carbon of L" is linked to the carbonyl,

*—$SO_3$—R" represents a sulfonate ester of an N-hydroxy imide, and the first repeating unit is capable of generating an acid upon exposure to radiation.

Further disclosed is a resist composition, comprising:
an above-described PAG polymer; and
an organic solvent, wherein the PAG polymer is dissolved in the organic solvent, and the resist composition is suitable for forming a resist patterns in a lithographic process.

Also disclosed is a method, comprising:
providing a layered structure comprising a resist layer disposed on a surface of a substrate, the resist layer comprising the PAG polymer of claim 10;
pattern-wise exposing the resist layer to radiation, thereby forming an exposed resist layer;
baking the exposed resist layer at about 90° C. to about 130° C. for at least 1 second, thereby forming a treated resist layer; and
selectively removing a region of the treated resist layer using a developer, thereby forming a patterned resist layer.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIGS. 1A to 1E are schematic layer diagrams showing a method of forming a multi-layered structure that includes a topographical patterned layer comprising exposed resist composition.

DETAILED DESCRIPTION

Figure 1D:
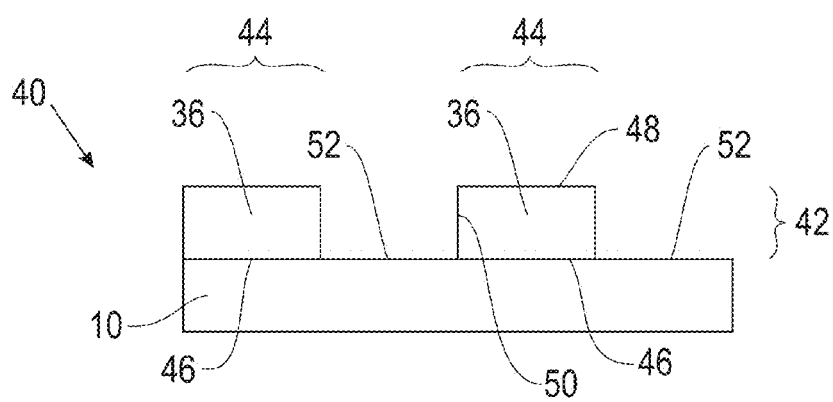

Disclosed herein are non-ionic photo-acid generators (PAGs) in the form of vinyl polymerizable compounds (PAG monomers) and polymers therefrom (PAG polymers). Also disclosed are resist compositions comprising the non-ionic PAG polymers and lithographic methods of forming resist patterns therefrom. Hereinafter, it should be understood that the PAG polymers and PAG monomers are non-ionic prior to a lithographic exposure unless otherwise stated.

The PAG monomers and PAG polymers are capable of forming an acid when exposed to radiation of wavelength between 0 nm and 300 nm, including electron beam (E-beam), extreme ultraviolet radiation (EUV, herein ultraviolet wavelengths of about 4 nm to about 124 nm), soft x-ray, x-ray, γ-ray, and/or deep ultraviolet radiation (DUV, herein ultraviolet wavelengths of 125 nm to 250 nm such as, for example, ArF excimer laser at 193 nm and KrF excimer laser at 248 nm). Preferably, the PAG monomers and PAG polymers are relatively insensitive to DUV compared to EUV. As a result, EUV exposures of resists layers comprising the PAG polymers can produce lithographic patterns having fewer defects associated with out of band (OOB) radiation. In an embodiment, the lithographic process utilizes an ultraviolet wavelength of 13.5 nm (EUV) to expose a resist film comprising the PAG polymer.

The PAG polymers are generally thermally stable up to at least 130° C. In an embodiment, the PAG polymers are thermally stable up to at least 160° C.

The PAG polymers can be used singularly or in combination to form a resist composition. A resist composition can comprise a PAG polymer as the sole photo-acid generating material.

The term "positive-tone development" means the exposed areas of the resist layer are selectively removed during development by a given developer. The exposed areas can become more soluble in a given developer (e.g., aqueous alkaline developer) by, for example, a non-crosslinking chemical reaction induced by the exposure that increases the polarity of the exposed areas.

The term "negative-tone development" means the non-exposed areas of the resist layer are selectively removed during development. In this instance, the exposed areas of the resist layer can become less soluble in a given developer (e.g., organic solvent developers) compared to the non-exposed areas by, for example, a crosslinking reaction or some other chemical change induced by the exposure that lowers the solubility of the exposed areas in the developer.

The term "positive-tone resist pattern" refers to the resist layer containing non-exposed resist that remains after positive-tone development. The examples further below illustrate formation of positive-tone resist patterns using the PAG polymers.

The term "negative-tone resist pattern" refers to the resist layer containing exposed resist that remains after negative tone development.

The PAG polymers can be used to form a positive-tone resist pattern or a negative tone resist patterned.

PAG Monomers

The PAG monomers comprise a divalent amide group that links a polymerizable group to a photo-acid generating group. The photo-acid generating group comprises a sulfonate ester of an N-hydroxy imide. The PAG monomer structure is represented by formula (1):

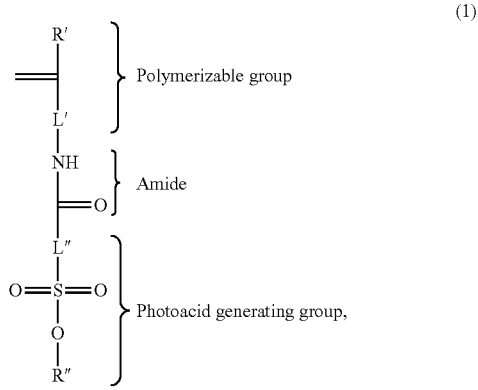

wherein

R' is a monovalent radical selected from the group consisting of H, F, $C_1$-$C_3$ alkyl groups, fluorine-containing $C_1$-$C_3$ alkyl groups, and cyano, L' and L" are independently divalent radicals comprising 1 to 10 carbons, a carbon of L" is linked to the carbonyl, and

*—$SO_3$—R" represents a sulfonate ester of an N-hydroxy imide.

The amide nitrogen of formula (1) is linked to an alkylene carbon (e.g., methylene group), an alkyl substituted alkylene carbon, or an aromatic ring carbon of L'.

The amide carbonyl carbon is linked to an alkylene carbon (e.g., methylene group), an alkyl substituted alkylene carbon, a monofluoromethylene group (*—C(F)(H)—*), a difluoromethylene group (*—$CF_2$—*), or an aromatic ring carbon of L".

The PAG monomer is capable of a polymerization, more specifically a radical polymerization. The PAG monomer is also capable of generating an acid upon exposure to E-beam, EUV radiation, x-ray radiation, and/or ArF and KrF excimer laser.

More specific L' groups have a structure according to formula (2):

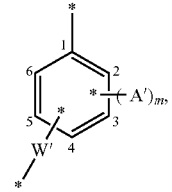

wherein m is an integer having a value of 0 to 4, and each A' when present is an independent monovalent radical having 0 to 2 carbons, W' is a single bond or a divalent radical selected from the group consisting of alkylene groups comprising 1 to 4 carbons and fluorinated alkylene groups comprising 1 to 4 carbons, and W' is linked to the amide nitrogen of formula (1).

Herein, starred bonds represent attachment points and should not be confused with methyl groups. For clarity, the non-starred bond crossing the bond joining carbons 4 and 5 above indicates the bond can be linked to any one of carbons 2 to 6 (i.e., ortho, meta, or para to the starred bond of carbon 1). This convention is used in other structures below. Each A', when present, can be linked to one of the remaining ring carbons not already linked to an A'. Any remaining ring carbon that is not linked to an A' is linked to a hydrogen.

More specific monovalent A' groups include fluorine, bromine, chlorine, methyl, ethyl, trifluoromethyl, methoxy, ethoxy, and acetoxy. Two A' groups can complete a ring such as, for example, a fused 4-membered ring (e.g., cyclobutene).

More specific divalent W' groups include methylene (*—$CH_2$—*), monofluoromethylene (*—C(H)(F)—*), difluoromethylene (*—$CF_2$—*), 1,2-ethylene (*—$CH_2CH_2$-*), 1,1-difluoro-1,2-ethylene (*—$CH_2CF_2$—*), perfluoro-1,2-ethylene (*—$CF_2CF_2$—*), 1,3-propylene (*—$CH_2CH_2CH_2$—*), 1,2-propylene (*—$CH_2C(H)(CH_3)$—*), 1,4-butylene (*—$CH_2CH_2CH_2CH_2$—*), and 1,3-butylene (*—$CH_2CH_2C(H)(CH_3)$—*).

Other more specific L' groups have a structure according to formula (3):

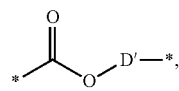
(3)

wherein the carbonyl starred bond is linked to the vinyl group of formula (1),

D' is a divalent radical comprising 2 to 9 carbons, and

D' is linked to the amide nitrogen of formula (1).

More specific divalent D' groups include 1,2-ethylene (*—CH$_2$CH$_2$—*), 1,3-propylene (*—CH$_2$CH$_2$CH$_2$—*), 1,2-propylene (*—CH$_2$C(H)(CH$_3$)—*), 1,4-butylene (*—CH$_2$(CH$_2$)$_2$CH$_2$—*), and 1,3-butylene (*—CH$_2$CH$_2$C(H)(CH$_3$)—*), 1,5-pentylene (*—CH$_2$(CH$_2$)$_3$CH$_2$—*), 1,6-hexylene (*—CH$_2$(CH$_2$)$_4$CH$_2$—*), 1,7-heptylene (*—CH$_2$(CH$_2$)$_5$CH$_2$—*), 1,8-octylene (*—CH$_2$(CH$_2$)$_6$CH$_2$—*), 1,9-nonylene (*—CH$_2$(CH$_2$)$_7$CH$_2$—*), and any of the foregoing groups in which one or more hydrogens are replaced by fluorine, chlorine, and/or bromine.

Other more specific divalent D' groups include the following groups:

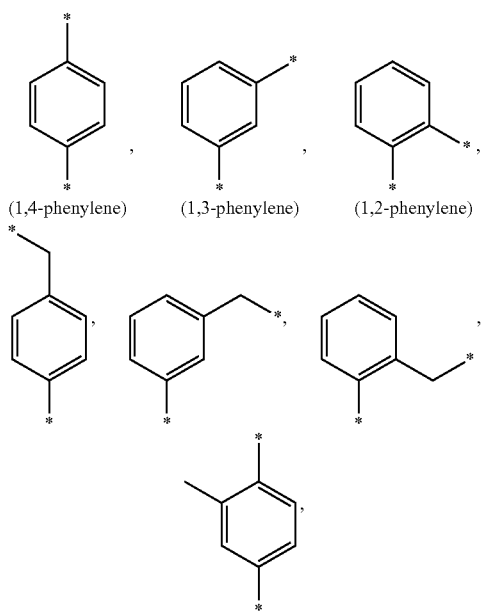

and any of the foregoing groups in which one or more hydrogens are replaced by fluorine. Either one of the starred bonds in the foregoing groups can be linked to the ester oxygen of formula (3).

In an embodiment, D' is 1,2-ethylene (*—CH$_2$CH$_2$—*).

Non-limiting examples of L' groups are shown in Scheme 1. Either one of the starred bonds of the L' groups of Scheme 1 can be linked to the vinyl group of formula (1). In an embodiment, the starred bond of carbon 1 is linked to the vinyl group of formula (1).

Scheme 1.

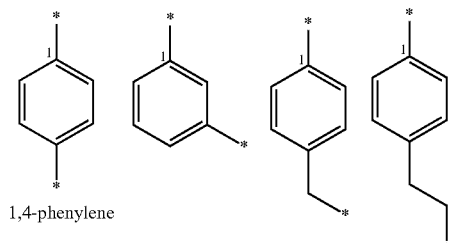
1,4-phenylene

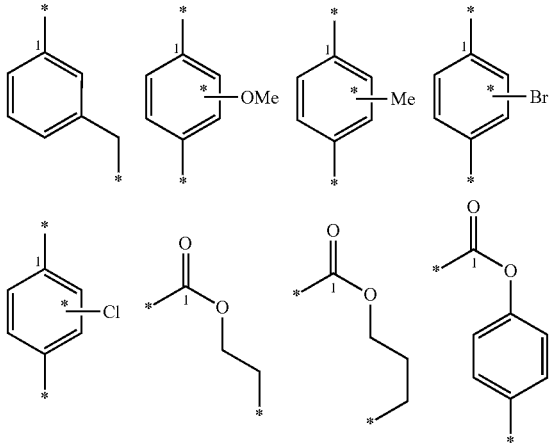

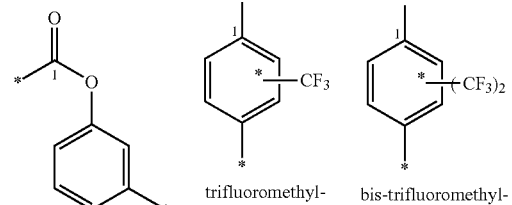
trifluoromethyl-   bis-trifluoromethyl-
1,4-phenylene      1,4-phenylene

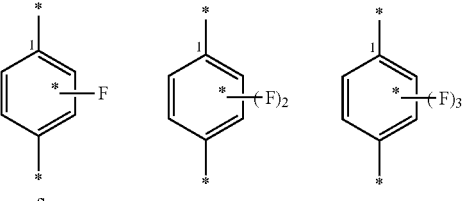
fluoro-    difluoro-    trifluoro-
1,4-phenylene 1,4-phenylene 1,4-phenylene

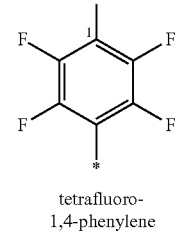
tetrafluoro-
1,4-phenylene

Non-limiting L" groups include divalent alkylene groups, arylene groups, alkylarylene groups, arylalkylene groups, and any of the foregoing groups substituted with one or more fluorine groups.

More specific L" groups include those of Scheme 2 below. Either one of the starred bonds of the L" groups of Scheme 2 can be linked to the amide carbonyl of formula (1). The remaining starred bond is linked to the sulfonate sulfur of formula (1). In an embodiment, the starred bond of carbon 1 is linked to the amide carbonyl of formula (1).

Scheme 2.

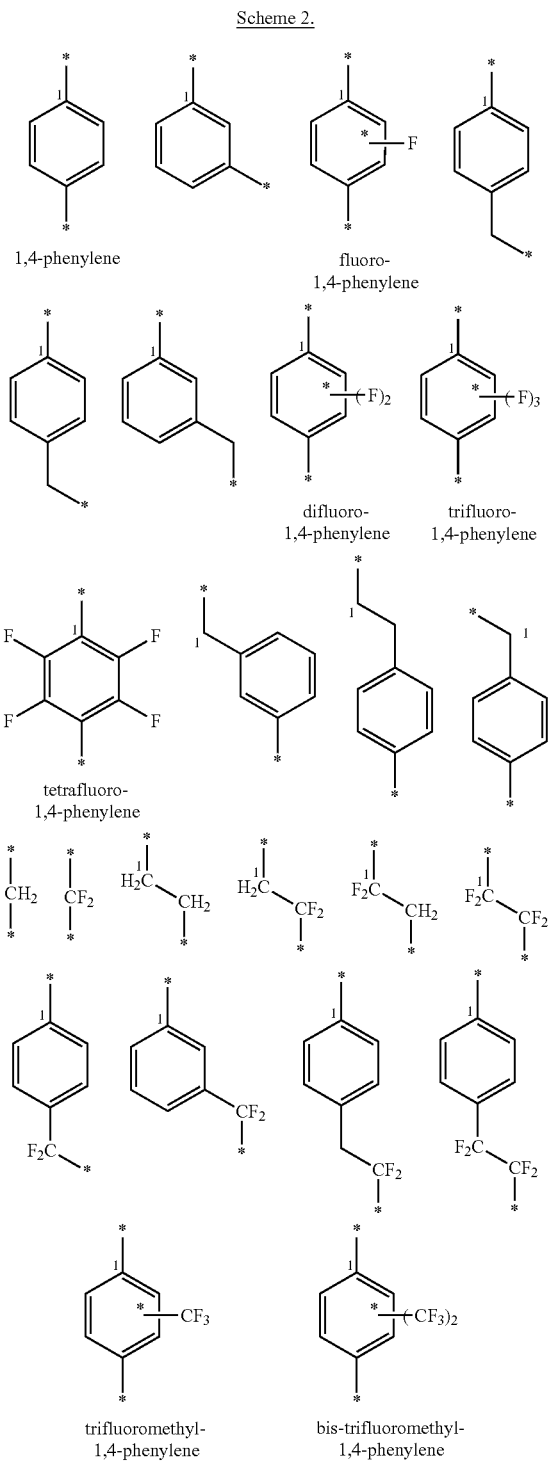

1,4-phenylene fluoro-1,4-phenylene difluoro-1,4-phenylene trifluoro-1,4-phenylene tetrafluoro-1,4-phenylene trifluoromethyl-1,4-phenylene bis-trifluoromethyl-1,4-phenylene More specific L" groups include methylene, difluoromethylene (*—CF$_2$—*), 1,4-phenylene (*—C$_6$H$_4$—*), fluoro-1,4-phenylene (*—C$_6$H$_3$F—*), difluoro-1,4-phenylene (*—C$_6$H$_2$F$_2$-*), trifluoro-1,4-phenylene (*—C$_6$HF$_3$—*), tetrafluoro-1,4-phenylene (*—C$_6$F$_4$—*), trifluoromethyl-1,4-phenylene (*—C$_6$H$_3$(CF$_3$)—*), and bis-trifluoromethyl-1, 4-phenylene (*—C$_6$H$_2$(CF$_3$)$_2$—*), and positional isomers with respect to the fluorine and trifluoromethyl groups of any of the foregoing groups.

The monovalent R" groups of formula (1) have a structure according to formula (4):

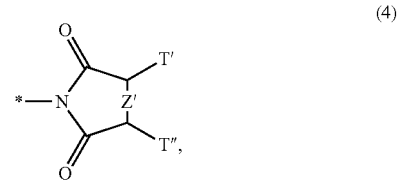

(4)

wherein the nitrogen starred bond is linked to the sulfonate oxygen of formula (1), Z' represents a single bond, a double bond, a methylene group, an aromatic carbon atom, or an oxygen atom, T' is hydrogen or a group comprising 1 to 10 carbons, and T" is hydrogen or a group comprising 1 to 10 carbons.

Optionally, T' and T" together form an aliphatic ring structure, an aromatic ring structure, or a heterocyclic structure that includes Z' and the carbon atoms to which T' and T" are bonded.

Exemplary non-limiting T' and/or T" groups include methyl, ethyl, n-propyl, i-propyl, n-butyl, t-butyl, n-pentyl, n-hexyl, n-heptyl, n-octyl, n-nonyl and n-decyl.

Non-limiting examples of R" groups comprising aliphatic ring structures, aromatic ring structures, and heterocyclic structures formed by T' and T" that include Z' of formula (4) are shown in Scheme 3. The starred bond of each structure of Scheme 3 is linked to the sulfonate oxygen of formula (1).

Scheme 3.

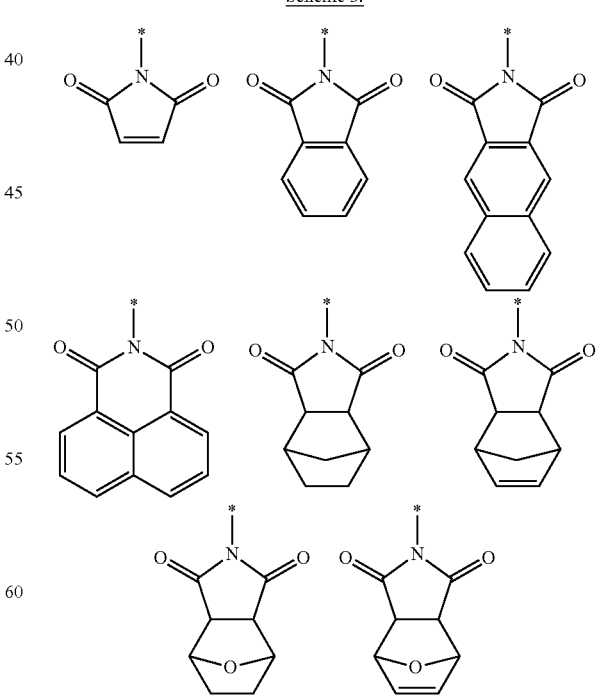

Non-limiting exemplary PAG monomers include those of Scheme 4.

Scheme 4.
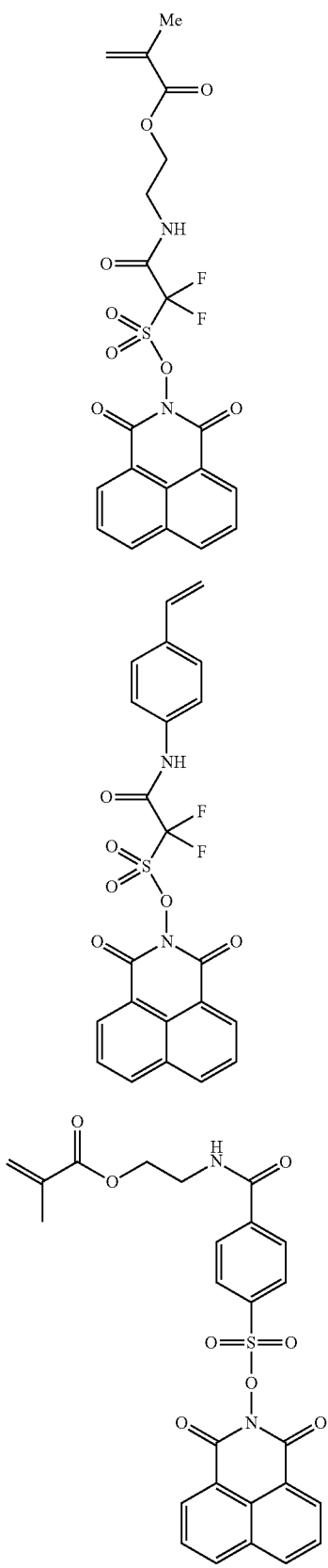
PAG-1
PAG-2
PAG-3
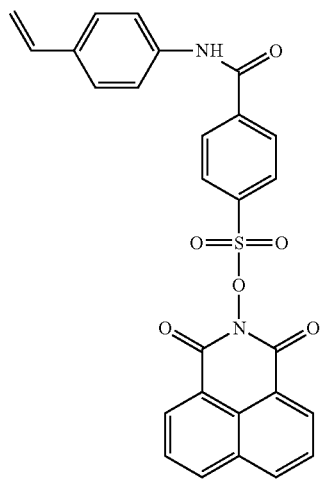
PAG-4
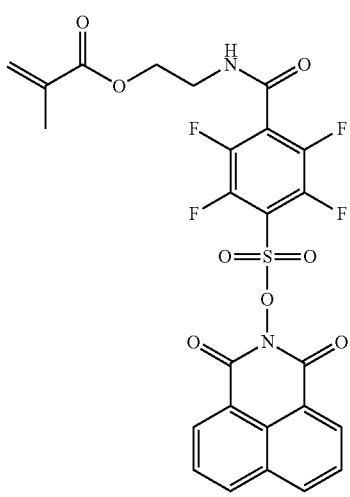
PAG-5
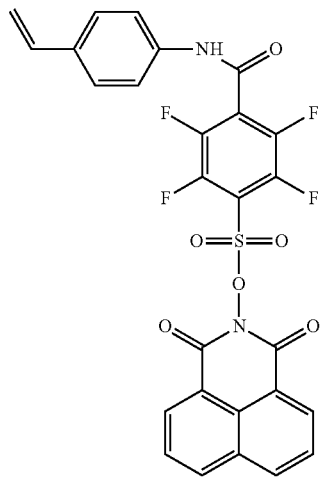
PAG-6
The PAG monomers can be prepared according to the reaction sequences of Scheme 5 below using compounds of formulas (5), (6), (7), and (8).

Scheme 5.

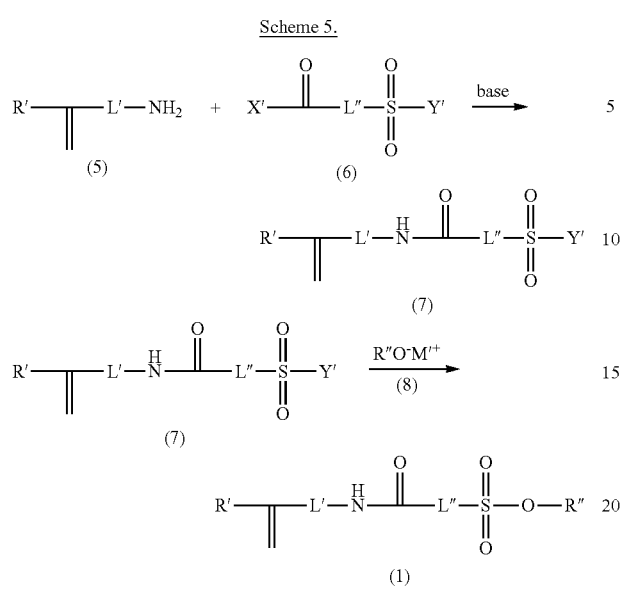

R', R", L', and L" of Scheme 5 have the same meanings discussed further above under formula (1). X' of formula (6) and Y' of formulas (6) and (7) are independently fluoride, chloride, or bromide. The compound of formula (5) represents a vinyl polymerizable monomer comprising a non-protonated primary amine group, herein also referred to as "amine monomer". The compound of formula (6) is referred to herein as a "bis-acid halide". The compound of formula (8), R"O⁻M'⁺, is a salt of an N-hydroxy imide compound (R"OH) wherein M'⁺ is a positive charged counterion (e.g., Li⁺, Na⁺, K⁺, Rb⁺, Cs⁺).

In a first step, a reaction mixture is formed comprising an organic solvent, a base (e.g., pyridine and triethylamine), an amine monomer of formula (5), and a bis-acid halide compound of formula (6). It has been found that under suitable conditions demonstrated by the examples below that the amine monomer can preferentially react at the carboxylic acid halide site of the bis-acid halide, thereby forming the intermediate amide sulfonyl halide compound of formula (7). This reaction is preferably conducted at a temperature of about 0° C.

In a second step, a second reaction mixture is formed comprising an organic solvent, the amide sulfonyl halide compound of formula (7), and a salt of an N-hydroxy imide (R"O⁻M'⁺). The sulfonyl halide compound of formula (7) and the salt of an N-hydroxy imide (R"O⁻M'⁺) react to form the PAG monomer of formula (1). The reaction is preferably performed at a temperature of about 0° C. to about 30° C.

In this manner a PAG monomer can be prepared in two steps using a commercially available polymerizable amine monomer having a primary amine or secondary amine group.

Non-limiting exemplary solvents for the above reactions include dichloromethane, chloroform, toluene, diethyl ether, carbon tetrachloride, 1,2-dichloroethane, tetrachloroethylene, chlorobenzene, dimethylformamide and acetonitrile. The solvents can be used singularly or in combination.

Exemplary vinyl polymerizable amine monomers of formula (5) include 2-aminoethyl methacrylate, 3-aminopropyl methacrylate, 2-aminoethyl acrylate, 3-aminopropylacrylate, 2-aminostyrene, 3-aminostyrene, and 4-aminostyrene. These base monomers can be prepared from the corresponding protonated ammonium salts of the monomers (e.g., hydrochloride salt of the monomer) by treating the ammonium salt beforehand or in situ with a suitable base (e.g., pyridine, triethylamine).

The salt of the N-hydroxy imide (R"O⁻M'⁺) can be prepared from an N-hydroxy imide R"—OH and a suitable base (e.g., potassium tert-butoxide (t-BuO⁻K⁺) using known methods (e.g., Gao, et al., U.S. Pat. No. 6,965,040 B1, Example XIII).

Exemplary bis-acid halides of formula (6) include the compounds of Scheme 6.

Scheme 6.

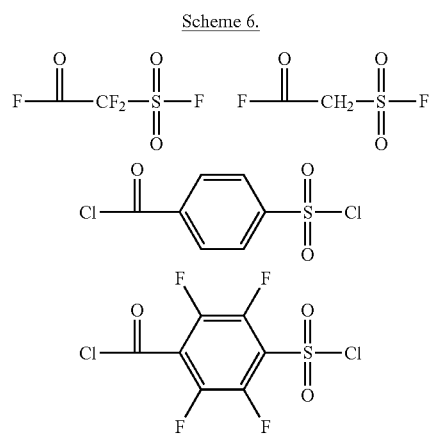

Non-limiting exemplary N-hydroxy imide compounds of formula R"OH include those of Scheme 7.

Scheme 7.

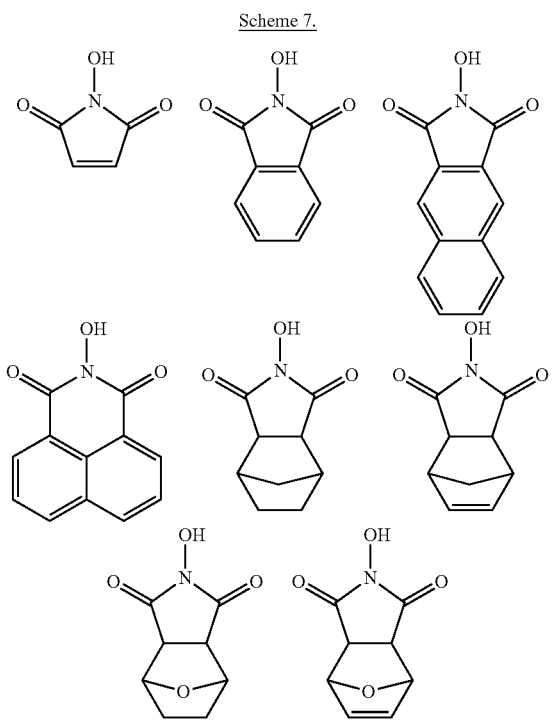

In an embodiment R"O⁻M'⁺ is a compound of formula (9) and/or formula (10), wherein M'⁺ is a positive charged counterion (e.g., Li⁺, Na⁺, K⁺, Rb⁺, Cs⁺).

(9)

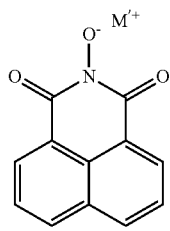

(10)

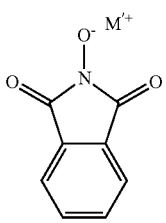

PAG Polymers

First Repeating Unit

The PAG polymers comprise a non-ionic first repeating unit of formula (11):

(11)

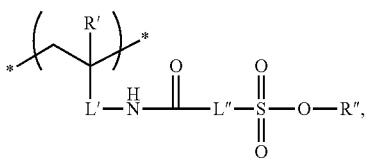

wherein R', L', L", and R" have the meaning discussed above under formula (1).

The PAG polymer comprises the PAG repeating unit in an amount of more than 0 mol %, and up to 100 mol %, based on total moles of monomers used to prepare the PAG polymer. When the PAG polymer functions as a photo-acid generator and a resin for chemical amplification, discussed in more detail below, the PAG polymer preferably comprises the PAG repeating unit in an amount of about 1 mol % to about 20 mol %, more preferably 5 mol % to 15 mol %, based on total moles of repeating units of the PAG polymer.

The PAG polymer can have a number average molecular weight (Mn) of about 100 to about 1,000,000, more particularly 1,000 to about 100,000, and even more particularly 2,000 to about 20,000, as measured by gel permeation chromatography (GPC). The PAG polymer molecular weight is also discussed in more detail below.

Upon exposure to radiation (e.g., E-beam, EUV, x-ray), the first repeating unit of formula (11) of the PAG polymer is converted to a repeating unit bearing a sulfonic acid group (also referred to herein as the "photo-acid repeating unit") of formula (12):

(12)

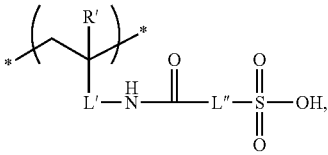

wherein R', L', and L" have the meaning discussed above for formula (1). The sulfonic acid group is a strong acid capable of catalyzing a reaction (e.g., deprotection of an acid-labile group) suitable for chemical amplification in a lithographic patterning process.

Depending on the purpose of use of the PAG polymer, the PAG polymer can comprise the first repeating unit of formula (11) in combination with or without a second repeating unit containing an acid-labile group or a cross-linking site. In either instance, the PAG polymer can have any other repeating unit (referred to herein as an "auxiliary repeating unit"). The term "auxiliary repeating unit" means a repeating unit that does not correspond to the first repeating unit of the formula (11) and does not correspond to the second repeating unit containing an acid-labile group or cross-linking site. The term "auxiliary monomer" means a vinyl polymerizable monomer capable of forming an auxiliary repeating unit. In an embodiment, the second repeating unit comprises an acid labile group, wherein the acid labile group comprises a protected acid group capable of being deprotected by an acid.

The first repeating units can be present singularly or in combination with other first repeating units. The second repeating units can be present singularly or in combination with other second repeating units. The auxiliary repeating units can be present singularly or in combination with other auxiliary repeating units.

Thus, the presence of the second repeating units and the auxiliary repeating units in the PAG polymer is optional. As an example, the PAG polymer can be a homopolymer of the first repeating unit of formula (11) as obtained by homopolymerization of the polymerizable PAG monomer of formula (1). Alternatively, the PAG polymer can be a copolymer consisting essentially of auxiliary repeating units in addition to the first repeating unit of formula (11). In these instances, the PAG polymer cannot function as a positive resist resin capable of chemical amplification, but can function as a photo-acid generator in a resist composition comprising a second polymer resin that comprises acid-labile groups capable of chemical amplification. For such use, the PAG polymer can contain 0.1 to 100 mol %, preferably 1 to 100 mol %, more preferably 2 to 100 mol %, of the first repeating unit of formula (11), the balance being one or more auxiliary repeating units. Herein, mol % of a given repeating unit is based on total moles of all repeating units of the given polymer. If the amount of the first repeating unit of formula (11) is less than 0.1 mol % of the PAG polymer, a second photo-acid generator can be employed in the resist composition in order for the resist composition to maintain sufficient photosensitivity to high energy radiation.

Alternatively, the PAG polymer can consist essentially of the first repeating unit of formula (11) and the second repeating unit containing the acid-labile group or cross-linking site. In this instance, the PAG polymer can have properties suitable for photo-acid generation and chemical amplification in a lithographic process. The PAG polymer can comprise 0.1 mol % to 90 mol %, preferably 0.5 mol % to 50 mol %, more preferably 1 to 20 mol % of the first repeating unit of the general formula (11), the balance being the second repeating unit containing the acid-labile group or cross-linking site. If the amount of the first repeating unit of formula (11) is less than 0.1 mol % of the PAG polymer, a second photo-acid generator can be employed in the resist composition in order for the resist composition to maintain sufficient photosensitivity to high energy radiation.

If the amount of the first repeating unit of formula (11) exceeds 90 mol % of the PAG polymer, the PAG polymer can adequately function as a photo-acid generator. However, little or no benefit with respect to chemical amplification is provided by the PAG polymer comprising less than 10 mol % of the second repeating unit containing the acid-labile group or cross-linking site.

In the case where the PAG polymer comprises the first repeating unit of the general formula (11), the second repeating unit containing the acid-labile group or cross-linking site, and the auxiliary repeating unit, the PAG polymer preferably contains 0.1 mol % to 70 mol %, more preferably 1 mol % to 60 mol %, and most preferably 10 mol % to 50 mol % of the auxiliary repeating unit, and 0.1 mol % to 15 mol % of the first repeating unit of formula (11), the balance being the second repeating unit containing the acid-labile group or cross-linking site.

Substrate adhesion and etching resistance of the PAG polymer are generally adversely affected when the amount of the auxiliary repeating unit is less than 0.1 mol % of the PAG polymer. Moreover, the photo-acid generating properties of the PAG polymer and the utility of the PAG polymer as a positive or negative resist (i.e., the capability of the PAG polymer to undergo chemical amplification) are generally adversely affected when the amount of the auxiliary repeating unit exceeds 70 mol %.

When the PAG polymer functions as the photo-acid generator and a positive or negative resist resin capable of chemical amplification, the PAG polymers preferably contain 1 mol % to 15 mol % of a first repeating unit of formula (11) and 10 mol % to 85 mol % of a second repeating unit containing the acid-labile group or cross-linking site, with the balance being the auxiliary repeating unit. More preferably, the PAG polymers contain 1 mol % to 15 mol % of the first repeating unit of formula (11) and 2 mol % to 40% of the second repeating unit containing the acid-labile group or cross-linking site, with the balance being the auxiliary repeating unit. Most preferably, the PAG polymers contain 4 mol % to 10 mol % of the first repeating unit of formula (11) and 15 mol % to 60 mol % of the second repeating unit containing the acid-labile group or cross-linking site, with the balance being the auxiliary repeating unit. The composition of the PAG polymer is not however limited to the above-described ranges.

When the PAG polymer functions as both the photo-acid generating component and the base resin capable of chemical amplification, the PAG polymer can have a number average molecular weight (Mn) of 1,000 to 1,000,000, more particularly 2,000 to 500,000, even more particularly 5,000 to about 15,000, as measured by gel permeation chromatography (GPC).

When the resist composition is prepared with a PAG polymer and a separate base resin, the PAG polymer can have a number average molecular weight (Mn) of 1,000 to 100,000, preferably 2,000 to 50,000. If the number average molecular weight of the PAG polymer is less than 1,000, the PAG polymer can diffuse and migrate into unexposed portions of the resist film during heat treatment after pattern-wise exposure, causing deterioration in pattern resolution. Solubility of the PAG polymer in a given solvent and/or formation of uniform resist films can be adversely affected when the number average molecular weight of the PAG polymer exceeds 1,000,000.

The molecular weight distribution (Mw/Mn, or polydispersity index (PDI)) of the PAG polymer is preferably in the range of 1.01 to about 2.5, more preferably 1.01 to about 1.75.

When the second repeating unit contains an acid-labile group comprising a protected acid group capable of being deprotected by an acid, the PAG polymer can have dual properties of photo-acid generation and chemical amplification suitable for a positive resist composition. That is, upon exposure, the PAG polymer generates an acid that during a subsequent heat treatment catalyzes the thermal cleavage of the acid-labile groups to form additional acid groups in regions of the exposed PAG polymer, thereby altering (i.e., increasing) the solubility of the exposed PAG polymer relative to non-exposed PAG polymer in a given aqueous base developer).

When the second repeating unit contains a cross-linking site, the PAG polymer can have dual properties of photo-acid generation and chemical amplification suitable for a negative resist composition. That is, upon exposure, the PAG polymer generates an acid that during a subsequent heat treatment catalyzes a cross-linking reaction at a cross-linking site of the PAG polymer (e.g., alcohol group, carboxylic acid group), thereby altering (i.e., decreasing) the solubility of the exposed PAG polymer relative to non-exposed PAG polymer in a given aqueous base developer.

Dry etching resistance, standard developer compatibility, substrate adhesion, resist profile and other resist characteristics such as resolution, heat resistance and sensitivity can be controlled by the types and amounts of second repeat units and auxiliary repeat units used in combination with the first repeat units of formula (11).

Second Repeating Unit Bearing an Acid-Labile Group

The second repeating units containing an acid-labile group can have a structure in accordance with formula (13):

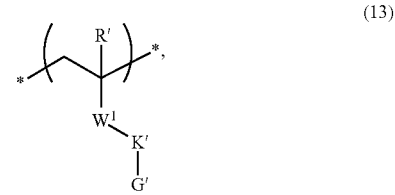

wherein

R' is a monovalent radical selected from the group consisting of H, F, $C_1$-$C_3$ alkyl groups, fluorine-containing $C_1$-$C_3$ alkyl groups, and cyano, $W^1$ is a divalent linking group selected from the group consisting of single bond and groups comprising 1 or more carbons.

K' represents a leaving moiety *—O—* or *—(C=O)—*, and

G' is an acid-labile group.

Other acid-labile second repeating units can have a structure in accordance with formula (14):

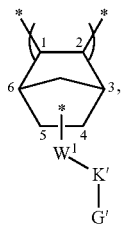
(14)

wherein $W^1$ is a divalent linking group selected from the group consisting of single bond and groups comprising 1 or more carbons, K' represents a leaving moiety *—O—* or *—C(=O)—O—*, and G' is an acid-decomposable group.

*—K'-G' represents an acid-labile group. The acid-decomposable group G' refers to a group capable of being removed from the second repeat unit when heated in the presence of the photo-generated acid, thereby generating an acid in the residue of the leaving moiety K'. The acid-labile group *—K'-G' preferably is i) an ester moiety *—(C=O)OG' (alkoxycarbonyl group) or ii) an ether moiety *—O-G' (alkoxy group).

The second repeating units that contain a crosslinking site can have a structure in accordance with formula (15):

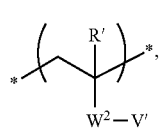
(15)

wherein

R' is a monovalent radical selected from the group consisting of H, F, $C_1$-$C_3$ alkyl groups, fluorine-containing $C_1$-$C_3$ alkyl groups, and cyano, $W^2$ is a divalent linking group selected from the group consisting of single bond and groups comprising 1 or more carbons, and V' is *—O—H or *—(C=O)—OH.

Other second repeating units containing a cross-linking site can have a structure in accordance with formula (16):

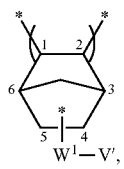
(16)

wherein $W^2$ is a divalent linking group selected from the group consisting of single bond and groups comprising 1 or more carbons, and V' is *—O—H or *—(C=O)—OH.

The hydroxyl group of V' of formulas (15) and (16) refers to a substantially neutral alcoholic hydroxyl group that is not generally involved in the dissolution of the resin into an alkaline solution but is cross-linked with a cross-linking agent by a hydroxyl-related reaction (e.g., ester bonding, ether bonding, ureide bonding, etc.) so as to make the alkali-soluble resin component insoluble in an aqueous alkali solution.

Linking Groups $W^1$ and $W^2$ $W^1$ is a divalent linking group formed by one functional group, or two or more functional groups in combination, selected from the group consisting of a single bond, *—$(CR^{13}R^{14})_n$—* where n is an integer of 1 to 10, *—O—*, *—C(=O)—*, *—C(=O)—O—* or *—O—C(=O)—*, a divalent alicyclic hydrocarbon group, a divalent aromatic hydrocarbon group, a divalent heterocyclic group, a thioether group, an ester group, an amide group, a sulfonamide group, a urethane group, and a urea group.

As non-limiting examples, $W^1$ can have any of the following formulas (17) to (22):

(17)

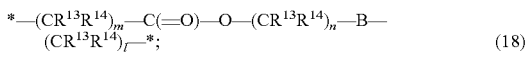
(18)

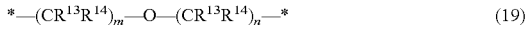
(19)

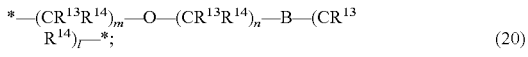
(20)

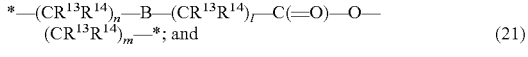
(21)

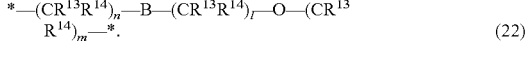
(22)

wherein B represents a cyclic group selected from a divalent alicyclic hydrocarbon group, a divalent aromatic hydrocarbon group, or a divalent heterocyclic group; and l, m and n each independently represent an integer of 0 to 10. It is preferable that m is 0 and each of l and n is 0 or 1. The group *—$(CR^{13}R^{14})$—* is explained further below.

The linking group $W^2$, for linking the "leaving moiety" V' to the main chain of the repeating unit in the negative resist resin, is the same as the linking group $W^1$ except $W^2$ does not include any divalent aromatic hydrocarbon group or aromatic heterocyclic group.

As non-limiting examples, $W^2$ can have any of the following formulas (23) to (28):

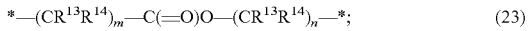
(23)

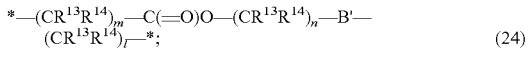
(24)

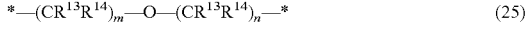
(25)

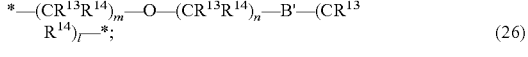
(26)

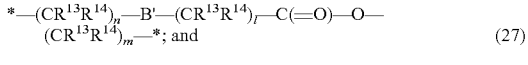
(27)

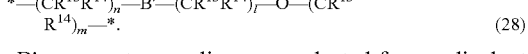
(28)

where B' represents a cyclic group selected from a divalent alicyclic group or a divalent heterocyclic group; and l, m and n each independently represent an integer of 0 to 10. It is preferable that m is 0 and each of l and n is 0 or 1.

No particular limitation is placed on monovalent groups $R^{13}$ and $R^{14}$ in the substituted or unsubstituted methylene group represented by *—$(CR^{13}R^{14})$—*. $R^{13}$ and $R^{14}$ each independently represent a hydrogen atom, a halogen atom, a hydroxy group, or a monovalent $C_1$-$C_{30}$ group selected from the group consisting of substituted or unsubstituted alkyl groups, substituted or unsubstituted aliphatic hydrocarbon groups, alkoxy groups, substituted or unsubstituted aryl groups, and substituted or unsubstituted condensed polycyclic aromatic groups. Each of these monovalent groups can contain a fluorine atom, an oxygen atom, a sulfur atom, a nitrogen atom or a carbon-carbon double bond. Moreover, $R^{13}$ and $R^{14}$ can be the same or different and can together form a ring structure, preferably an alicyclic hydrocarbon structure, with another atom in the second repeat unit. $R^{13}$ and/or $R^{14}$ are exemplified as follows.

$R^{13}$ and/or $R^{14}$ can be an acyclic alkyl group of 1 to 30 carbon atoms, preferably 1 to 12 carbon atoms. Examples of the acyclic alkyl groups include methyl, ethyl, n-propyl, i-propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Lower alkyl groups are preferred. Particularly preferred are methyl, ethyl, n-propyl and i-propyl. Herein, the term "lower" means that the group to which the term is attached has 1 to 4 carbon atoms and, in the case where the group is cyclic, has 3 to 7 carbon atoms.

$R^{13}$ and/or $R^{14}$ can be an acyclic substituted alkyl group obtained by substitution of one hydrogen atom or two or more hydrogen atoms of an above-described alkyl group with a $C_1$-$C_4$ alkoxy group, a halogen atom, an acyl group, an acyloxy group, a cyano group, a hydroxy group, a carboxy group, an alkoxycarbonyl group, or a nitro group, and is preferably a fluorine-substituted alkyl group (i.e., fluoroalkyl group). Examples of acyclic substituted alkyl groups $R^{13}$ and/or $R^{14}$ are lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoropropyl.

$R^{13}$ and/or $R^{14}$ can be an alicyclic hydrocarbon group or an alicyclic hydrocarbon group formed by $R^{13}$ and $R^{14}$ together. The alicyclic hydrocarbon group can be monocyclic or polycyclic. Examples of the alicyclic hydrocarbon groups are those having a monocyclo, bicyclo, tricyclo, or tetracyclo structure of 3 or more carbon atoms, preferably 3 to 30 carbon atoms, more preferably 3 to 25 carbon atoms. The alicyclic hydrocarbon group can have a substituent.

A monocyclic hydrocarbon group $R^{13}$ and/or $R^{14}$ preferably has 3 to 12 ring carbon atoms, more preferably 3 to 7 ring carbon atoms. Examples of such a monocyclic hydrocarbon group a include cyclopropyl, cyclobutyl, cyclopentyl, cyclohexyl, cycloheptyl, cyclooctyl, cyclodecanyl, cyclododecanyl, and 4-tert-butylcyclohexyl. A polycyclic hydrocarbon group $R^{13}$ and/or $R^{14}$ preferably has 7 to 15 ring carbon atoms. Examples of such a polycyclic hydrocarbon groups include adamantyl, noradamantyl, decalinyl (monovalent hydrocarbon structure of decalin), tricyclodecanyl, tetracyclododecanyl, norbornyl and cedryl (monovalent hydrocarbon structure of cedrol). The alicyclic hydrocarbon group can be a spiro ring, preferably having 3 to 6 carbon atoms. Examples of spiro ring are adamantyl, decalinyl, norbornyl, cedryl, cyclohexyl, cycloheptyl, cyclooctyl, cyclodecanyl, cyclododecanyl and tricyclodecanyl. One or more hydrogen atoms on the ring carbons of the above organic groups, or one or more hydrogen atoms of the above linking group, can be each independently substituted with a substituent such as $C_1$-$C_{30}$ alkyl or substituted alkyl group, hydroxy group, alkoxy group, carboxyl group, and/or alkoxycarbonyl group. One or more hydrogen atoms of the substituent can further be substituted with fluorine or trifluoromethyl.

Herein, each of $C_1$-$C_{30}$ alkyl groups $R^{13}$ and/or $R^{14}$ is preferably a lower alkyl group, more preferably an alkyl group selected from the group consisting of methyl, ethyl, propyl and isopropyl. As the substituent of the substituted alkyl group, there can be used a hydroxy group, a halogen atom, an alkoxy group, alkoxy carbonyl group, and the like. The alkoxy group preferably has 1 to 4 carbon atoms, as exemplified by methoxy, ethoxy, propoxy and butoxy. Exemplary alkoxy carbonyl groups include methoxycarbonyl, ethoxycarbonyl and isopropoxycarbonyl.

Aryl groups $R^{13}$ and/or $R^{14}$ can be substituted or unsubstituted and have 1 to 30 carbon atoms. It is preferable that, when the aryl group is monocyclic, the monocyclic aryl group has 3 to 12 ring carbon atoms, more preferably 3 to 6 ring carbon atoms. Examples of aryl groups $R^{13}$ and/or $R^{14}$ include phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

Examples of $C_1$-$C_{30}$ condensed polycyclic aromatic groups are monovalent organic groups obtained by elimination of one hydrogen atom from pentalene, indene, naphthalene, azulene, heptalene, biphenylene, indacene, acenaphthylene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like. In each of the foregoing groups, one or more hydrogen atom can be substituted with a fluorine atom or a $C_1$-$C_4$ alkyl or fluorine-containing alkyl group.

Examples of the monocyclic and polycyclic heterocyclic groups are those of 3 to 25 ring carbon atoms, such as pyridyl, furyl, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One or more hydrogen atoms on the ring structure of the above heterocyclic group can each be independently substituted with an alkyl group, an alicyclic hydrocarbon group, an aryl group, or a heterocyclic group. Preferred are those having a monocyclic or polycyclic ether ring or lactone ring, exemplified by the following formulas (29-A) to (29-E):

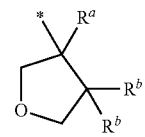

(29-A)

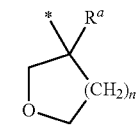

(29-B)

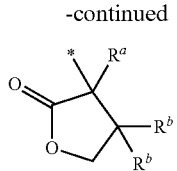
(29-C)

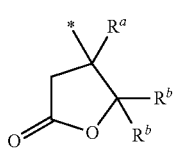
(29-D)

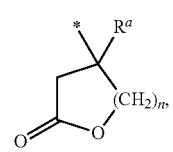
(29-E)

wherein $R^a$ and $R^b$ each independently represent a hydrogen atom or a $C_1$-$C_4$ alkyl group, and n represents an integer of 2 to 4.

The divalent alicyclic hydrocarbon group, constituting the main skeleton of the linking group $W^1$ and/or $W^2$, can be either monocyclic or polycyclic. More specifically, the divalent alicyclic hydrocarbon group can be any of those having a monocyclo, bicyclo, tricyclo, or tetracyclo structure of 3 or more carbon atoms, preferably 3 to 30 carbon atoms, more preferably 3 to 25 carbon atoms. The divalent alicyclic hydrocarbon group can have a substituent.

The divalent alicyclic hydrocarbon group, when it is monocyclic, preferably has 3 to 12 ring carbon atoms, more preferably 3 to 7 ring carbon atoms. Examples of the divalent monocyclic alicyclic hydrocarbon group are cyclopropylene, cyclobutylene, cyclopentylene, cyclohexylene, cycloheptylene, cyclooctylene, cyclodecanylene, cyclododecanylene and 4-tert-butylcyclohexylene. The alicyclic hydrocarbon group, when it is polycyclic, can have, for example, 7 to 15 ring carbon atoms. Examples of the divalent polycyclic alicyclic hydrocarbon group are adamantylene, noradamantylene, decalinylene (divalent hydrocarbon structure of decalin), tricyclodecanylene, tetracyclododecanylene, norbornylene (divalent hydrocarbon structure of norbornane), and cedrylene (divalent hydrocarbon structure of cedrol). The divalent alicyclic hydrocarbon group can be a spiro ring of preferably of 3 to 6 carbon atoms. One hydrogen atom or two or more hydrogen atoms on the linking group or the ring carbon(s) of the organic group can be each independently be substituted with a substituent such as $C_1$-$C_{30}$ alkyl group, substituted alkyl group, hydroxy group, alkoxyl group, carboxyl group, or alkoxycarbonyl group. The $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxy group, a halogen atom, an alkoxyl group and the like. The alkoxyl group is, for example, of 1 to 4 carbon atoms, as exemplified by methoxy, ethoxy, propoxy and butoxy. The alkoxycarbonyl group is, for example, exemplified by methoxycarbonyl, ethoxycarbonyl and isopropoxycarbonyl.

The divalent aromatic hydrocarbon group, when constituting the main skeleton of the linking group $W^1$, can be in the form of a monocyclic or condensed polycyclic aromatic ring structure of 1 to 30 carbon atoms. The aromatic hydrocarbon group, when it is monocyclic, preferably has 3 to 12 ring carbon atoms, more preferably 3 to 6 ring carbon atoms.

Examples of the divalent monocyclic aromatic hydrocarbon group are divalent organic groups obtained by elimination of two hydrogen atoms from benzene, biphenyl, terphenyl, toluene, phenol, anisole, mesitylene, cumene, 2,3-xylylene, 2,4-xylene, 2,5-xylene, 2,6-xylene, 3,4-xylene, 3,5-xylene, fluorobenzene, trifluoromethylbenzene, o-bistrifluoromethylbenzene, m-bistrifluoromethylbenzene, p-bistrifluoromethylbenzene, chlorobenzene, bromobenzene, iodobenzene, and the like.

The divalent condensed polycyclic aromatic group can be substituted or unsubstituted and preferably has 1 to 30 carbon atoms. Examples of the divalent condensed polycyclic aromatic group are divalent organic groups obtained by elimination of two hydrogen atoms from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene, and the like. One hydrogen atom or two or more hydrogen atoms of the above divalent organic group can each be independently substituted with a fluorine atom or a $C_1$-$C_4$ alkyl group or fluorine-containing alkyl group.

The divalent heterocyclic group, constituting the main skeleton of the linking group $W^1$, can be in the form of a monocyclic or polycyclic ring structure of 3 to 25 ring carbon atoms. The ring structure can be aromatic or nonaromatic. Examples of the divalent monocyclic or polycyclic heterocyclic group are divalent organic groups obtained by elimination of two hydrogen atoms from pyridine, furan, thienine, pyranine, pyrroline, thianthrene, pyrazon, isothiazone, isooxazone, pyrazine, pyrimidine, pyridazine, tetrahydropyranine, tetrahydrofuranine, tetrahydrothiopyranine, tetrahydrothiofuranine and the like. One hydrogen atom or two or more hydrogen atoms on the ring atom of the above divalent organic group can each be independently substituted with an alkyl group (preferably, a lower alkyl group), an alicyclic hydrocarbon group, an aryl group or a heterocyclic group. Among others, preferred are monocyclic or polycyclic ether rings as exemplified below.

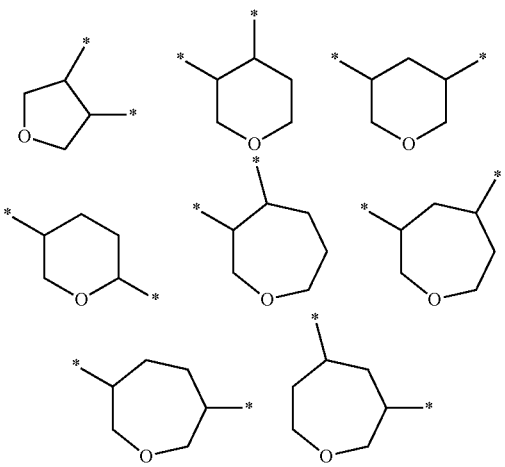

Each of the divalent linking groups $W^1$ and $W^2$ can be formed by combination of any of the divalent groups explained above by the general formulas or specifically exemplified above, with limitations on $W^2$ as stated further above.

Specific examples of the linking group $W^1$ are as follows:

*—* (single bond);

*—$CH_2$—*;

*—$CH_2$—$CH_2$—*;

*—$CH_2$—B—*;

*—B—$CH_2$—*;

*—$C_6H_4$—*;

*—C(=O)—O—$CH_2$—*;

*—C(=O)—O—$CH_2$—$CH_2$—*;

*—C(=O)—O—B—*;

*—$CH_2$—C(=O)—O—$CH_2$—*;

*—O—$CH_2$—*;

*—O—$CH_2$—$CH_2$—*;

*—$CH_2$—O—$CH_2$—*;

*—C(=O)—O—$(C(R^{13})(R^{14}))_2$—*; and

*—$C_6H_4$—O—$(C(R^{13})(R^{14}))_2$—*, wherein B represents a cyclic group selected from a divalent alicyclic hydrocarbon group, a divalent aromatic hydrocarbon group or a divalent heterocyclic group, $R^{13}$ and $R^{14}$ are each independently a hydrogen atom, a fluorine atom, an alkyl group, a substituted alkyl group or an alicyclic hydrocarbon group. One or more hydrogen atoms of the above linking group $W^1$ can be substituted with a fluorine atom. Particularly preferred are *—C(=O)—O—$CH_2$—*, *—$C_6H_4$—* and *—C(=O)—O—$(C(R^{13})(R^{14}))_2$*— wherein $R^{13}$ and $R^{14}$ are each independently a hydrogen atom, a fluorine atom, a lower alkyl group or a fluorine-containing lower alkyl group.

Specific examples of the linking group $W^2$ are as follows:

*—* (single bond);

*—$CH_2$—*;

*—$CH_2$—$CH_2$—*;

*—$CH_2$—B'—*;

*—B'—*

*—B'—$CH_2$—*

*—C(=O)—O—$CH_2$—*;

*—C(=O)—O—$CH_2$—$CH_2$—*;

*—C(=O)—O—B'—*;

*—$CH_2$—C(=O)—O—$CH_2$—*;

*—O—$CH_2$—*;

*—O—B'—*;

*—$CH_2$—O—$CH_2$—*; and

*—C(=O)—O—$(C(R^{13})(R^{14}))_2$—*, wherein B' represents a cyclic group selected from a divalent alicyclic group or a divalent heterocyclic group, $R^{13}$ and $R^{14}$ are each independently a hydrogen atom, a fluorine atom, an alkyl group, a substituted alkyl group, or an alicyclic hydrocarbon group. One or more hydrogen atoms of the above linking group $W^2$ can be substituted with a fluorine atom. Particularly preferred are *—C(=O)—O—*, *—C(=O)—O—$CH_2$—*, *—C(=O)—C)—B'—*, and *—C(=O)—O—$(C(R^{13})(R^{14}))_2$*— wherein $R^{13}$ and $R^{14}$ are each independently a hydrogen atom, a fluorine atom, a lower alkyl group, or a fluorine-containing lower alkyl group.

Other second repeating units comprising an acid-labile group have a structure according to formula (30):

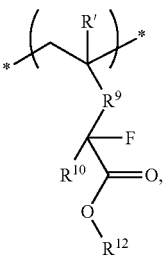
(30)

wherein

R' is a monovalent radical selected from the group consisting of H, F, $C_1$-$C_3$ alkyl groups, fluorine-containing $C_1$-$C_3$ alkyl groups, and cyano, $R^9$ represents a divalent linking group, $R^{10}$ represents a hydrogen atom, a fluorine atom, or a fluorine-containing alkyl group, and $R^{12}$ is an acid-labile group.

As *—$R^9$—$C(R^{10})(F)$—* corresponds to $W^1$, the above definition of the linking group $W^1$ can be applied to the moiety *—$R^9$—$C(R^{10})(F)$—*.

The acid-labile group $R^{12}$ of formula (30) can have a structure in accordance with any of formulas (31) to (35):

$$R^{X1}\text{—O—C(=O)—*} \tag{31}$$

wherein $R^{X1}$ represents a $C_1$-$C_4$ alkyl group that can have a substituent, a $C_3$-$C_{30}$ alicyclic hydrocarbon group that can have a substituent, or a $C_6$-$C_{14}$ aryl group that can have a substituent;

$$R^{X1}\text{—O—C(H)}(R^{X2})\text{—*} \tag{32}$$

wherein $R^{X1}$ has the same definition as in the general formula (31), and $R^{X2}$ represents a hydrogen atom, a $C_1$-$C_4$ alkyl group that can have a substituent, a $C_3$-$C_{30}$ alicyclic hydrocarbon group that can have a substituent, a $C_1$-$C_6$ alkoxy group that can have a substituent, a $C_2$-$C_4$ alkenyl group that can have a substituent, a $C_6$-$C_{14}$ aryl group that can have a substituent, or a $C_7$-$C_{20}$ aralkyl group that can have a substituent;

$$\text{*—C}((R^{X3})(R^{X4})(R^{X5})) \tag{33}$$

wherein $R^{X3}$, $R^{X4}$ and $R^{X5}$ can be the same or different and each represents a $C_1$-$C_4$ alkyl group that can have a substituent, a $C_3$-$C_{30}$ alicyclic hydrocarbon group that can have a substituent, a $C_2$-$C_4$ alkenyl group that can have a substituent, a $C_6$-$C_{14}$ aryl group that can have a substituent, or a $C_7$-$C_{20}$ aralkyl group that can have a substituent; and two of $R^{X3}$, $R^{X4}$ and $R^{X5}$ can be bonded together to form a ring;

$$\text{*—Si}(R^{X3})(R^{X4})(R^{X5}) \tag{34}$$

wherein $R^{X3}$, $R^{X4}$ and $R^{X5}$ have the same definitions as in the general formula (33); and $$R^{X1}\text{—C(=O)—*} \tag{35}$$

wherein $R^{X1}$ has the same definition as in the general formula (31).

The monovalent organic groups $R^{X1}$, $R^{X2}$, $R^{X3}$, $R^{X4}$ and $R^{X5}$ in the above formulas (31) to (35) are described below in more detail. It is herein preferable to use the acid-labile group of the general formula (31), (32) or (33) in the resist composition for pattern formation by exposure to high energy radiation as the acid-labile group of the general formula (31), (32) or (33) has a chemical amplification function.

More specifically, $R^{X1}$ represents an alkyl group, an alicyclic hydrocarbon group or an aryl group; $R^{X2}$ represents a hydrogen atom, an alkyl group, an alicyclic hydrocarbon group, an alkenyl group, an aralkyl group, an alkoxy group or an aryl group; $R^{X3}$, $R^{X4}$ and $R^{X5}$ can be the same or different and each represents an alkyl group, an alicyclic hydrocarbon group, an alkenyl group, an aralkyl group or an aryl group; and two of two of $R^{X3}$, $R^{X4}$ and $R^{X5}$ can be bonded together to form a ring.

Preferred examples of the alkyl groups are those of 1 to 4 carbon atoms, such as methyl, ethyl, propyl, isopropyl, n-butyl, sec-butyl and tert-butyl. Preferred examples of the alicyclic hydrocarbon group are those of 3 to 30 carbon atoms, such as cyclopropyl, cyclopentyl, cyclohexyl, adamantyl, norbornyl, bornyl, tricyclodecanyl, dicyclopentenyl, epoxynorbornan, menthyl, isomenthyl, neomenthyl, tetracyclododecanyl and steroid residue. Preferred examples of the alkenyl group are those of 2 to 4 carbon atoms, such as vinyl, propenyl, allyl and butenyl. Preferred examples of the aryl group are those of 6 to 14 carbon atoms, such as phenyl, xylyl, toluoyl, cumenyl, naphthyl and anthracenyl. These groups can have substituents. Preferred examples of the aralkyl group are those of 7 to 20 carbon atoms, such as benzyl, phenethyl and cumyl, each of which can have a substituent.

As the substituents of the alkyl group, the alicyclic hydrocarbon group, the alkenyl group, the aryl group and the aralkyl group, there can be used: a hydroxy group; a halogen atom (fluorine, chlorine, bromine, iodine); a nitro group; a cyano group; any of the above alkyl and alicyclic hydrocarbon groups; an alkoxy group such as methoxy, ethoxy, hydroxyethoxy, propoxy, hydroxypropoxy, n-butoxy, isobutoxy, sec-butoxy or tert-butoxy; an alkoxycarbonyl group such as methoxycarbonyl or ethoxycarbonyl; an aralkyl group such as benzyl, phenethyl or cumyl; an aralkyloxy group; an acyl group such as formyl, acetyl, butyryl, benzoyl, cinnamyl or valeryl; an acyloxy group such as butyryloxy; any of the above alkenyl groups; an alkenyloxy group such as vinyloxy, propenyloxy, allyloxy or butenyloxy; any of the above aryl groups, an aryloxy group such as phenoxy; and an aryloxycarbonyl group such as benzoyloxy.

There can also be used lactone groups of the following formulas (36) to (44).

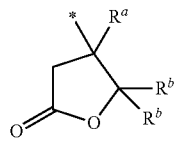
(36)

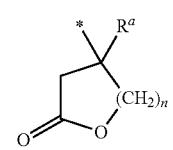
(37)

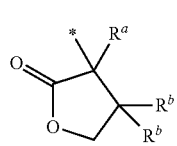
(38)

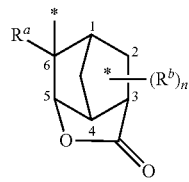
(39)

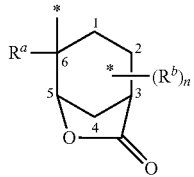
(40)

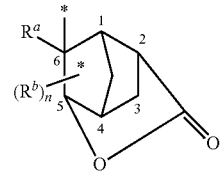
(41)

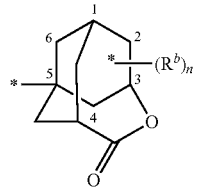
(42)

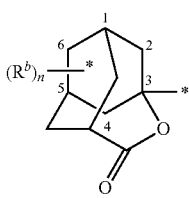
(43)

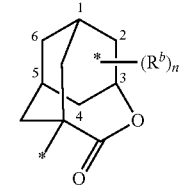
(44)

In the formulas (36) to (44), $R^a$ represents a $C_1$-$C_4$ alkyl or perfluoroalkyl group; $R^b$ each independently represent a hydrogen atom, a $C_1$-$C_4$ alkyl or perfluoroalkyl group, a hydroxy group, a carboxylic acid group, an alkyloxycarbonyl group, an alkoxy group or the like; and n represents an integer of 1 to 4. Each $R^b$ can be linked to any one of the numbered carbons 1 to 6 that does not already have 4 substituents.

More specific acid-labile groups are exemplified as follows.

Specific examples of the alkoxycarbonyl group represented by the general formula (31): $R^{X1}$—O—C(=O)—* are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adarnantanoxycarbonyl.

Specific examples of the acetal group represented by the general formula (32): $R^{X1}$—O—CHR$^{X2}$—* are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyoxyethyl, 1-ethoxyisobutyl, 1-methoxyethoxymethyl, tetrahydropyranyl and tetrahydrofuranyl. There can also be used acetal groups obtained by addition of vinyl ethers to a hydroxy group.

Specific examples of the tertiary hydrocarbon group represented by the general formula (33): *—C($R^{X3}$)($R^{X4}$)($R^{X5}$) are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isobornyl, 1-methyladamantyl, 1-ethyladamantyl, 1-isopropyladamantyl, 1-isopropylnorbornyl and 1-isopropyl-(4-methylcyclohexyl).

Alicyclic hydrocarbon groups or alicyclic hydrocarbon-containing acid-labile group are exemplified by the structures of Scheme 8.

Scheme 8.

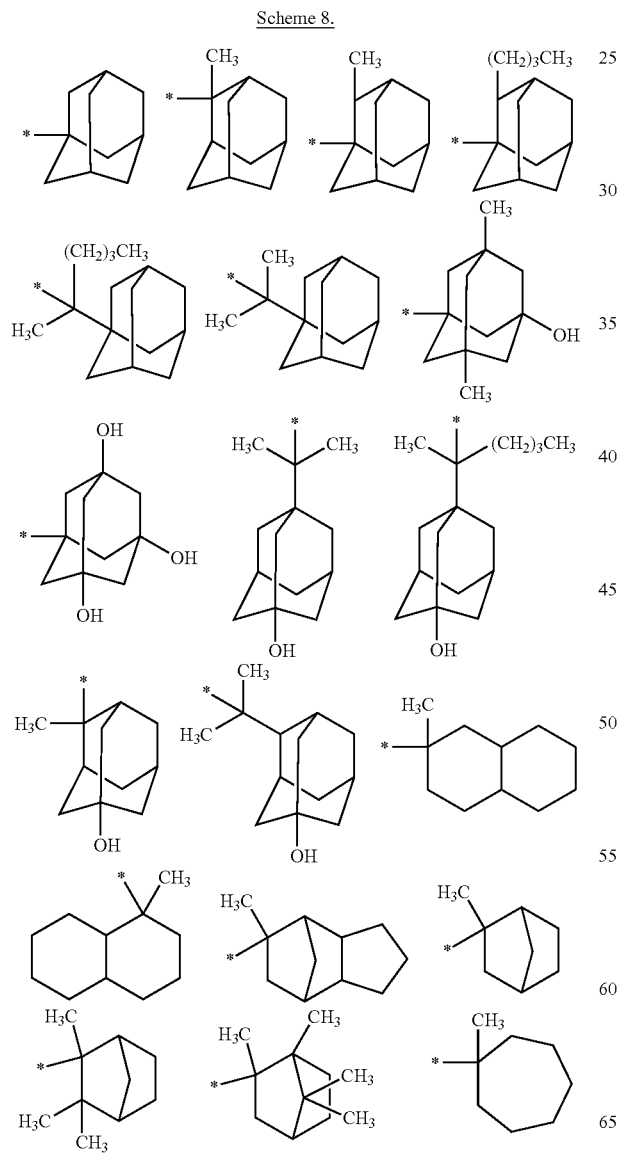

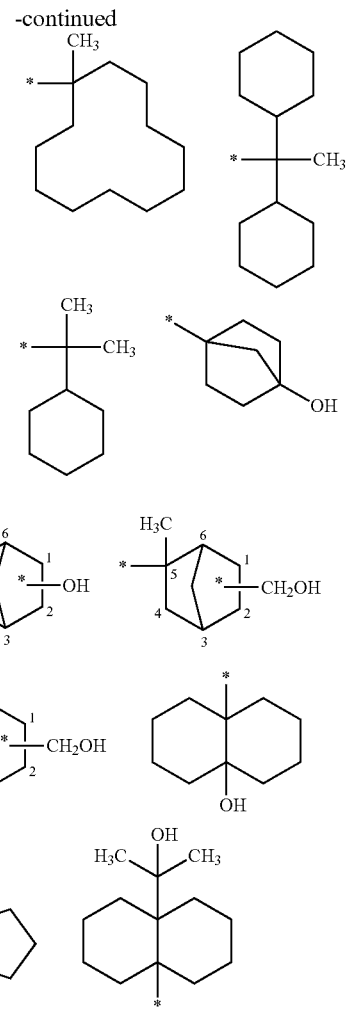

In Scheme 8, the methyl ($CH_3$) groups can independently be replaced by an ethyl group; and one or more of the ring carbons can have a substituent group as mentioned above. The bonds to OH and $CH_2OH$ that overlap a ring bond can be linked to any one of the numbered carbons 1 to 6 that is not already linked to 4 substituents.

Specific examples of the silyl group represented by the general formula (34): *—Si($R^{X3}$)($R^{X4}$)($R^{X5}$) are trimethylsilyl, ethyldimethylsilyl, methyldiethylsilyl, triethylsilyl, i-propyldimethylsilyl, methyl-di-1-propylsilyl, tri-1-propylsilyl, tert-butyldimethylsilyl, methyl-di-tert-butylsilyl, tri-tert-butylsilyl, phenyldimethylsilyl, methyldiphenylsilyl and triphenylsilyl.

Specific examples of the acyl group represented by the general formula (35): $R^{X1}$—C(=O)—* are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophthaloyl, terephthaloyl, naphthoyl, toluoyl, hydroatropoyl, atropoyl, cinnamoyl, furoyl, thenoyl, nicotinoyl and isonicotinoyl. There can also be used those obtained by substitution of a part or all of hydrogen atoms of the above acid-labile groups with a fluorine atom.

Further, the lactone-containing acid-labile protecting group can be exemplified by the groups of Scheme 9.

Scheme 9.
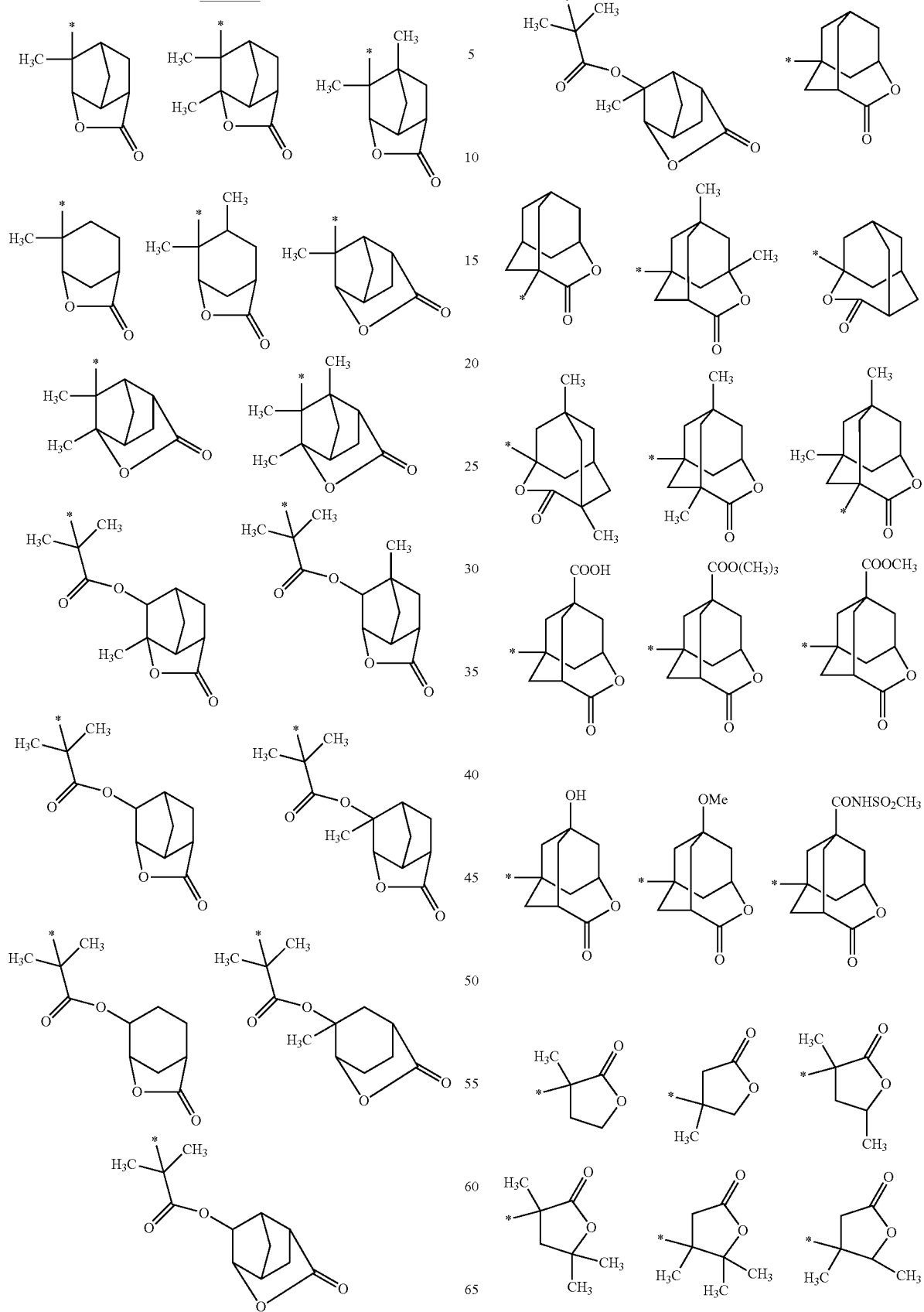

-continued

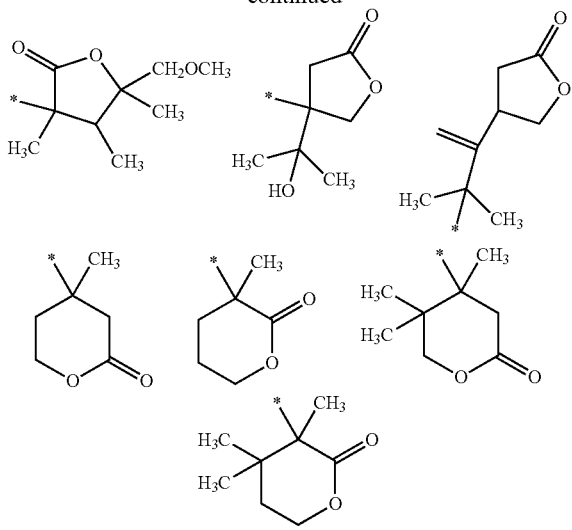

In the structures of Scheme 9, each methyl ($CH_3$) group can independently be replaced by an ethyl group.

Most preferred acid-labile groups include a tertiary alkyl group such as tert-butyl or tert-amyl, an alkoxyethyl group such as 1-ethoxyethyl, 1-butoxyethyl, 1-isobutoxyethyl or 1-cyclohexyloxyethyl, an alkoxymethyl group such as methoxymethyl or ethoxymethyl, an acid-labile group containing an alicyclic hydrocarbon such as adamantyl or isobornyl, or a lactone-containing acid-labile group as exemplified above.

Acid Labile Monomers

Preferred polymerizable monomers for forming the second repeating units containing an acid labile group include those shown in Scheme 10. Each of the "acid labile" monomers can be used singularly or in combination with other acid labile monomers.

Scheme 10.

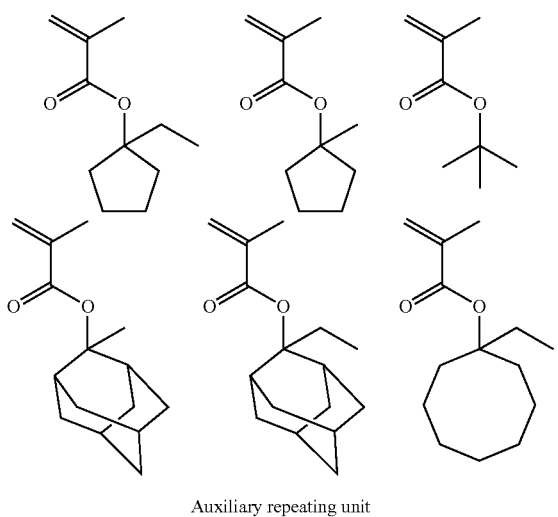

Auxiliary repeating unit

The PAG polymer can be produced with the use of one or more vinyl polymerizable auxiliary monomers as co-monomers. There is no particular limitation on the auxiliary monomer. Non-limiting exemplary auxiliary monomers include olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers. Acrylic esters, methacrylic esters, fluorine-containing acrylic esters, fluorine-containing methacrylic esters, norbornene compounds, fluorine-containing norbornene compounds, styrenic compounds, vinyl ethers and fluorine-containing vinyl ethers are preferred classes of auxiliary monomers. In an embodiment, the auxiliary monomer and the auxiliary repeating unit of the PAG polymer comprise a hexafluoroalcohol (HFA) group (*—$C(CF_3)_2OH$).

Specific examples of the olefins are ethylene and propylene. Specific examples of the fluoroolefins are vinyl fluoride, vinylidene fluoride, trifluoroethylene, chlorotrifluoroethylene, tetrafluoroethylene, hexafluoroethylene and hexafluoroisobutene.

No particular limitation is placed on the ester side chain structure of the acrylic ester and/or methacrylic ester. The term "acrylic and/or methacrylic" is abbreviated herein as "(meth)acrylic". The term "acrylate and/or methacrylate" is abbreviated herein as "(meth)acrylate". Specific examples of (meth)acrylic esters are (meth)acrylic ester compounds having alkyl ester groups (e.g., methyl(meth)acrylate, ethyl (meth)acrylate, n-propyl(meth)acrylate, isopropyl(meth) acrylate, n-butyl(meth)acrylate, isobutyl(meth)acrylate, n-hexyl(meth)acrylate, n-octyl(meth)acrylate, 2-ethylhexyl (meth)acrylate, lauryl(meth)acrylate, 2-hydroxyethyl(meth) acrylate, and 2-hydroxypropyl(meth)acrylate); (meth)acrylates containing an ethylene glycol group, propylene glycol group, or tetramethylene glycol group: unsaturated amides (e.g., acrylamide, methacrylamide, N-methylol acrylamide, N-methylol methacrylamide, and diacetone acrylamide); acrylonitrile; methacrylonitrile; alkoxysilane-containing vinylsilane; alkoxysilane-containing (meth)acrylic ester; t-butyl(meth)acrylate; 3-oxocyclohexyl(meth)acrylate; adamantyl(meth)acrylate; alkyladamantyl(meth)acrylate; cyclohexyl(meth)acrylate; tricyclodecanyl(meth)acrylate; (meth) acrylates having a ring structure such as a lactone ring and/or norbornene ring; acrylic acid; and methacrylic acid.

There can also be used an acrylate compound obtained by bonding a cyano group to the α-position of the above acrylate or analog thereof.

There can also be used maleic acid, fumaric acid and maleic anhydride.

There can also be used (meth)acrylate esters of alicyclic compounds having alcohol functionalities (e.g., hydroxyadamantyl methacrylate)

Examples of fluorine-containing acrylic esters are acrylic esters having a fluorine atom or a fluorine-containing group in the alpha-position of the acrylic acid group. For instance, the monomer having a fluoroalkyl group in its alpha-position can suitably be exemplified by a monomer in which a trifluoromethyl group, a trifluoroethyl group, or a nonafluoro-n-butyl group has been added to the alpha-position of the above non-fluorinated acrylic ester.

On the other hand, there can be used (meth)acrylic esters in which a fluorinated alkyl group (e.g., a perfluoroalkyl group or a fluoroalkyl group) is bonded to the ester moiety or in which a cyclic structure coexists with a fluorine atom in the ester moiety. The cyclic structure can be a fluorine-containing benzene ring, a fluorine-containing cyclopentane ring, a fluorine-containing cyclohexane ring, a fluorine-containing cycloheptane ring, or the like having a fluorine atom or a trifluoromethyl group as a substituent. A (meth)acrylic ester in which the ester moiety is a fluorine-containing t-butyl ester group can also be used. Typical examples of such monomer units include 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, and perfluorocyclohexylmethyl methacrylate.

Norbornene monomers and fluorine-containing norbornene monomers having a mononuclear or multinuclear structure can be used without particular limitation. Examples of norbornene compounds are those each formed by Diels-Alder addition reaction of an unsaturated compound such as an allyl alcohol, a fluorine-containing allyl alcohol, an acrylic acid, an alpha-fluoroacrylic acid, a methacrylic acid and any of the acrylic esters, methacrylic esters, fluorine-containing acrylic esters and fluorine-containing methacrylic esters described herein with cyclopentadiene or cyclohexadiene.

The styrenic compounds, fluorine-containing styrenic compounds, vinyl ethers, fluorine-containing vinyl ethers, allyl ethers, vinyl esters, vinyl silanes, and the like can also be used as auxiliary monomers. Examples of the styrenic compounds and fluorine-containing styrenic compounds include styrene, fluorinated styrene, hydroxystyrene, hexafluoroacetone-added styrenic compounds, trifluoromethyl-substituted styrene, hydroxystyrene, and monomers obtained by bonding a halogen atom, an alkyl group, or a fluoroalkyl group to the alpha-position of the above styrene or fluorine-containing styrenic compounds. Examples of the vinyl ethers and fluorine-containing vinyl ethers include i) alkyl vinyl ethers having an alkyl group (e.g., methyl, ethyl) or a hydroxyalkyl group (e.g., hydroxyethyl, hydroxybutyl) in which a part or all of hydrogen atoms can be substituted with fluorine and ii) cyclic vinyl ethers (e.g., cyclohexyl vinyl ether) including cyclic vinyl ethers containing a hydrogen and/or a carbonyl bond in their cyclic structures, in which a part or all of hydrogen atoms can be substituted with fluorine. The allyl ethers, vinyl esters and vinyl silane can be used without particular limitation.

One preferred example of the auxiliary repeating unit in the PAG polymer or fluorine-containing N-sulfonyloxyimide resin is a repeating unit of the following general formula (45).

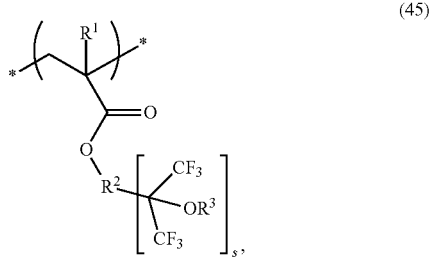

(45)

wherein s represents an integer of 1 to 8, $R^1$ is a monovalent radical selected from the group consisting of hydrogen, halogen, $C_1$-$C_3$ alkyl, fluorine-containing $C_1$-$C_3$ alkyl group, and cyano, $R^2$ represents a substituted or unsubstituted aliphatic hydrocarbon group, a substituted or unsubstituted aromatic group, or a divalent organic group formed by combination of a plurality thereof, and $R^3$ represents a hydrogen atom, a substituted or unsubstituted $C_1$-$C_{25}$ aliphatic hydrocarbon group or a substituted or unsubstituted $C_1$-$C_{25}$ aromatic hydrocarbon group.

Optionally, any number of hydrogen atoms of $R^2$ can be substituted with a fluorine atom. $R^2$ can contain an ether bond and/or a carbonyl group.

Examples of the halogen atom as $R^1$ are fluorine, chlorine and bromine. Examples of the $C_1$-$C_3$ alkyl group as $R^1$ are methyl, ethyl, propyl and isopropyl. Examples of the $C_1$-$C_3$ fluorine-containing alkyl group as $R^1$ are those obtained by substitution of a part or all of hydrogen atoms of the above alkyl groups with a fluorine atom, such as trifluoromethyl (*—$CF_3$), trifluoroethyl (*—$CH_2CF_3$), 1,1,1,3,3,3-hexafluoroisopropyl and heptafluoroisopropyl. Preferred $R^1$ groups include hydrogen, fluorine, methyl and trifluoromethyl.

Any number of hydrogen atoms of $R^2$ can be substituted with a fluorine atom. The divalent aliphatic hydrocarbon group of $R^2$ can be straight, branched or cyclic. Examples of $R^2$ include straight chain and branched aliphatic hydrocarbon groups such as methylene, ethylene, isopropylene and t-butylene; cyclic aliphatic hydrocarbon groups such as cyclobutylene, cyclohexylene, divalent norbornane, and divalent adamantane; aromatic groups such as phenylene; divalent groups obtained by substitution of hydrogen atoms of the above groups with any substituent; and divalent groups obtained by replacement of carbon atoms of the above groups by an ether bond or a carbonyl group. These groups can be used without particular limitation.

More specific auxiliary repeating units include repeating units of formula (46):

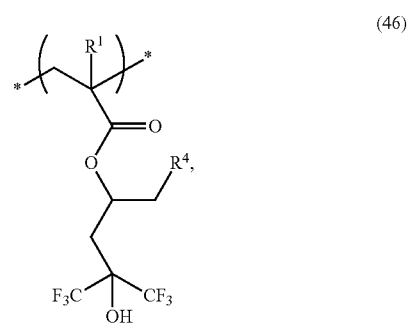

(46)

wherein $R^1$ has the same definition as in the general formula (45), and $R^4$ represents a hydrogen atom or a $C_1$-$C_6$ alkyl or fluorine-containing alkyl group.

Examples of the alkyl or fluorine-containing alkyl group as $R^4$ are methyl, ethyl, n-propyl, isopropyl, n-butyl, sec-butyl, tert-butyl, cyclopentyl, cyclohexyl, fluoromethyl, difluoromethyl, trifluoromethyl and perfluoroethyl.

Other more specific auxiliary repeating units are repeating units of formulas (47):

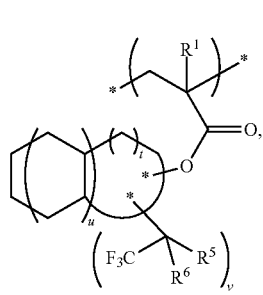

(47)

wherein u represents an integer of 0 to 2, each of t and v independently represents an integer of 1 to 8, wherein $v \leq t+2$, $R^1$ has the same definition as in the general formula (45), $R^5$ represents a methyl group or a trifluoromethyl group, and $R^6$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which can contain a fluorine atom, an oxygen atom (ether bond) or a carbonyl group.

In the case where there are a plurality of $R^5$ and $R^6$ groups and v is an integer of 2 or greater, $R^5$ and $R^6$ can be the same or different. A particularly preferred $R^6$ is hydrogen.

Examples of the substituted or unsubstituted $C_1$-$C_{25}$ aliphatic hydrocarbon group or substituted or unsubstituted $C_1$-$C_{25}$ aromatic hydrocarbon group as $R^6$ include methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, aryl, butenyl, pentenyl, ethynyl, phenyl, benzyl and 4-methoxybenzyl, in each of which a part or all of hydrogen atoms can be substituted with a fluorine atom. As the oxygen-containing hydrocarbon group, an alkoxycarbonyl group, an acetal group or an acyl group can be used. Examples of the alkoxycarbonyl group are tert-butoxycarbonyl, tert-amyloxycarbonyl, methoxycarbonyl, ethoxycarbonyl and i-propoxycarbonyl. Examples of the acetal group are: linear ethers such as methoxymethyl, methoxyethoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl; and cyclic ethers such as tetrahydrofuranyl and tetrahydropyranyl. Examples of acyl groups include acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophthaloyl, terephthaloyl, naphthoyl, toluoyl, hydratropyl, atropoyl, cinnamoyl, furoyl, thenoyl, nicotinoyl and isonicotinoyl. All or part of hydrogen atoms of the above groups can be substituted with fluorine.

Preferred auxiliary repeating units of formulas (46) and (47) are listed in Scheme 11. These auxiliary repeating units can be used singularly or in combination with other auxiliary repeating units.

Scheme 11.

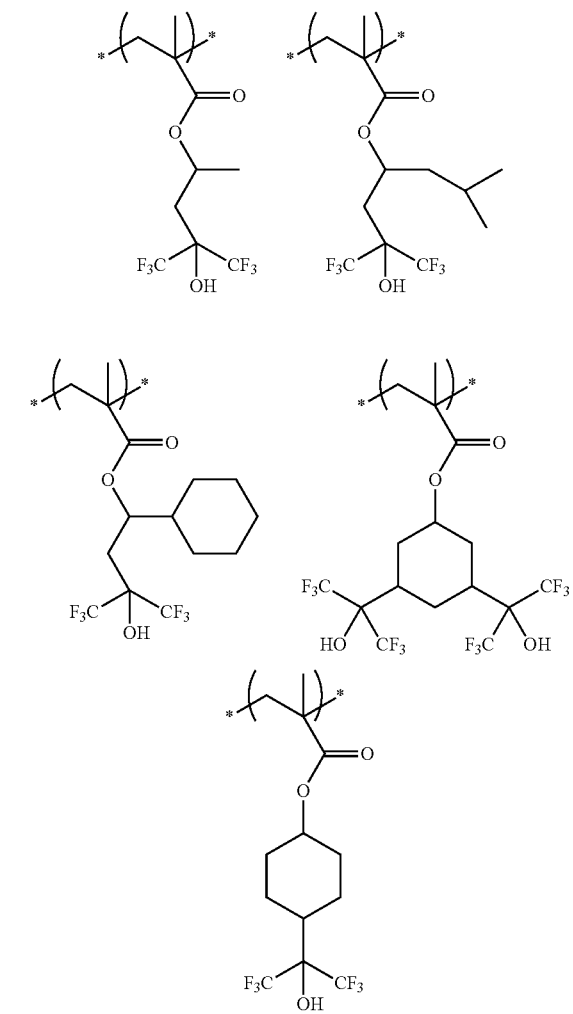

Other preferred auxiliary repeating units of the PAG polymer are those of formula (48):

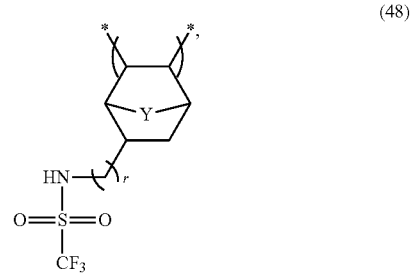

(48)

wherein r represents an integer of 2 to 6, and

Y represents either *—$CH_2$—*, —*O—* or —*S—*.

Particularly preferred examples of the auxiliary repeating units of formula (48) are listed in Scheme 12. These preferred repeating units can be used singularly or in combination with other auxiliary repeating units.

Scheme 12.

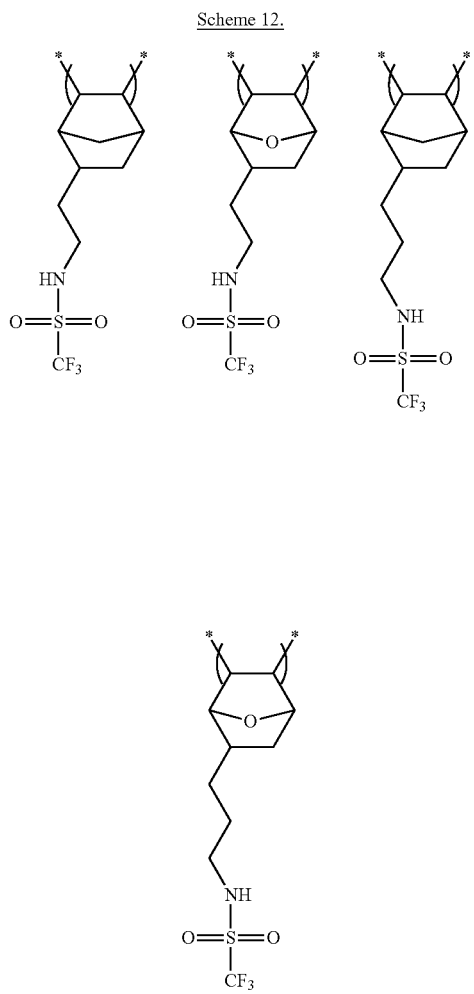

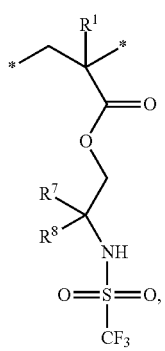

Other preferred examples of auxiliary repeating units include those of formula (49):

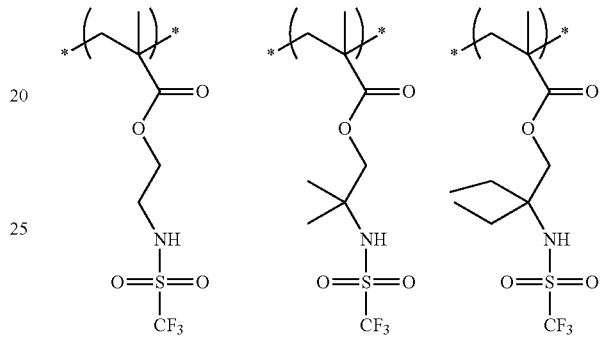

(49)

wherein $R^1$ has the same definition as in the general formula (45), and $R^7$ and $R^8$ each independently represents a member selected from the group consisting of hydrogen atom, substituted or unsubstituted $C_1$-$C_{25}$ straight chain aliphatic hydrocarbon groups, substituted or unsubstituted $C_1$-$C_{25}$ branched chain hydrocarbon groups, cyclic aliphatic hydrocarbon groups, and substituted or unsubstituted aromatic hydrocarbon groups.

Any number of hydrogen atoms of $R^7$ and/or $R^8$ can be substituted with a fluorine atom. $R^7$ and/or $R^8$ can contain an ether bond or a carbonyl group. Exemplary $R^7$ and $R^8$ groups of formula (49) are the same as those of $R^6$ described above for formula (47).

Particularly preferred examples of auxiliary repeating units of formula (49) are listed in Scheme 13. These auxiliary repeating units can be used singularly or in combination with other auxiliary repeating units.

Scheme 13.

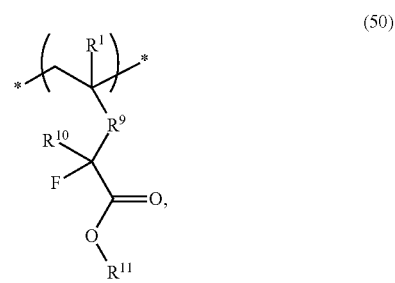

Another preferred examples of auxiliary repeating units include those of formula (50):

$$\text{(50)}$$

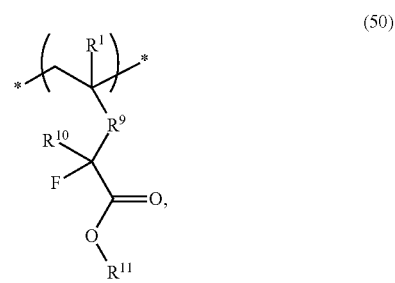

wherein $R^1$ has the same definition as in the general formula (45), $R^{11}$ corresponds in definition to $R^6$ of formula (47), $R^9$ represents a divalent linking group and corresponds in definition to the linking group $W^1$ described further above, and $R^{10}$ represents a hydrogen atom, a fluorine atom, or a fluorine-containing alkyl group.

The fluorine-containing alkyl group of formula (50) can be used without particular limitation. Examples of the fluorine-containing alkyl group are those of 1 to 12 carbon atoms, preferably 1 to 3 carbon atoms, such as trifluoromethyl, pentafluoromethyl, 2,2,2-trifluoroethyl, n-heptafluoropropyl, 2,2,3,33-pentafluoropropyl, 3,3,3-trifluoropropyl and 1,1,1,3,3,3-hexafluoropropyl. As $R^{10}$, a fluorine atom or a trifluoromethyl group is particularly preferred.

Particularly preferred examples of auxiliary repeating units of formula (50) are listed in Scheme 14. These auxiliary repeating units can be used singularly or in combination with other auxiliary repeating units.

Scheme 14.

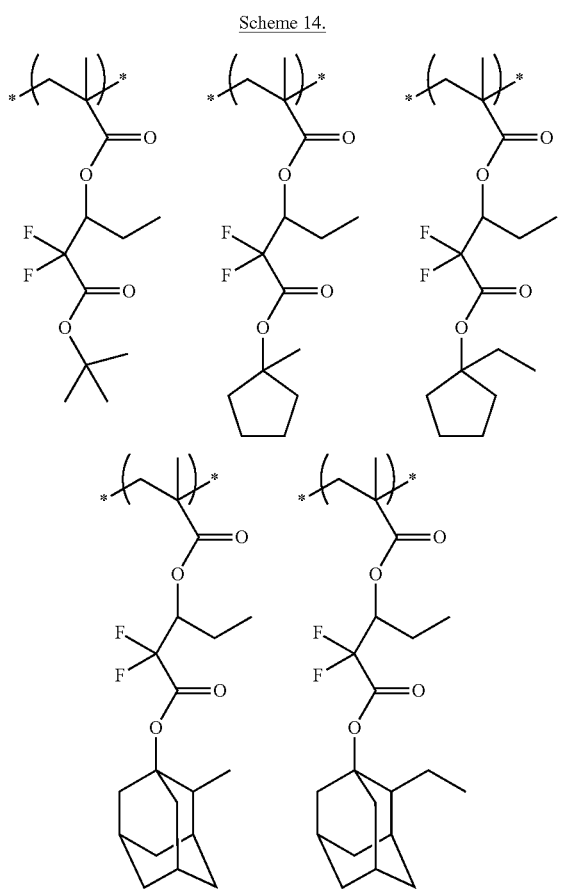

Other preferred examples of auxiliary repeating units include those of formula (51):

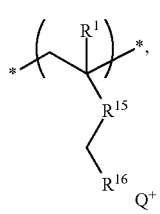

(51)

wherein

R$^1$ has the same definition as in the general formula (45),

R$^{15}$ represents a divalent linking group,

R$^{16}$ represents a monovalent group having a monovalent anion site, preferably either *—SO$_3$—, *—CO$_2$— or *—NHSO$_3$—, and Q$^+$ represents a monovalent cation, preferably either a sulfonium cation or an iodonium cation.

The linking group R$^{15}$ has the same definition as the linking group W$^1$ or W$^2$ described further above.

Particularly preferred examples of auxiliary repeating units of formula (51) are shown in Scheme 15. These auxiliary repeating units can be used singularly or in combination with other auxiliary repeating units.

Scheme 15.

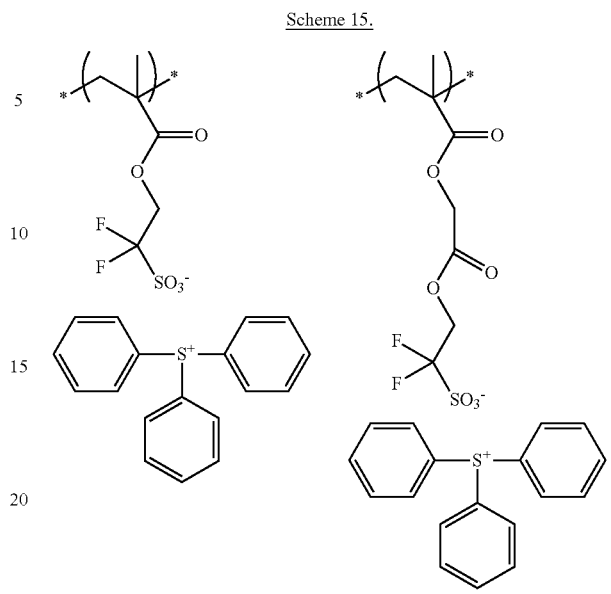

Auxiliary Monomers

Preferred auxiliary monomers for forming the auxiliary repeating units include those shown in Scheme 16. These auxiliary monomers can be used singularly or in combination with other auxiliary monomers.

Scheme 16.

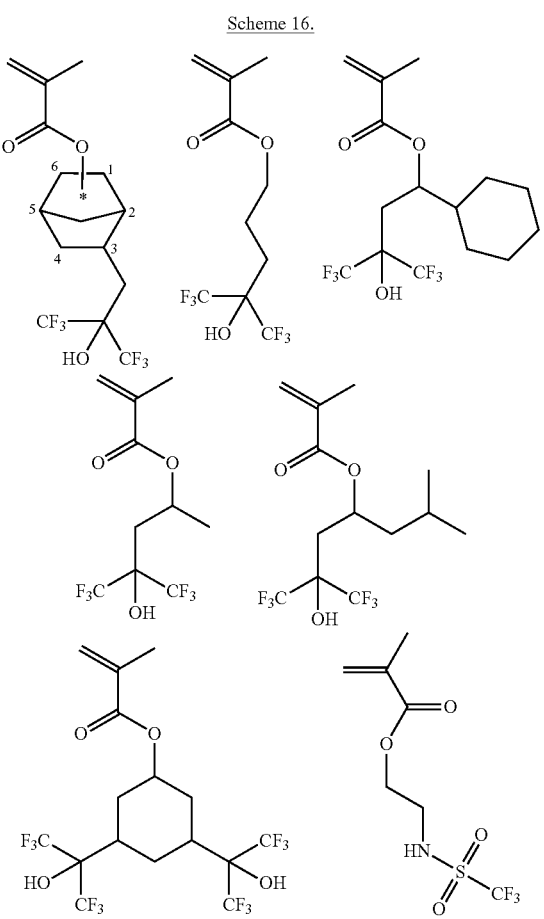

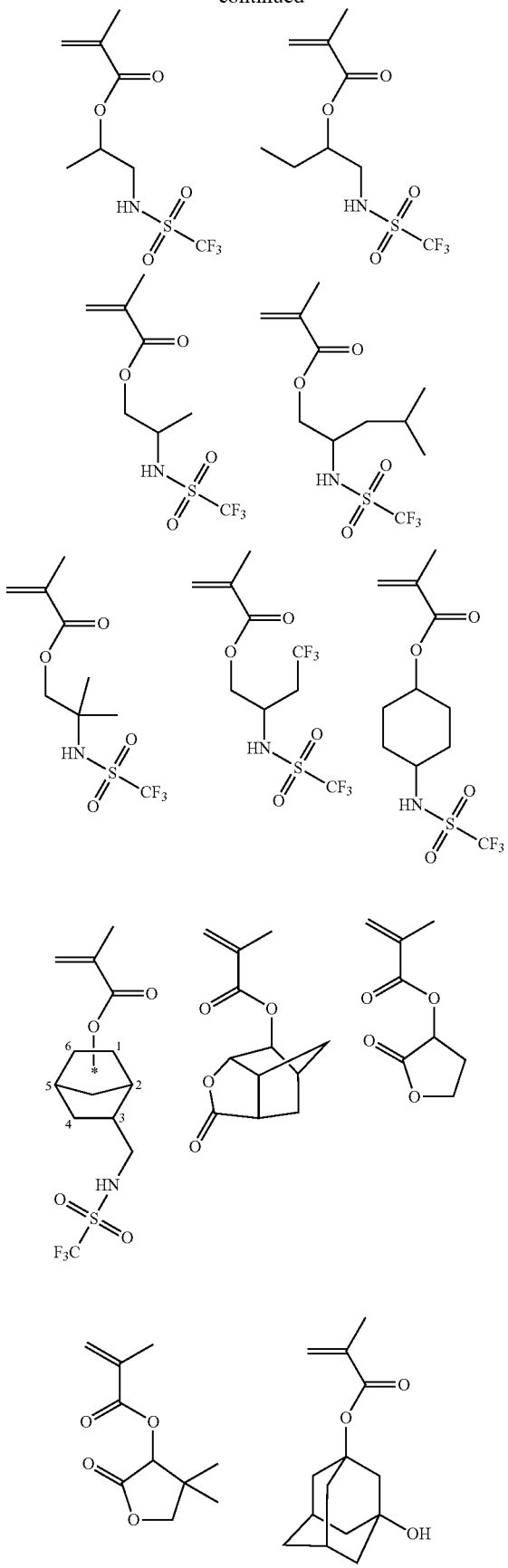
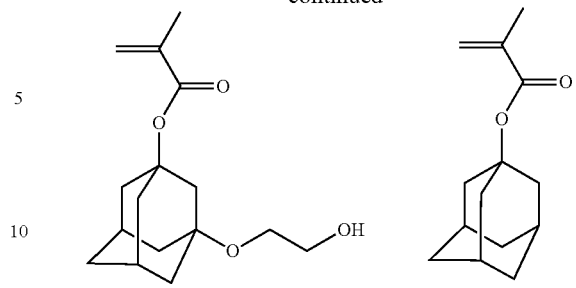

In an embodiment, the PAG polymer comprises 1 mol % to 15 mol % of the first repeating unit, wherein mol % is based on total moles of all monomers of the PAG polymer, 10 mol % to 50 mol % of a second repeating unit having a protected acid group capable of being deprotected by an acid, and 89 mol % to 35 mol % of an auxiliary repeating unit comprising a moiety selected from the group consisting of fluoroalcohols, fluorosulfonamides, lactones, alcohol, and combinations thereof. In another embodiment, the protected acid of the second repeating unit is a carboxylic acid group protected with an acid-labile functionality selected from the group consisting of tertiary esters, acetals, ketals, and orthoesters.

Preparation of PAG Polymer

A method of forming the PAG polymer comprises i) forming a reaction mixture comprising an above-described PAG monomer (precursor to the first repeating unit of formula (11)), a solvent and a polymerization initiator, and ii) allowing the PAG monomer to polymerize, thereby forming the PAG polymer. The reaction mixture can further comprise an acid labile second monomer (precursor to the second repeating unit) and an auxiliary monomer (precursor to the auxiliary repeating unit) as co-monomers in the polymerization, thereby forming a PAG polymer that is a linear random copolymer. Herein, a "linear polymer" comprises one polymer branch and two chain ends.

No particular limitation is placed on the polymerization process for preparing the PAG polymer comprising the first repeating unit of the general formula (11). Preferably, the PAG polymer is prepared by a radical polymerization process or ionic polymerization process. Other polymerization techniques include coordination anionic polymerization, living anionic polymerization, cationic polymerization, ring opening metathesis polymerization, vinylene polymerization, vinyl addition polymerization, and living radical polymerizations (e.g., atom transfer radical polymerization (ATRP), reversible addition-fragmentation chain-transfer polymerization (RAFT)). The following describes the radical polymerization process. However, it should be understood that the polymerization reaction can be conducted using another polymerization process.

The radical polymerization process can be done by a known polymerization technique (e.g., bulk polymerization, solution polymerization, suspension polymerization, emulsion polymerization techniques) in a batch, semi-continuous or continuous mode in the presence of a radical polymerization initiator and/or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, dimethyl-2,2-azobis(2-methylpropionate), tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction. Furthermore, the polymerization reaction can be performed with the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Water, ether solvents, cyclic ether solvents, fluorocarbon solvents and aromatic solvents can also be used. These solvents can be used solely or in combination of two or more thereof.

A molecular weight adjusting agent (chain transfer agent) such as mercaptan can be used in combination with the initiating agent.

The reaction temperature of the polymerization reaction is set as appropriate depending on the kind of the radical polymerization initiator or radical initiating source and is generally preferably in the range of 20 to 200° C., more preferably 30 to 140° C.

As a technique for removing water or the organic solvent from the obtained PAG polymer solution or dispersion, it is feasible to adopt re-precipitation, filtration, distillation by heating under reduced pressure, or the like.

Resist Composition

The PAG polymer comprising the repeating unit of formula (11) is used in a resist composition in the form of a solution mixed with other components. The PAG polymer functions as a photo-acid generator. When the PAG polymer further comprises a second repeating unit having an acid-labile group or a cross-linking site and is capable of photo-acid generation and chemical amplification, the PAG polymer can serve as the sole resin of the resist composition, without the addition of a second resin having a repeating unit comprising an acid-labile group or cross-linking site. In this instance, the addition of secondary resin is optional. In the case where the PAG polymer has the first repeating unit of the general formula (11) but does not have the second repeating unit with the acid-labile group or cross-linking site, the resist composition is prepared with the addition of a secondary resin as an essential component to the composition. When the secondary resin is present, the secondary resin is referred to as the "base resin". When the PAG polymer is the sole resin of the resist composition, the PAG polymer is the base resin The resist composition can include not only a solvent but also various additives commonly used for resist compositions such as, for example, an additive resin, a quencher, a dissolution inhibitor, a plasticizer, a stabilizer, a coloring agent, a surfactant, a viscosity improver, a leveling agent, an antifoaming agent, a compatibilizer, a primer, and/or an antioxidant. In the case of the negative resist composition, other additives such as a crosslinking agent and/or a basic compound can further be added. The additives can be used in addition to the following materials.

Base Resin

When a second resin is included in the resist composition, the second resin is referred to as the base resin. In this instance, the base resin can contain an acid-labile group so as to perform a positive resist function, or a cross-linking site so as to perform a negative resist function.

Examples of base resins for the positive resist composition are those comprising a repeat unit having a pendant carboxyl group or hydroxyl group protected by an acid-labile group on a side chain thereof, and a main chain portion derived from a polymerization of a vinyl polymerizable group, such as a repeat unit formed by polymerization of acrylic acid, methacrylic acid, α-trifloromethylacrylic acid, a vinyl group, an allyl group, and/or norbornene group.

Examples of the base resin for the negative resist composition are those comprising a repeat unit having a cross-linking site such as a hydroxyl group and/or a carboxyl group on a side chain thereof and a main chain portion resulting from a polymerization of a vinyl polymerizable group, such as a repeat unit formed by polymerization of acrylic acid, methacrylic acid, α-trifloromethylacrylic acid, vinyl group, allyl group, and/or norbornene group.

In many cases, the base resin is a copolymer for control of the resist characteristics. There are known various base resins. Herein, the above explanations of the copolymerization component, the acid-labile group, cross-linking site and linking group can be applied as they are to the base resin. As the copolymerization component of the base resin, a lactone ring-containing monomer is particularly preferred for improvement in the substrate adhesion of the resist composition.

The base resin generally has a number average molecular weight of 1,000 to 1,000,000, preferably 2,000 to 500,000, as measured by gel permeation chromatography (GPC). If the number average molecular weight of the base resin is less than 1,000, the resulting resist composition generally does not form a film with sufficient strength. If the number average molecular weight of the base resin exceeds 1,000,000, the solubility of the resin in the solvent decreases, adversely affecting the uniformity of films formed with the resist composition. The molecular weight distribution (Mw/Mn, PDI) of the base resin is preferably in the range of 1.01 to 3.00, most preferably 1.10 to 2.50.

Crosslinking Agents

For a negative resist composition, the cross-linking agent can be any compound formed by reacting an amino-containing compound (e.g., melamine, acetoguanamine, benzoguanamine, urea, ethylene urea, propylene urea, and glycoluril) with formaldehyde or a mixture of formaldehyde and lower alcohol, thereby substituting a hydrogen atom of the amino group with a hydroxymethyl group or a lower alkoxymethyl group. Herein, the cross-linking agents using melamine, urea, alkylene urea (e.g., ethylene urea, propylene urea, and the like) and glycoluril are hereinafter referred to as "melamine-based cross-linking agent", "urea-based cross-linking agent", "alkylene urea-based cross-linking agent" and "glycoluril-based cross-linking agent", respectively. The cross-linking agent is preferably at least one selected from the group consisting of melamine-based cross-linking agents, urea-based cross-linking agents, alkylene urea-based cross-linking agents and glycoluril-based cross-linking agents. Particularly preferred are glycoluril-based cross-linking agents.

Examples of the melamine-based cross-linking agents are hexamethoxymethylmelamine, hexaethoxymethylmelamine, hexapropoxymethylmelamine and hexabutoxymethylmelamine. Hexamethoxymethylmelamine is preferred.

Examples of the urea-based cross-linking agents are bismethoxymethylurea, bisethoxymethylurea, bispropoxymethylurea and bisbutoxymethylurea. Bismethoxymethylurea is preferred.

Examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; 1,3-di(methoxymethyl)-4,5-dihydroxy-2-imidazolidinone; and 1,3-di(methoxymethyl)-4,5-dimethoxy-2-imidazolidinone.

Examples of the glycoluril-based cross-linking agents are mono-, di-, tri- and/or tetra-hydroxymethylated glycoluril, mono-, di-, tri- and/or tetra-methoxymethylated glycoluril, mono-, di-, tri- and/or tetra-ethoxymethylated glycoluril, mono-, di-, tri- and/or tetra-propoxymethylated glycoluril and mono-, di-, tri- and/or tetra-butoxymethylated glycoluril.

The total amount of the cross-linking agent used is preferably 3 to 30 parts by mass, more preferably 3 to 25 parts by mass, most preferably 5 to 20 parts by mass, per 100 parts by mass of the base resin of the resist composition. If the total amount of the cross-linking agent is less than 3 parts by mass of the base resin, the resist composition is generally not capable of sufficient cross-linking to form a desirable resist pattern. The resist composition can exhibit poor storage stability and/or deteriorate in sensitivity with time if the total amount of the cross-linking agent exceeds 30 parts by mass of the base resin.

Basic Compounds

The basic compound is preferably contained as an optional component in the resist composition so as to function as a quencher or to obtain improvements in resist pattern shape and post exposure stability.

Exemplary basic compounds include primary, secondary and tertiary aliphatic amines, aromatic amines, heterocyclic amines, nitrogen-containing compounds with hydroxyphenyl group, alcoholic nitrogen-containing compounds and amide derivatives. Secondary and tertiary aliphatic amines, aromatic amines and heterocyclic amines are preferred.

The aliphatic amines can be in the form of alkylamines or alkylalcoholamines each obtained by replacing at least one hydrogen atom of ammonia ($NH_3$) with a $C_1$-$C_{12}$ alkyl or hydroxyalkyl group. Examples of the aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines including aniline, aniline derivatives such as N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine, heterocyclic amines such as 1,5-diazabicyclo[4.3.0]non-5-ene, 1,8-diazabicyclo[5.4.0]undec-7-ene, 1,4-diazabicyclo[2.2.2]octane, 4-dimethylaminopyridine, hexamethylenetetramine and 4,4-dimethylimidazoline, and hindered amines such as bis(1,2,2,6,6-pentamethyl-4-piperidyl)sebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, and 1-[2-(2-hydroxyethoxy)ethyl]piperazine. The basic compounds can be used singularly or in combination.

The amount of the basic compound used is generally 0.01 to 5 parts by mass per 100 parts by mass of the base resin of the resist composition.

Acid Additives

In the case of the negative resist resin, an organic carboxylic acid, a phosphorus oxo acid, and/or a derivative thereof can be added as an optional component in order to prevent sensitivity deterioration caused by the addition of the basic compound and to obtain improvements in resist pattern shape and post exposure stability. This acid compound can be used singularly or in combination with the basic compound.

Exemplary organic carboxylic acid include malonic acid, citric acid, malic acid, succinic acid, benzoic acid and salicylic acid.

Suitable examples of the phosphorus oxo acid and its derivatives are: phosphoric acids and ester derivatives thereof, such as phosphoric acid, di-n-butyl phosphate and diphenyl phosphate; phosphonic acids and ester derivatives thereof, such as phosphonic acid, dimethyl phosphonate, di-n-butyl phosphonate, phenylphosphonic acid, diphenyl phosphonate and dibenzyl phosphonate; and phosphinic acids or ester derivatives thereof, such as phosphinic acid and phenylphosphinic acid. Phosphonic acid is particularly preferred.

Solvents

There is no particular limitation on the organic solvent as long as the PAG polymer can be dissolved in the organic solvent. Non-limiting organic solvent include: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, propylene glycol monomethyl ether, propylene glycol monomethyl etheracetate (PGMEA), dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used singularly or in combination.

Surfactants

Preferred surfactants for the resist composition include one or more fluorine- and/or silicon-based surfactants (i.e., fluorine-based surfactant, silicon-based surfactants, and surfactant containing both of fluorine and silicon atoms).

A resist composition comprising a surfactant is generally effective for use with an exposure light source of 250 nm or less wavelength, notably 220 nm or less wavelength and for pattern formation with a narrower pattern line width. It is possible to attain good sensitivity and resolution and obtain good resist patterning with less adhesion/development failures.

Non-Resinous Acid Generator

The resist composition can include a non-resinous photo-acid generator in combination with the PAG polymer. These include common photo-acid generators for chemically amplified resist compositions. Exemplary non-resinous photo-acid generators include bis-sulfonyldiazomethanes, nitrobenzyl derivatives, onium salts, halogen-containing triazine compounds, cyano-containing oximesulfonate compounds and other oximesulfonate compounds. These photo-acid generators can be used singularly or in combination. The amount of the photo-acid generator used, including the PAG polymer, is generally in the range of 0.5 to 20 parts by mass per 100 parts by mass of the resist composition. If the amount of the photo-acid generator is less than 0.5 parts by mass, the resist composition is generally not effective in forming good resist patterns. If the amount of the photo-acid generator exceeds 20 parts by mass, it is difficult to prepare the resist composition as a uniform solution. Moreover, storage stability of the resist composition decreases. The PAG polymer is generally used in an amount of 1 to 100 parts by mass, preferably 10 to 100 parts by mass, more preferably 30 to 100 parts by mass, per 100 parts by mass of the total photoacid generator content.

Additive Resins

The resin composition can include resins in addition to the PAG polymer and secondary resin (base resin). There is no particular limitation placed on the additive resin as long as the additive resin can be dissolved in the solvent used and has compatibility with the other components of the resist composition. The additive resin can function as an in-situ top coat, a plasticizer, a stabilizer, as a viscosity improver, a leveling agent, an antifoaming agent, a compatibilizer, and/or a primer.

Pattern Formation Method

The following discussion pertains to a method of patterning a desired substrate, such as, for example, a silicon wafer, a chrome-on-glass mask blank, or a printed circuit board using a resist composition comprising the PAG polymer as the base resin, (i.e., the PAG polymer comprises the photosensitive first repeating unit and acid labile second repeating unit, and is capable of photo-acid generation as well as chemical amplification by formation of acid groups). In this instance, a positive-tone lithographic pattern can be formed, as illustrated in the schematic layer diagrams of FIGS. 1A to 1E. A resist composition comprising at least the PAG polymer and a solvent is disposed on surface 12 of substrate 10 (FIG. 1A) using any suitable coating technique (e.g., spin casting) followed by removal of the solvent to form resist layer 22 of structure 20 (FIG. 1B). Resist layer 22 comprises the solid components of the resist composition. Resist layer 22 can be treated with an optional post-application bake (PAB) and/or an optional solvent rinse under suitable conditions of time and temperature before exposure. Pattern-wise exposure of resist layer 22 to high energy radiation results in exposed resist layer 32 of structure 30 (FIG. 1C). It is particularly effective to use an exposure device having a light source for irradiating high energy radiation of wavelength 124 nm or less, such as EUV, x-ray, and/or E-beam.

Optionally, the resist layer can be exposed using a liquid immersion exposure device that uses a medium such as water and/or a fluorinated solvent in the optical path, which causes less absorption of high energy radiation and enables more efficient fine processing in terms of numerical aperture and effective wavelength.

Figure 1E:
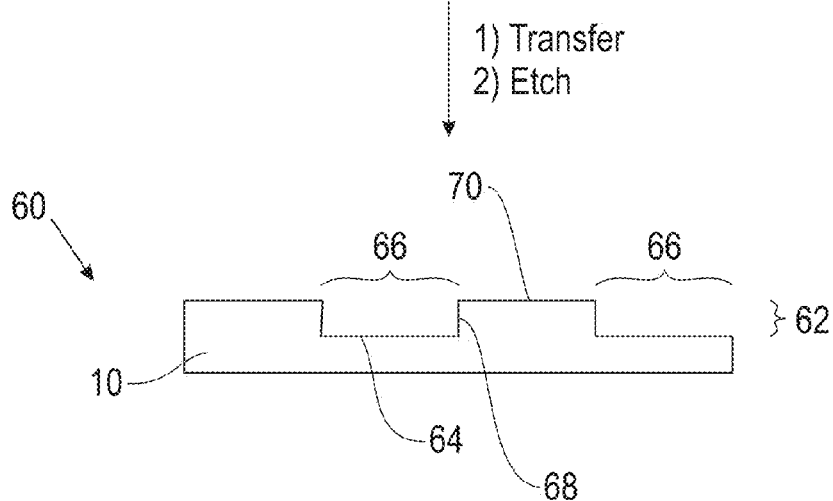

Exposed resist layer 32 is composed of regions of exposed resist 34 and regions of non-exposed resist 36. Exposed resist layer 32 can be treated with an optional post-exposure bake (PEB) and/or an optional solvent rinse under suitable conditions of time and temperature before development. The exposed resist 34 and/or baked exposed resist 34 has greater solubility in an aqueous alkaline developer compared to non-exposed resist 36. Consequently, aqueous alkaline development affords a positive-tone image by removing regions of exposed resist 36. The PAB, PEB and/or solvent rinse(s) can enhance solubility differences of the exposed and non-exposed resist in a given developer. Development in an aqueous alkaline developer produces layered structure 40 comprising patterned resist layer 42 (FIG. 1D). Patterned resist layer 42 is a topographical relief pattern comprising resist features 44 composed of non-exposed resist 34. Resist features 44 are disposed on surface 46 of substrate 10 and have top surface 48 and sidewall 50. Substrate surface 52 is in contact with air. The topographical relief pattern of patterned resist layer 42 can be transferred to substrate 10 by known methods followed by removal of resist features 44 (e.g., oxygen ion etching), resulting in structure 60 (FIG. 1E). Structure 60 comprises a transferred topographical pattern 62 within substrate 10, whose features 66 comprise bottom surface 64, sidewall surface 68, and top surface 70 of substrate 10.

The resist layer can be rinsed before or after the exposure, the PAB, and/or the PEB with a solvent (e.g., water, aqueous solutions, including water/alcohol mixtures, and organic solvents). Typically, the rinse is performed after the PAB. Rinses can be performed at or near room temperature (e.g., 10° C. to 50° C.) for a period of 1 second to 1 hour.

Optionally, the pre-developed resist layer and/or post-developed resist layer can be treated with water vapor and/or alcohol vapor either at room temperature or at elevated temperature on a time scale of 1 minute to 5 hours. Such a treatment after exposure and PEB can be conducted, for example, to promote additional acid induced deprotection of acid sensitive groups.

The term "substrate" refers to all underlying layers of a structure on which the resist layer is disposed. The substrate can have one or more layers arranged in a stack. In a multi-layered substrate, the layer directly below and in contact with the resist layer is the top-most layer of the substrate, also referred to as "the underlayer" to the resist layer. The terms "surface" or "underlying surface" refer to the substrate surface on which the resist layer is disposed. As non-limiting examples, the resist layer can be disposed on the surface of a silicon wafer or a metal foil, or more particularly on the surface of an anti-reflection layer (ARC) of a multi-layer substrate, where the ARC layer is the top-most layer of the substrate. In this example, the ARC layer is also the underlayer of the resist layer. In another example, the ARC layer has a polymer brush layer attached to the top surface. In this example, the polymer brush layer is also the underlayer of the resist layer.

The term "disposed" refers to a layer in contact with a surface of another layer. "Disposing" or "applying" refer to forming a layer to be in contact with a surface of another layer, without limitation as to the method employed unless otherwise stated, providing the desirable properties of the disposed or applied layer are not adversely affected (e.g., uniformity and thickness).

The term "casting" refers to forming a layer of a material by disposing a solution of the material dissolved in a solvent on a surface of another layer, and removing the solvent.

It should be understood that in some cases (e.g., when forming dense, high resolution patterns) all of the resist layer can receive some dose of radiation exposure. "Non-exposed resist" refers to resist that has received an insufficient dose to switch the solubility of the resist in a given developer compared to the pre-exposed resist (including pre-exposed resist that has been treated with an optional bake and/or optional rinse). "Exposed resist" has received sufficient exposure to switch the solubility of the resist in a given developer compared to the pre-exposed resist.

"Polarity change" implies an altered chemical composition that affects relative solubility without crosslinking. The extent of the polarity change can be measured by comparing the solubility of the exposed resist and non-exposed resist in a given developer. "Inducing a polarity change" in the resist layer means subjecting the resist layer to a treatment involving exposure, a post-exposure bake (PEB) and/or an optional rinse that alters the chemical composition of the layer such that the treated resist has a different solubility compared to the pre-treated resist in a given developer (e.g., tetramethylammonium hydroxide (TMAH) solution in water).

The optional baking (PAB and/or PEB) treatments and/or optional rinsing treatments can enhance the solubility difference of the exposed resist compared to the non-exposed resist. A PAB and/or PEB can be used to facilitate deprotection of acid sensitive protecting groups and/or elimination of reaction byproducts of the resist composition.

The optional post-application bake (PAB) treatment is typically performed at a temperature of 50° C. to 250° C. for a period of 1 second to 10 minutes, more specifically 90° C. to 130° C. for about 1 minute. The PAB can be used to dry the film of excess solvent, remove unwanted or excess organic ligand, and/or partially crosslink the resist layer. The thermally treated dry film typically will have a thickness of 0.01 micrometers to 10 micrometers, depending on the subsequent radiation source and the desired application.

The optional post-exposure bake (PEB) can be performed at a temperature of 50° C. to 300° C. for 1 second to 10 minutes, more specifically 90° C. to 130° C. for about 1 minute.

Developers

The aqueous alkaline developer for positive tone development can comprise any suitable base. Non-limiting exemplary bases include sodium hydroxide, potassium hydroxide, sodium carbonate, and various tetraalkylammonium hydroxides such as, for example, tetramethylammonium hydroxide (TMAH) and tetrabutylammonium hydroxide (TBAH). The aqueous alkaline developer can comprise one or more bases. Preferably, the aqueous alkaline developer comprises a tetraalkylammonium hydroxide, more preferably tetramethylammonium hydroxide. Preferably, the TMAH developer comprises 0.1 to 5 wt % tetramethylammonium hydroxide (TMAH) based on total weight of the developer solution in water.

The organic solvent developer for negative tone development can comprise any suitable organic solvent. Non-limiting exemplary organic solvents include ketone-based solvents, ester-based solvents, alcohol-based solvents, amide-based solvents, ether-based solvents, and hydrocarbon-based solvents. More specific organic solvent developers include methyl benzoate (MeB), ethyl 3-ethoxypropionate (EEP), 2-heptanone (MAK), 4-methyl-2-pentanone (4M2P), n-butyl acetate (NBA), propylene glycol methyl ether acetate (PG-MEA), anisole, acetophenone, and combinations thereof.

Post-Development Treatment

The patterned resist layer can also be given a post-development treatment, for example, to increase etch resistance. The post-development treatment can be photochemical, thermal, chemical, or a combination thereof. As an example, the patterned resist layer can be given a second exposure to a second radiation, thereby forming a treated patterned resist layer. The second exposure can be performed with a single wavelength of second radiation or a combination of suitable wavelengths (broad band) of second radiation, so long as the exposure is effective in inducing the desired response of the treated patterned resist layer. The second exposure treatment can be a flood exposure. The flood exposure can be a single conventional whole area exposure or a combination of conventional whole area exposures. The exposure treatment can also be a scanning exposure delivered by a digital writing device employing light emitting sources. The second exposure can be followed by a thermal treatment to chemically amplify the formation of chemical functional groups in the treated patterned resist layer. For example, the flood exposure can release an acid from previously unreacted photoacid generator (PAG) that upon subsequent heating catalyzes the deprotection of additional acid-sensitive carboxylic acid esters, aromatic acetals/ketals, and/or carbonates, thereby increasing the concentration of carboxylic acid and phenol groups in the treated patterned resist layer. With sufficient polarity change, the treated patterned resist layer can be rendered insoluble in either a low polarity solvent (e.g., anisole) or a more polar organic solvent, while retaining solubility in aqueous alkaline developer and/or a second organic solvent, without crosslinking the resist.

A post-development thermal treatment can further tailor the solvent compatibility, chemical structure of the resist material, and/or etch resistance of the patterned resist layer. The thermal treatment can be conducted at a temperature of 50° C. to 600° C., 50° C. to 300° C., or 50° C. to 200° C. for a period of 1 sec to 1 day.

A chemical treatment can include, for example, contacting the patterned resist layer with the vapors of a volatile Lewis acid, such as hydrochloric acid, sulfuric acid, nitric acid, or a sulfonic acid. In each type of treatment, the chemical alteration of the resist is preferentially uniformly distributed throughout the treated resist, not just at the surface. The post-development chemical treatment can cause a chemical change in the revealed surface of the substrate, producing (after removal of the resist features) a chemically patterned surface of the substrate.

Etching includes any common etching technique applied in the manufacture of semiconductor devices, for example, dry-etching such as plasma etching, or wet-etching using selective solvents. Typically, dry etching processes are employed for etching at sub-50 nm dimensions.

Substrate

The substrate, and more particularly the surface of the substrate, can comprise inorganic or organic materials such as metals, carbon, or polymers. More particularly, the substrate can comprise any semiconducting material including, for example, Si, SiGe, SiGeC, SiC, Ge alloys, GaAs, InAs, InP, as well as other III-V or II-VI compound semiconductors. The substrate can also comprise a layered semiconductor such as Si/SiGe, or a semiconductor-on-insulator (SOI). In particular, the substrate can contain a Si-containing semiconductor material (i.e., a semiconductor material that includes Si) such as, for example, silicon dioxide, silicon nitride, and quartz. The semiconductor material can be doped, undoped or contain both doped and undoped regions therein.

Figure 2:
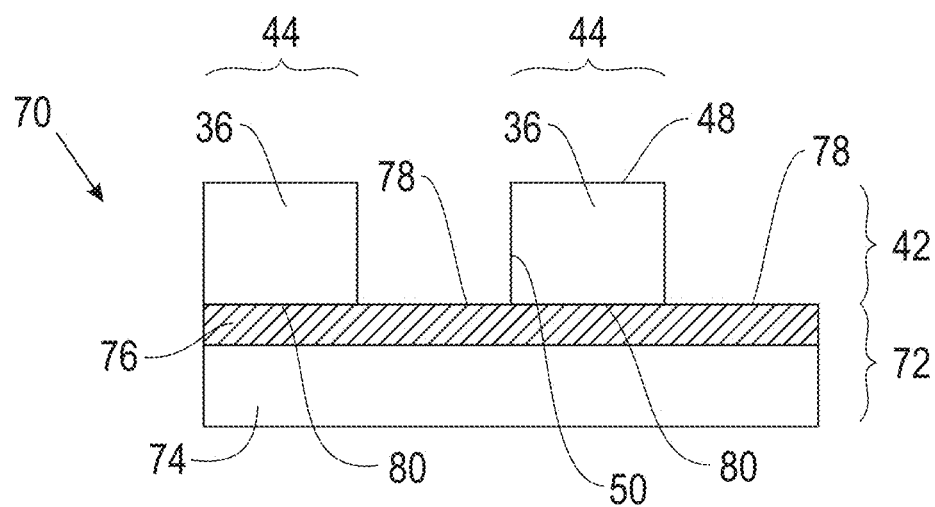
FIG. 2 is a schematic layer diagram of multi-layered structure that includes a topographical patterned layer comprising exposed resist composition disposed on a two layered substrate.

To further illustrate a multi-layered substrate, structure 40 of FIG. 1D is reproduced as structure 70 of FIG. 2, with the exception that substrate 72 of FIG. 2 has two layers, a bottom layer 74 and an intermediate layer 76. Bottom layer 74 of substrate 72 can be, for example, a silicon wafer. Intermediate layer 76 can be, for example, an ARC layer. In this example, surface 78 is a surface of the ARC layer in contact with air, and resist features 44 are disposed on ARC surface 80.

The following examples demonstrate the preparation of the PAG monomers, PAG polymers, resist compositions thereof, and resist patterns formed thereof.

EXAMPLES

Materials used in the following examples are listed in Table 1.

TABLE 1

| ABBREVIATION | DESCRIPTION | SUPPLIER |
|---|---|---|
| MF-26A | 2.3 wt % aqeous tetramethyl ammonium hydroxide solution (TMAH) | FUJIFILM |
| | 2-Phenyl benzimidazole | Sigma-Aldrich |
| | 2-(Fluorosulfonyl)difluoroacetyl fluoride | Sigma-Aldrich |
| | N-hydroxy-1,8-naphthalimide sodium salt | Kodak |
| | 4-Vinyl aniline | Sigma-Aldrich |
| | 2-Aminoethyl methacrylate HCl salt | Sigma-Aldrich |
| | 4-(Chlorosulfonyl)benzoic acid | Sigma-Aldrich |
| | 2,3,5,6-Tetrafluoro-4-sulfobenzoic acid | TCI |
| PCl$_5$ | Phosphorous pentachloride | Sigma-Aldrich |
| POCl$_3$ | Phosphorous(V) oxychloride | Sigma-Aldrich |
| NBHFAMA | 2-{[5-(1',1',1'-trifluoro-2'-trifluoromethyl-2'- hydroxy)propyl]-norbornyl]} methacrylate | Central Glass |
| EATf-MA | 2-{[(Trifluoromethyl)sulfonyl]amino} ethyl methacrylate | Central Glass |
| STHFA | 1,1,1,3,3,3-Hexafluoro-2-(4-vinylphenyl)-2-propanol | Central Glass |
| NLM | 5-methacryloxy-2,6-norbornanecarbolactone | Prepared below |
| EAdMA | 2-Ethyl-2-adamantyl methacrylate | ChemOrganic Limited, China? |
| ECPMA | 1-Ethylcyclopentyl methacrylate | Prepared below |
| MCPMA | 1-Methylcyclopentyl methacrylate | Prepared below |
| HS | 4-Hydroxystyrene | Prepared below |
| TPS-UMA | Triphenylsulfonium 2-((2-Methacryloyloxy)Ethylcarbamoyloxy)-1,1-Difluoroethanesulfonate; MW 579.1 | Central Glass |
| EIMA | 2-methacryloxyethyl isocyanate | Sigma-Aldrich |

Herein, Mn is the number average molecular weight, Mw is the weight average molecular weight, and MW is the molecular weight of one molecule.

The following examples are intended to provide those of ordinary skill in the art with a complete disclosure and description of how to prepare and use the compositions disclosed and claimed herein. Efforts have been made to ensure accuracy with respect to numbers (e.g., amounts, temperature, etc.), but allowance should be made for the possibility of errors and deviations. Unless indicated otherwise, parts are parts by weight, temperature is in degrees centigrade (° C.) and pressure is at or near atmospheric. Additionally, all starting materials including the co-monomers other than the PAG monomers were obtained commercially or were synthesized using known procedures.

Where appropriate, the following techniques and equipment were utilized in the examples below: $^1$H and $^{13}$C NMR spectra were obtained at room temperature on an Avance 400 spectrometer. Quantitative $^{13}$C NMR was run at room temperature in acetone-d$_6$ in an inverse-gated $^1$H-decoupled mode using Cr(acac)$_3$ as a relaxation agent on an Avance 400 spectrometer. Thermo-gravimetric analysis (TGA) was performed at a heating rate of 5° C./min in N$_2$ on a TA Instrument Hi-Res TGA 2950 Thermogravimetric Analyzer. Differential scanning calorimetry (DSC) was performed at a heating rate of 10° C./min on a TA Instruments DSC 2920 modulated differential scanning calorimeter. Molecular weights were measured in tetrahydrofuran (THF) or dimethylformamide (DMF) on a Waters Model 150 chromatograph relative to polystyrene standards.

The preparation of triphenylsulfonium 2-hydroxy-1,1-difluoroethanesulfonate (TPSHDS) is described in US20110319652 A1 to Jodry, et al.

The preparation of 1-methylcyclopentyl methacrylate (MCPMA) is described in U.S. Pat. No. 6,136,501 to Trefonas III, et al.

2-Ethyl-2-adamantyl methacrylate (EAdMA) is commercially available from ChemOrganic Limited, China.

The preparation of 2-{[5-(1',1',1'-trifluoro-2'-trifluoromethyl-2'-hydroxy)propyl]norbornyl]}methacrylate (Nb-HFAMA) is described in U.S. Pat. No. 7,014,980 B2 to Allen, et al.

The preparation of 5-methacryloxy-2,6-norbornanecarbolactone (NLM) is described in U.S. Pat. No. 7,378,683 B2 to Endoh, et al. NLM is also commercially available from Kuraray Fine Chemicals, Japan.

Preparation of hydroxy styrene monomer (HS) in tetrahydrofuran.

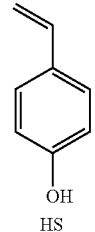

HS

A 3 liter round bottom flask was equipped with a mechanical overhead stirrer, thermocouple thermometer, and an addition funnel equipped with a nitrogen gas inlet. The flask was charged with 4-acetoxy styrene (454 g, 2.8 mol) and 1820 grams tetrahydrofuran (THF). The addition funnel was charged with 240 mL of 12 molar aqueous ammonium hydroxide (approximately 3.5 mol). The flask was nitrogen flushed and kept under a nitrogen blanket as the ammonium hydroxide was added to the rapidly stirred solution over 30 minutes. A slight exotherm of about 10° C. was observed. The mixture was allowed to stir at room temperature overnight. The reaction mixture was transferred to a 6 liter separatory funnel and washed with one 2 liter portion of brine followed by four 1 liter brine extractions. The THF solution was dried by stirring overnight with 50 grams of anhydrous magnesium sulfate. After removing the magnesium sulfate the by filtration the solution was concentrated on the rotary evaporator using house vacuum and a bath temperature of 30° C. The concentrated solution (555 grams) contained 49.3 mole % 4-hydroxystyrene (81% yield) and 50.7 mole % of tetrahydrofuran by NMR analysis. Additional tetrahydrofuran was added to obtain a solution containing 23-26 mole % 4-hydroxystyrene as determined by NMR analysis.

Preparation of PAG monomer, triphenylsulfonium 2-((2-methacryloyloxy)ethylcarbamoyloxy)-1,1-difluoroethanesulfonate (TPS-UMA):

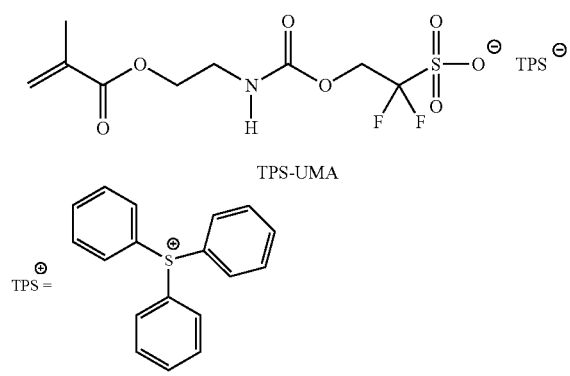

TPS-UMA

TPS = 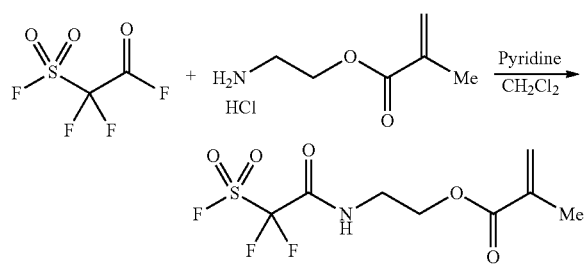 (note: structure of triphenylsulfonium cation)

Triphenyl sulfonium 2-hydroxy-1,1-difluoroethane-sulfonate (TPSHDS) (131 g, 0.284 mol), a catalytic amount of dimethylamino pyridine (DMAP) (about 0.025 g), and 2-methacryloxyethyl isocyanate (EIMA) (40 g, 0.256 mol) were mixed in acetonitrile (400 mL) and heated for 10 hours at 45° C. The solvent was evaporated and then, the desired material was extracted from $CHCl_3$/water solution. The $CHCl_3$ solution mixture was washed with ether. The desired material was obtained as $CHCl_3$ solution (129 g solution, 77.5 g solid, 52% yield). $^1$H NMR ($CDCl_3$); delta=7.76-7.63 (m, 15H; $Ph_3S^+$), 6.07 (s, 1H; =$CH_2$), 5.53 (t, J=1.6 Hz, 2H; =$CH_2$), 5.38 (s, 1H; NH), 4.72 (t, J=15.0 Hz, 2H; $CF_2CH_2$), 4.16 (t, J=5.4 Hz, 2H; $OCH_2$), 3.44 (q, J=5.3 Hz, 2H; $NHCH_2$), 1.88 (t, J=1.1 Hz, 3H; $CH_3$). $^{19}$F NMR ($CDCl_3$, $CFCl_3$ as standard); delta=−114.3 (t, J=16.0 Hz, 2F).

Preparation of PAG Monomers

Example 1

Synthesis of PAG monomer 1 (PAG-1). This preparation was performed in two steps.

Step A: synthesis of 2-(2,2-difluoro-2-(fluorosulfonyl)acetamido)ethyl methacrylate

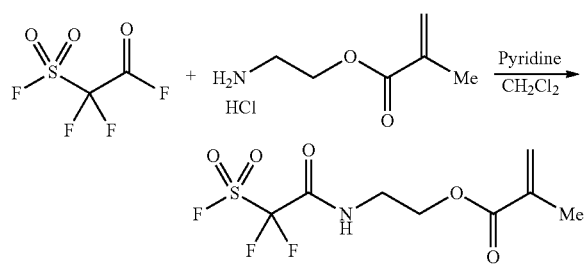

A 500 ml flask was charged with $CH_2Cl_2$ (80 ml) under nitrogen stream and stirred for 10 min at 0° C. and then 2-(fluorosulfonyl)difluoroacetyl fluoride (29.9 g, 166.0 mmol, 1.5 equivalent (eq.)) was added. After 25 minutes, a $CH_2Cl_2$ (160 ml) solution of 2-aminoethyl methacrylate hydrochloride (18.4 g, 111.0 mmol, 1.0 eq.) and pyridine (17.5 g, 221.0 mmol, 2.0 eq.) was added drop wise to the mixture over 50 minutes. The mixture was allowed to warm to room temperature (RT) and stirred for 3 hours at RT. 1N HCl was added to the final reaction mixture and the lower layer was separated and washed with 1N HCl and Brine. The solution was dried over anhydrous $MgSO_4$, filtrated and then $CH_2Cl_2$ was removed by an evaporator. The crude product was purified by recrystallization (hexane/$CHCl_3$). The target compound was obtained as a white solid (20.4 g) in 64% yield. $^1$H-NMR (400 MHz, $CDCl_3$); delta=1.93 (dd, J=1.1, 1.2 Hz, 3H), 3.73 (td, J=5.4, 5.2 Hz, 2H), 4.35 (dd, J=5.1, 5.0 Hz, 2H), 5.63 (dq, J=1.4, 1.5 Hz, 1H), 6.12-6.14 (m, 1H), 7.09 (brs, 1H). $^{19}$F-NMR (376 MHz, $CDCl_3$, $C_6F_6$ as standard); delta=40.68 (t, J=5.1 Hz, 1F), −105.91 (d, J=4.8 Hz, 2F).

Step B: Synthesis of PAG-1

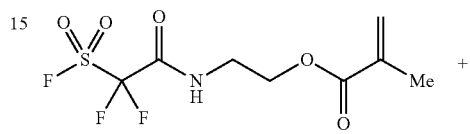

+

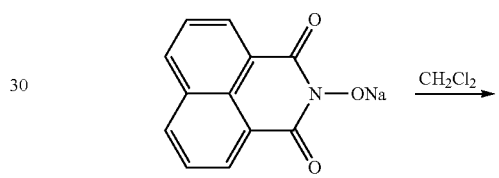

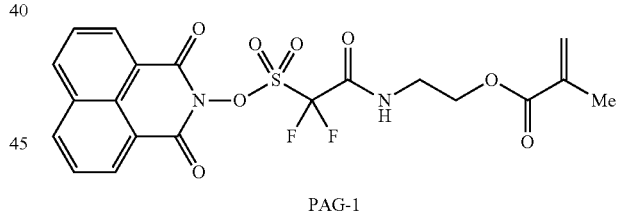

PAG-1

A 1000 ml flask was charged with 2-(2,2-difluoro-2-(fluorosulfonyl)acetamido)ethyl methacrylate (13.6 g, 47.0 mmol, 1.0 eq.) and $CH_2Cl_2$ (282 ml) under nitrogen stream and then N-hydroxy-1,8-naphthalimide sodium salt (12.0 g, 56.4 mmol, 1.2 eq.) was added. The mixture was stirred for 17 hours at RT. A solid was removed by filtration and the solid was washed with $CHCl_3$. Aqueous saturated $NaHCO_3$ (sat. $NaHCO_3$ aq.) was added to the combined filtrate and the lower layer was separated and washed with sat. $NaHCO_3$ aq. and brine. The solution was dried over $MgSO_4$, filtrated and then solvents were removed by an evaporator. The crude product was purified by recrystallization (hexane/$CHCl_3$). The target compound was obtained as a white solid (10.4 g) in 46% yield. $^1$H NMR (400 MHz, $CDCl_3$); delta=1.87 (dd, J=1.0, 1.3 Hz, 3H), 3.83 (td, J=5.3, 5.5 Hz, 2H), 4.36 (dd, J=5.4, 5.1 Hz, 2H), 5.49 (dq, J=1.4, 1.6 Hz, 1H), 6.11-6.14 (m, 1H), 7.85 (dd, J=8.1, 7.5 Hz, 2H), 8.36 (dd, J=8.3, 1.0 Hz, 2H), 8.64 (dd, J=7.3, 1.0 Hz, 2H), 8.76 (brs, 1H). $^{19}$F-NMR (376 MHz, CDCl$_3$, C$_6$F$_6$ as standard); delta=−104.63 (s, 2F).

Example 2

Synthesis of PAG monomer 2 (PAG-2). This preparation was performed in two steps.

Step A: synthesis of 1,1-difluoro-2-oxo-2-(4-vinylphenylamino)ethanesulfonyl fluoride

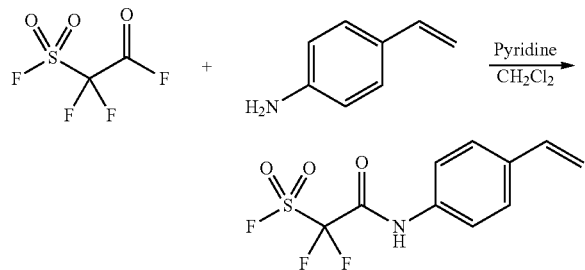

A 100 ml flask was charged with CH$_2$Cl$_2$ (24 ml) under nitrogen stream and stirred for 10 min at 0° C. and then 2-(fluorosulfonyl)difluoroacetyl fluoride (6.60 g, 37.6 mmol, 1.5 eq.) was added. After 20 minutes, the CH$_2$Cl$_2$ (12 ml) solution of 4-vinyl aniline (2.86 g, 24.4 mmol, 1.0 eq.) and pyridine (1.93 g, 24.4 mmol, 1.0 eq.) was added dropwise to the mixture over 10 minutes. The mixture was allowed to warm to RT and was stirred for 4 hours at RT. 1N HCl was added to the final reaction mixture and the lower layer was separated and washed with 1N HCl and brine. The solution was dried over MgSO$_4$, filtrated and then CH$_2$Cl$_2$ was removed by an evaporator. The target compound was obtained as a white solid (6.57 g) in 96% yield. $^1$H NMR (400 MHz, CDCl$_3$); delta=5.28 (d, J=10.9 Hz, 1H), 5.74 (d, J=17.6 Hz, 1H), 6.68 (dd, J=10.9, 17.6 Hz, 1H), 7.43 (d, J=8.6 Hz, 2H), 7.53 (d, J=8.7 Hz, 2H), 8.04 (brs, 1H). $^{19}$F-NMR (376 MHz, CDCl$_3$, C$_6$F$_6$ as standard) delta=41.27 (t, J=4.6 Hz, 1F), −105.26 (d, J=4.2 Hz, 2F).

Step B: Synthesis of PAG-2

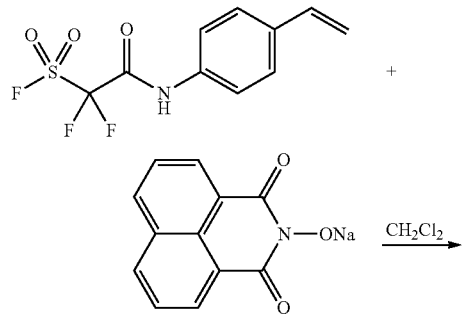

-continued

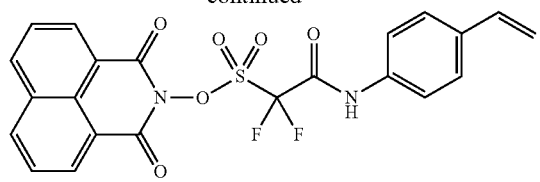

A 100 ml flask was charged with 1,1-difluoro-2-oxo-2-(4-vinylphenylamino)ethanesulfonyl fluoride (1.40 g, 5.0 mmol, 1.0 eq.) and CH$_2$Cl$_2$ (50 ml) under nitrogen stream and then N-hydroxy-1,8-naphthalimide sodium salt (1.18 g, 5.0 mmol, 1.0 eq.) was added. The mixture was stirred for 21 hours at RT. A solid was removed by filtration and the solid was washed with CH$_2$Cl$_2$. 1N HCl was added to the combined filtrate and the lower layer was separated and washed with saturated aqueous NaHCO$_3$ and brine. The solution was dried over MgSO$_4$, filtrated and then CH$_2$Cl$_2$ was removed by an evaporator. The crude product was purified by recrystallization (Hexane/CHCl$_3$). The target compound was obtained as white solid (1.28 g) in 54% yield. $^1$H-NMR (400 MHz, CDCl$_3$); delta=5.23 (d, J=11.3 Hz, 1H), 5.71 (dd, J=0.6, 17.6 Hz, 1H), 6.67 (dd, J=10.9, 17.6 Hz, 1H), 7.41 (d, J=8.6 Hz, 2H), 7.72 (d, J=8.7 Hz, 2H), 7.88 (dd, J=8.2, 7.4 Hz, 2H), 8.38 (dd, J=8.3, 1.0 Hz, 2H), 8.75 (dd, J=7.4, 1.1 Hz, 2H), 10.60 (brs, 1H). $^{19}$FNMR (376 MHz, CDCl$_3$, C$_6$F$_6$ as standard); delta=−104.80 (s, 2F)

Example 3

Synthesis of PAG monomer 3 (PAG-3). This preparation was performed in three steps.

Step A: chlorination of 4-(chlorosulfonyl)benzoic acid

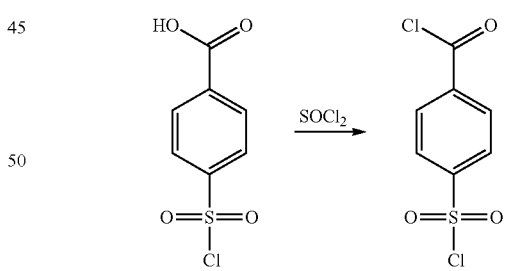

4-(Chlorosulfonyl)benzoic acid (2.5 g, 0.011 mol) was added to a 100 mL single-neck round bottom flask along with a magnetic stir bar. Thionyl chloride (SOCl$_2$, 25 mL) was added and a Vigreux condenser attached. The solution was heated to reflux (75° C.), vigorously stirred over the course of 3 hours and held under a continuous nitrogen flow for the duration of the reaction. After the reaction excess thionyl chloride was removed in-vacuo to provide the chlorinated product as a yellow oil that crystallized upon standing. Spectral data of this compound were consistent with previously reported spectral data in the literature (McGeary, R. P., et al., "An 'inside-out' approach to suramin analogues", Tetrahedron (2009), 65(20), 3990-3997).

Step B: 2-aminoethyl methacrylate attachment

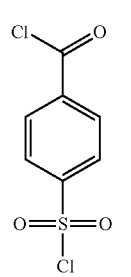
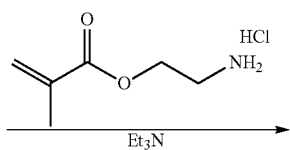

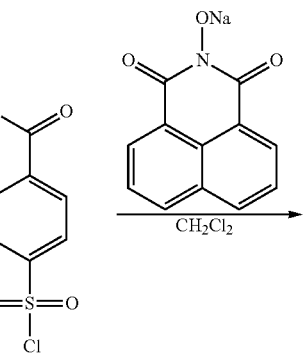

The hydrochloride salt of 2-aminoethyl methacrylate (2.106 g, 0.013 mol, 1.2 eq.) was first neutralized with two equivalents of triethylamine (3.55 mL) in 15 mL of dichloromethane ($CH_2Cl_2$). Neutralization proceeded by rapid stirring in a 20 mL vial for 20 minutes followed by brief (3 min.) sonication. An addition funnel with nitrogen inlet was then attached to the round bottom containing 4-(chlorosulfonyl) benzoyl chloride (2.6 g, 0.01 mol, 1.0 equivalent (eq.)), and dichloromethane (20 mL) was added to the round bottom. The solution of 2-aminoethyl methacrylate was then transferred to the addition funnel and added dropwise. The reaction was stirred at room temperature over the course of 18 hours. The reaction was then diluted with dichloromethane (50 mL), extracted with 1M HCl, then dried using magnesium sulfate ($MgSO_4$) and concentrated by in vacuo. The crude material was purified by column chromatography in dichloromethane followed by elution with 10% (by volume) methanol. $^1$H NMR (300 MHz, $CDCl_3$); delta=8.21-7.95 (m, 4H), 7.15-6.91 (m, 1H), 6.14 (s, 1H), 5.61 (s, 1H), 4.54-4.31 (m, 2H), 3.79 (m, 2H), 1.95 (s, 3H).

Step C: Synthesis of PAG-3

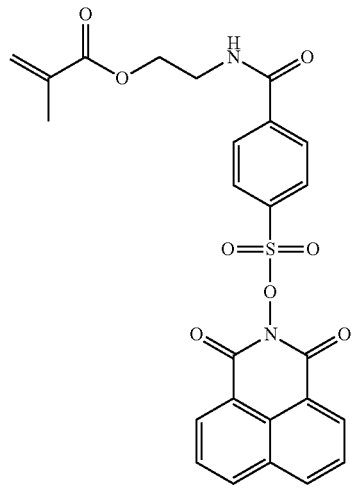

PAG-3

2-(4-(Chlorosulfonyl)benzamido)ethyl methacrylate (120 mg, 0.362 mmol) and N-hydroxynaphthalimide sodium salt (85 mg, 0.361 mmol) were added to a 10 mL round bottom followed by a magnetic stir bar and dichloromethane (3 mL). The reaction was flushed with nitrogen then sealed and stirred at room temperature for the course of 18 hours. The resulting solution was then filtered, diluted with excess dichloromethane, extracted with 1M HCl (100 mL) followed by an extraction with a half-saturated solution of potassium bicarbonate ($K_2CO_3$). The organic phase was then dried with magnesium sulfate ($MgSO_4$) and concentrated in-vacuo to give the target compound as a white powder. $^1$H NMR (300 MHz, $CDCl_3$); delta=8.63 (d, J=7.4 Hz, 2H), 8.30 (d, J=8.3 Hz, 4H), 8.23 (d, J=7.9 Hz, 2H), 8.01 (d, J=8.1 Hz, 2H), 7.82 (d, J=7.6

Hz, 2H), 6.82 (broad s, 1H), 6.18 (s, 1H), 5.65 (s, 1H), 4.44 (s, 2H), 3.79 (m, 2H), 1.98 (s, 3H).

Example 4

Synthesis of PAG monomer 4 (PAG-4). This preparation was performed in three steps.

Step A: Chlorination of 4-(chlorosulfonyl)benzoic acid

The synthesis of 4-(chlorosulfonyl)benzoyl chloride was carried out using the same procedure described for PAG-3 (Example 3).

Step B: 4-aminostyrene attachment

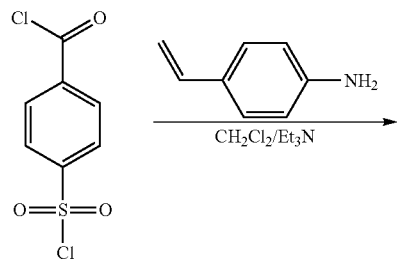

An addition funnel with nitrogen inlet was attached to a 100 mL round bottom vessel containing 4-(chlorosulfonyl) benzoyl chloride (4.0 g, 0.0168 mol) and magnetic stir bar. Dichloromethane (20 mL) was added to the round bottom and rapidly stirred until all material dissolved. Another aliquot of dichloromethane (20 mL) was added to the addition funnel followed by 4-aminostyrene (2.0 mL, 1 eq.) and triethylamine (2.4 mL, 1 eq.). The addition funnel was agitated to ensure the solution was homogenous, after which the solution was added dropwise to the reaction mixture. Additional dichloromethane (10 mL) was used to rinse the addition funnel, and this was added to the reaction. The reaction was stirred at room temperature over the course of 18 hours. Then the reaction solution was diluted further with dichloromethane (50 mL), extracted with 1M HCl, dried using magnesium sulfate (MgSO$_4$) and concentrated in-vacuo. The crude material was then purified by column chromatography in dichloromethane. 1H NMR (300 MHz, CDCl$_3$); delta=8.16 (d, J=8.4 Hz, 2H), 8.09 (d, J=8.4 Hz, 2H), 7.89 (s, 1H), 7.61 (d, J=8.1 Hz, 2H), 7.44 (d, J=8.1 Hz, 2H), 6.71 (dd, J=17.7, 10.8 Hz, 1H), 5.74 (d, J=17.7 Hz, 1H), 5.26 (d, J=10.8 Hz, 1H).

Step C: Synthesis of PAG-4

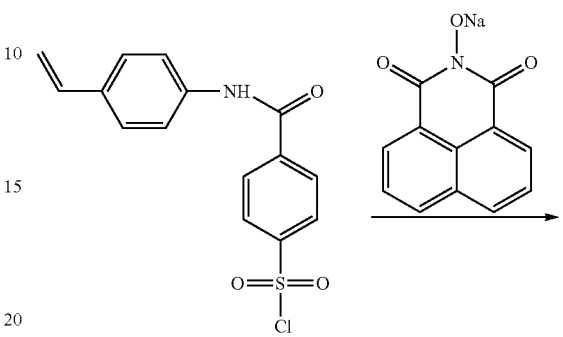

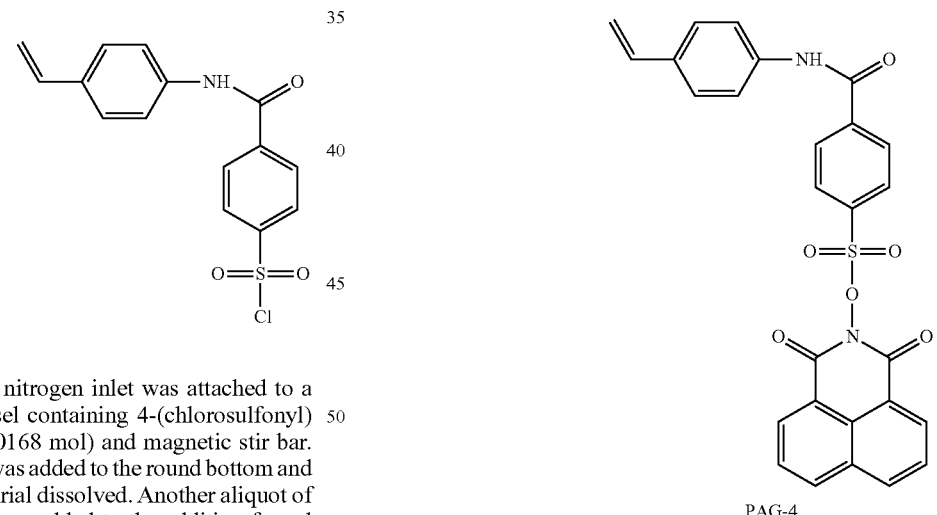

PAG-4

4-((4-Vinylphenyl)carbamoyl)benzenesulfonyl chloride (370 mg, 1.15 mmol), N-hydroxynaphthalimide sodium salt (270 mg, 1.15 mmol) and magnetic stir bar were added to a 20 mL round bottom flask. Dichloromethane (10 mL) was then added, the reaction was flushed with nitrogen and sealed, and the reaction mixture was stirred over the course of 18 hours. The resulting reaction was then filtered and the solvent removed in-vacuo to provide the target compound as a white powder. $^1$H NMR (300 MHz, CDCl3, 10% MeCN-d$_3$); delta=8.51 (d, J=7.3 Hz, 2H), 8.24 (d, J=8.2 Hz, 2H), 8.12 (d, J=7.8 Hz, 2H), 8.05 (d, J=7.8 Hz, 2H), 7.73 (t, J=7.7 Hz, 2H), 7.59 (d, J=8.1 Hz, 2H), 7.33 (d, J=8.2 Hz, 2H), 6.60 (dd, J=17.4, 11.0 Hz, 1H), 5.62 (d, J=17.6 Hz, 1H), 5.12 (d, J=11.0 Hz, 1H).

Example 5

Synthesis of PAG monomer 5 (PAG-5). This preparation was performed in three steps.

Step A: chlorination of 2,3,5,6-tetrafluoro-4-sulfobenzoic acid

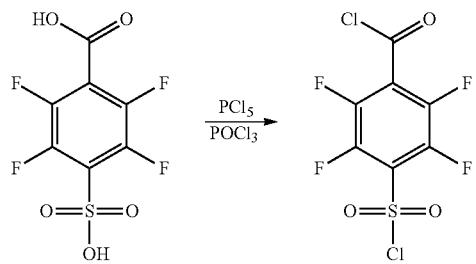

2,3,5,6-Tetrafluoro-4-sulfobenzoic acid (4.28 g, 0.0156 mol) was added to a 100 mL round bottom flask along with a magnetic stir bar, followed by phosphorous pentachloride (PCl$_5$, 8.14 g, 0.039 mol, 2.5 eq.) and phosphorous(V) oxychloride (POCl$_3$, 2.14 mL, 0.0234 mol, 1.5 eq.). The reaction mixture was then quickly attached to a Vigreux reflux condenser with nitrogen inlet. The reaction was purged with nitrogen then heated to 90° C. for a period of 2 hours. The phosphorous salts were precipitated from the reaction mixture using dry hexanes (100 mL). The resulting cloudy white solution was filtered under nitrogen and concentrated in vacuo to give 4-(chlorosulfonyl)-2,3,5,6-tetrafluorobenzoyl chloride as a light yellow oil that crystallized upon standing. Analytical spectral data for this compound were consistent with previously reported data in the literature (Fielding, H. C., Shirley, I. M., "Synthesis and reactions of 4-sulpho-2,3,5,6,-tetrafluorobenzoic acid", Journal of Fluorine Chemistry (1992), 59, 15-31).

Step B: 2-aminoethyl methacrylate attachment

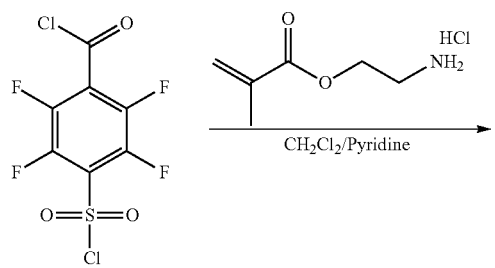

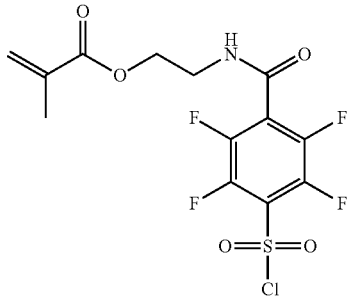

In a 20 mL vial, 2-aminoethyl methacrylate hydrochloride (0.586 g, 3.53 mmol, 1.0 eq.) was neutralized with pyridine (0.571 mL, 2 eq.) in dichloromethane (CH$_2$Cl$_2$, 15 mL). Neutralization proceeded by rapidly stirring the mixture for 20 minutes followed by sonication for 3 minutes. The solution was then set aside. Dichloromethane (10 mL) was added to a round bottom containing a magnetic stir bar and 4-(chlorosulfonyl)-2,3,5,6-tetrafluorobenzoyl chloride (1.1 g, 3.53 mmol). The solution was rapidly stirred under nitrogen until all material dissolved. An addition funnel charged with the neutralized 2-aminoethyl methacrylate solution and having a nitrogen inlet was attached to the reaction vessel. The round bottom flask was then cooled to 0° C. in an ice bath followed by the dropwise addition of neutralized reagent. Dichloromethane (5 mL) was used to rinse the addition funnel and this solution was added to the reaction. The reaction was stirred at room temperature over the course of 18 hours, after which the reaction was diluted with dichloromethane (50 mL), extracted with 1M HCl, dried using magnesium sulfate (MgSO$_4$) and concentrated in vacuo. The crude product was then purified by column chromatography in dichloromethane and 1.5% (by volume) methanol. $^1$H NMR (400 MHz, CD$_2$Cl$_2$); delta=6.56 (s, 1H), 6.12 (s, 1H), 5.63 (s, 1H), 4.35 (t, J=5.5 Hz, 2H), 3.79 (q, J=5.6 Hz, 2H), 1.93 (s, 3H). $^{19}$F NMR (376 MHz, CD$_2$Cl$_2$); delta=−131.72 to −132.13 (m), −135.17 to −135.29 (m, 2F).

Step C: Synthesis of PAG-5

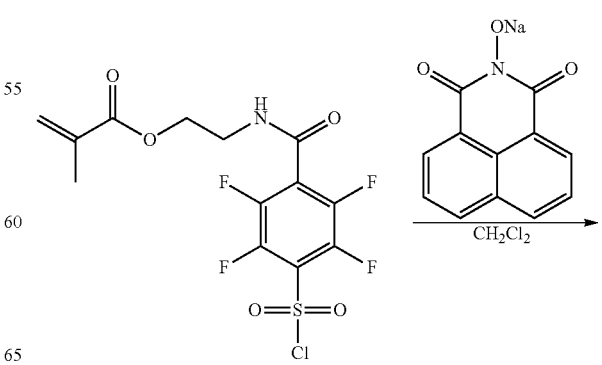

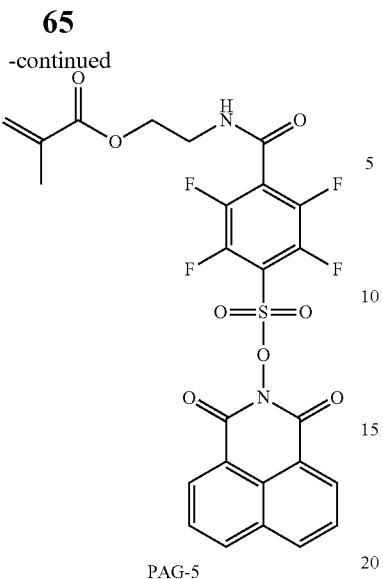

PAG-5

2-(4-(chlorosulfonyl)-2,3,5,6-tetrafluorobenzamido)ethyl methacrylate (670 mg, 1.66 mmol) and N-hydroxynaphthalimide (354 mg, 1.66 mmol) were added to a 50 mL round bottom followed by a magnetic stir bar and dichloromethane (10 mL). The reaction was flushed with nitrogen then sealed and stirred at room temperature for the course of 18 hours. The reaction was then further diluted with dichloromethane (50 mL), extracted with 1M HCl, and dried using magnesium sulfate (MgSO$_4$). The solvent was removed in vacuo to give the target compound as a white powder. $^1$H NMR (400 MHz, CD$_2$Cl$_2$); delta=8.48 (d, J=7.3 Hz, 2H), 8.34 (d, J=8.2 Hz, 2H), 7.77 (t, J=7.8 Hz, 2H), 7.39 (s, 1H), 6.07 (s, 1H), 5.57 (s, 1H), 4.23 (t, J=5.3 Hz, 2H), 3.67 (q, J=5.5 Hz, 2H), 1.88 (s, 3H). $^{19}$F NMR (376 MHz, CD$_2$Cl$_2$); delta=−134.08 to −134.58 (m, 2F), −139.41 to −139.94 (m, 2F).

Example 6

Synthesis of PAG monomer 6 (PAG-6). This preparation was performed in three steps.

Step A: chlorination of 2,3,5,6-tetrafluoro-4-sulfobenzoic acid

The synthesis of 4-(chlorosulfonyl)-2,3,5,6-tetrafluorobenzoyl chloride was carried out using the same procedure described for PAG-5 (Example 5).

Step B: 4-aminostyrene attachment

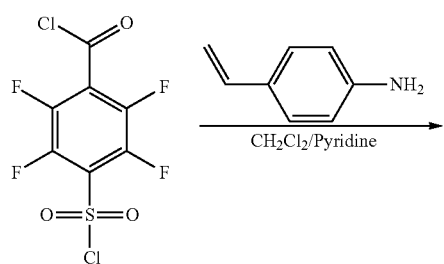

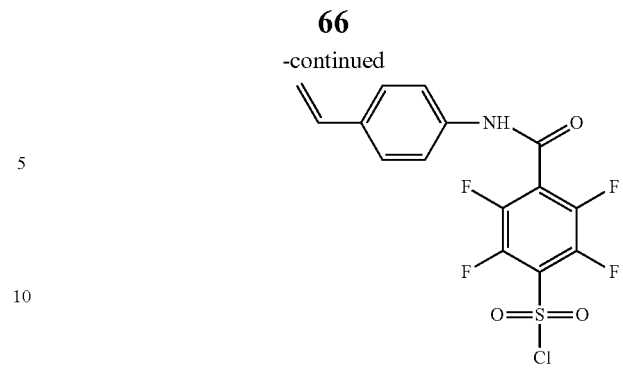

To a round bottom flask containing a magnetic stir bar was added dichloromethane (20 mL) and 4-(chlorosulfonyl)-2,3,5,6-tetrafluorobenzoyl chloride (2.00 g, 6.43 mmol). The solution was rapidly stirred under nitrogen until all material dissolved. An addition funnel with nitrogen inlet was then attached and dichloromethane (20 mL) was added followed by 4-aminostyrene (0.75 mL, 1 eq.) and pyridine (0.52 mL, 1 eq.). The addition funnel was agitated to ensure solution was homogenous. The round bottom flask was then cooled to 0° C. in an ice bath followed by the dropwise addition of reagents to the stirring solution of 4-(chlorosulfonyl)-2,3,5,6-tetrafluorobenzoyl chloride. After addition, dichloromethane (10 mL) was used to rinse the addition funnel, and this solution was added to the reaction. The reaction was stirred at room temperature over the course of 18 hours. The reaction was then further diluted with dichloromethane (50 mL), extracted with 1M HCl, dried using magnesium sulfate (MgSO$_4$), and concentrated in vacuo. The crude material was purified by column chromatography in dichloromethane. $^1$H NMR (400 MHz, CDCl$_3$); delta=7.50 (d, J=8.3 Hz, 1H), 7.31 (d, J=8.5 Hz, 1H), 7.24 (d, J=8.4 Hz, 1H), 7.09 (d, J=8.4 Hz, 1H), 6.57 (ddd, J=20.6, 17.6, 10.9 Hz, 1H), 5.60 (dd, J=17.6, 14.2 Hz, 1H), 5.13 (dd, J=10.9, 2.4 Hz, 1H). $^{19}$F NMR (376 MHz, CDCl$_3$); delta=−132.38 to −132.67 (m, 2F), −134.49 to −135.22 (m, 2F).

Step C: Synthesis of PAG-6

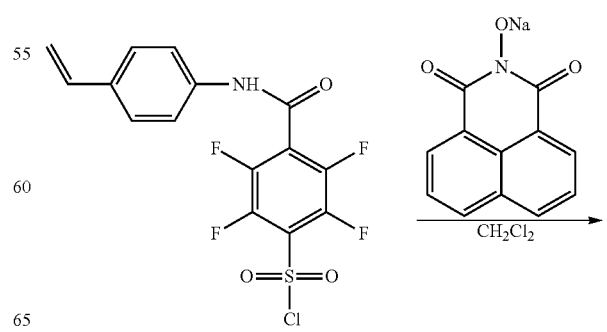

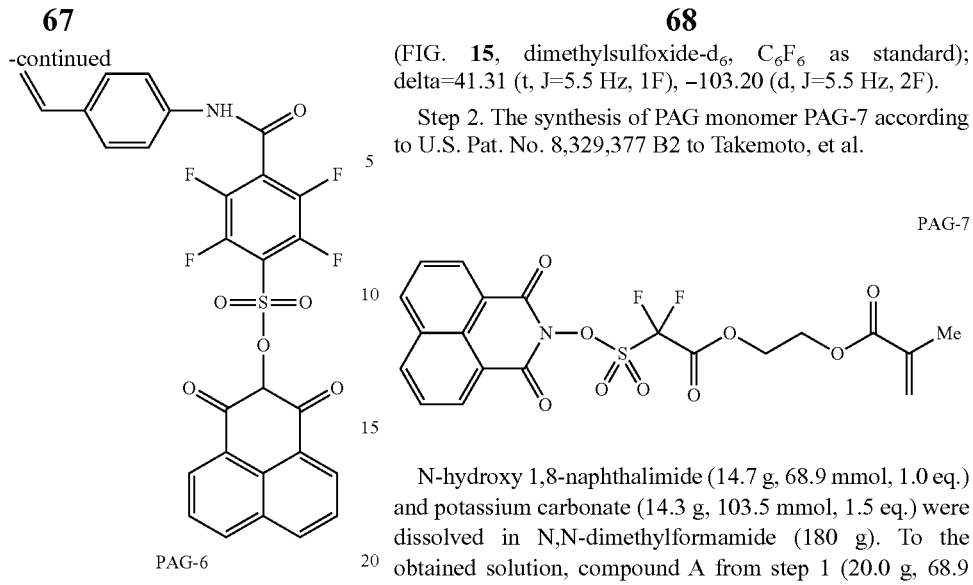

PAG-6

A 10 mL round bottom flask containing a magnetic stir bar was charged with 2,3,5,6-tetrafluoro-4-((4-vinylphenyl)carbamoyl)benzenesulfonyl chloride (94 mg, 0.239 mmol) and N-hydroxynaphthalimide sodium salt (56.1 mg, 0.239 mmol). Dichloromethane (3 mL) was then added and the reaction flushed with nitrogen then sealed and stirred over the course of 18 hours. The resulting reaction was then filtered and concentrated in vacuo to provide the target compound as a white powder. $^1$H NMR (400 MHz, $(CD_3)_2CO$); delta=9.02 (s, 1H), 8.53 (d, J=7.3 Hz, 2H), 8.33 (d, J=8.2 Hz, 2H), 7.79 (t, J=7.8 Hz, 2H), 7.59 (d, J=8.5 Hz, 2H), 7.40 (d, J=8.5 Hz, 2H), 6.67 (dd, J=17.6, 10.9 Hz, 1H), 5.70 (d, J=17.6 Hz, 1H), 5.19 (d, J=10.9 Hz, 1H). $^{19}$F NMR (376 MHz, $(CD_3)_2CO$); delta=−133.57 to −133.87 (m, 2F), −138.46 to −138.75 (m, 2F).

Synthesis of PAG Monomer PAG-7 (Comparative)

Step 1. The synthesis of compound A according to U.S. Pat. No. 8,329,377 B2 to Takemoto, et al.

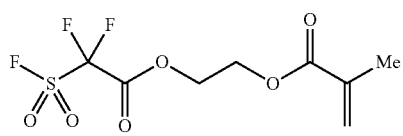

A

Figure 14:
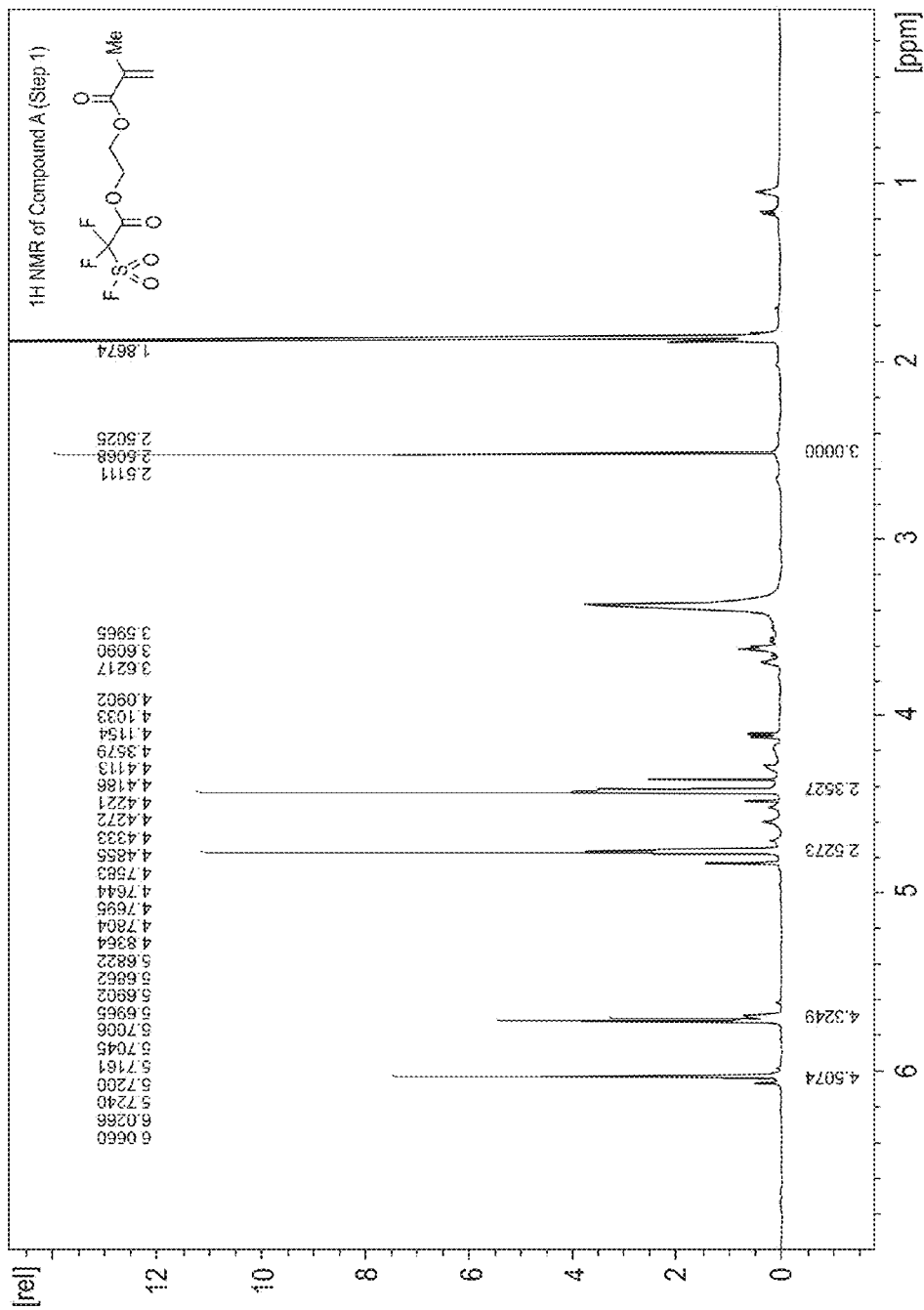
FIG. 14 is a $^1$H-NMR of compound A in the preparation of PAG-7.
Figure 15:
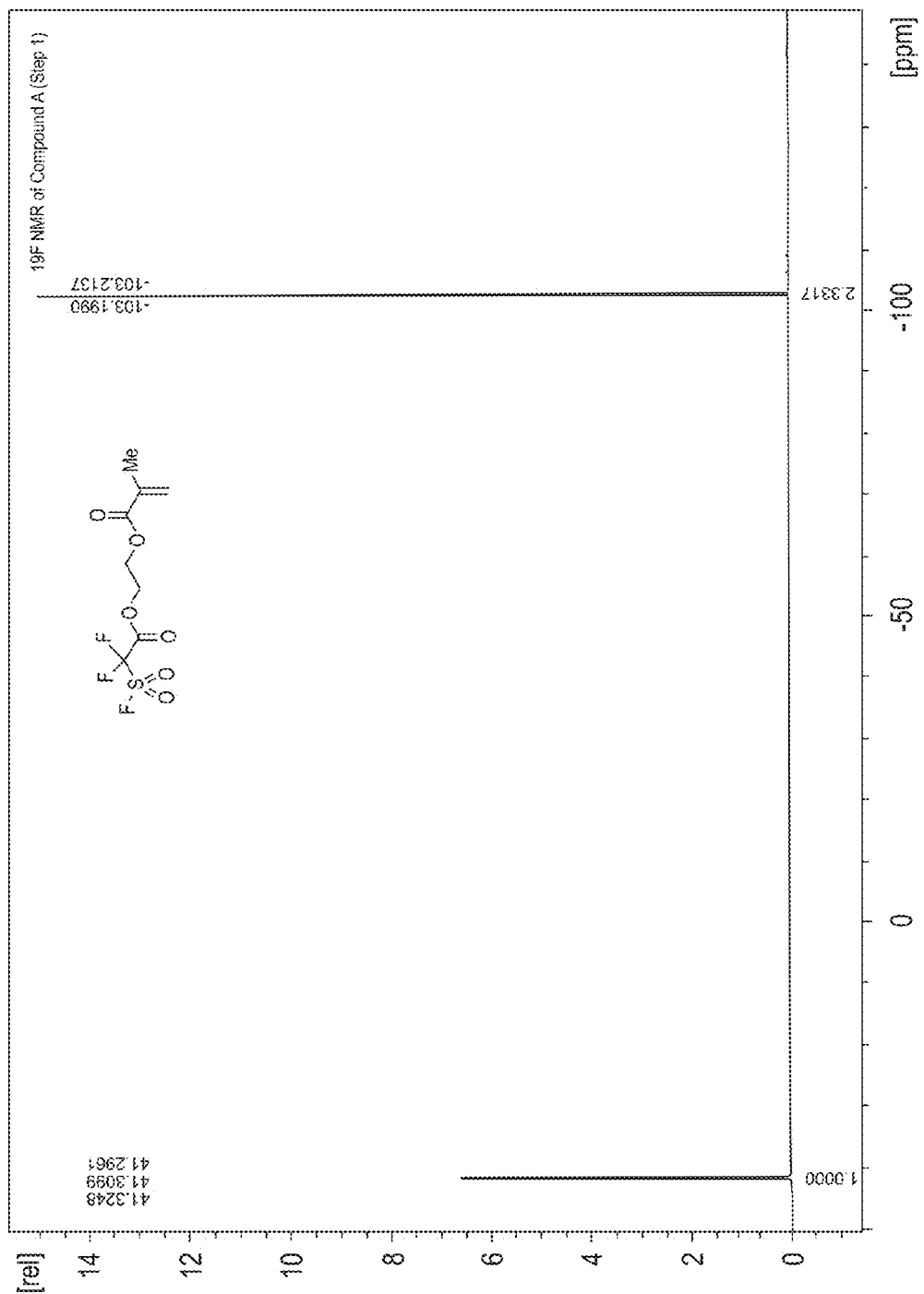
FIG. 15 is a $^{19}$F-NMR of compound A in the preparation of PAG-7.

Difluoro(fluorosulfonyl)acetic acid (24.65 g, 138.4 mmol, 1.2 eq.) and 2-hydroxyethyl methacrylate (15 g, 115.3 mmol, 1.0 eq.) were dissolved in dichloroethane (150 g). To the obtained solution, a small amount of p-methoxyphenol (123 mg, 0.5 wt % of difluoro(fluorosulfonyl)acetic acid) was added as a polymerization inhibitor followed by concentrated sulfuric acid (0.225 g, 2.3 mmol, 0.02 eq.). The resultant mixture was refluxed at 87° C. for 7 hours and cooled to room temperature. Ion-exchanged water (150 g) and chloroform (100 g) were added to the mixture to conduct an extraction. The obtained organic layer was washed three times with ion-exchanged water and then concentrated under reduced pressure to obtain compound A (23.2 g, 79.9 mmol, 69.3% crude yield). $^1$H-NMR (FIG. 14, 400 MHz, dimethylsulfoxide-d$_6$); delta=1.87 (s, 3H), 4.42 (t, J=4.4 Hz, 2H), 4.76 (t, J=4.4 Hz, 2H), 5.72 (t, J=1.6 Hz, 1H), 6.03 (s, 1H). $^{19}$F-NMR (FIG. 15, dimethylsulfoxide-d$_6$, $C_6F_6$ as standard); delta=41.31 (t, J=5.5 Hz, 1F), −103.20 (d, J=5.5 Hz, 2F).

Step 2. The synthesis of PAG monomer PAG-7 according to U.S. Pat. No. 8,329,377 B2 to Takemoto, et al.

PAG-7

Figure 16:
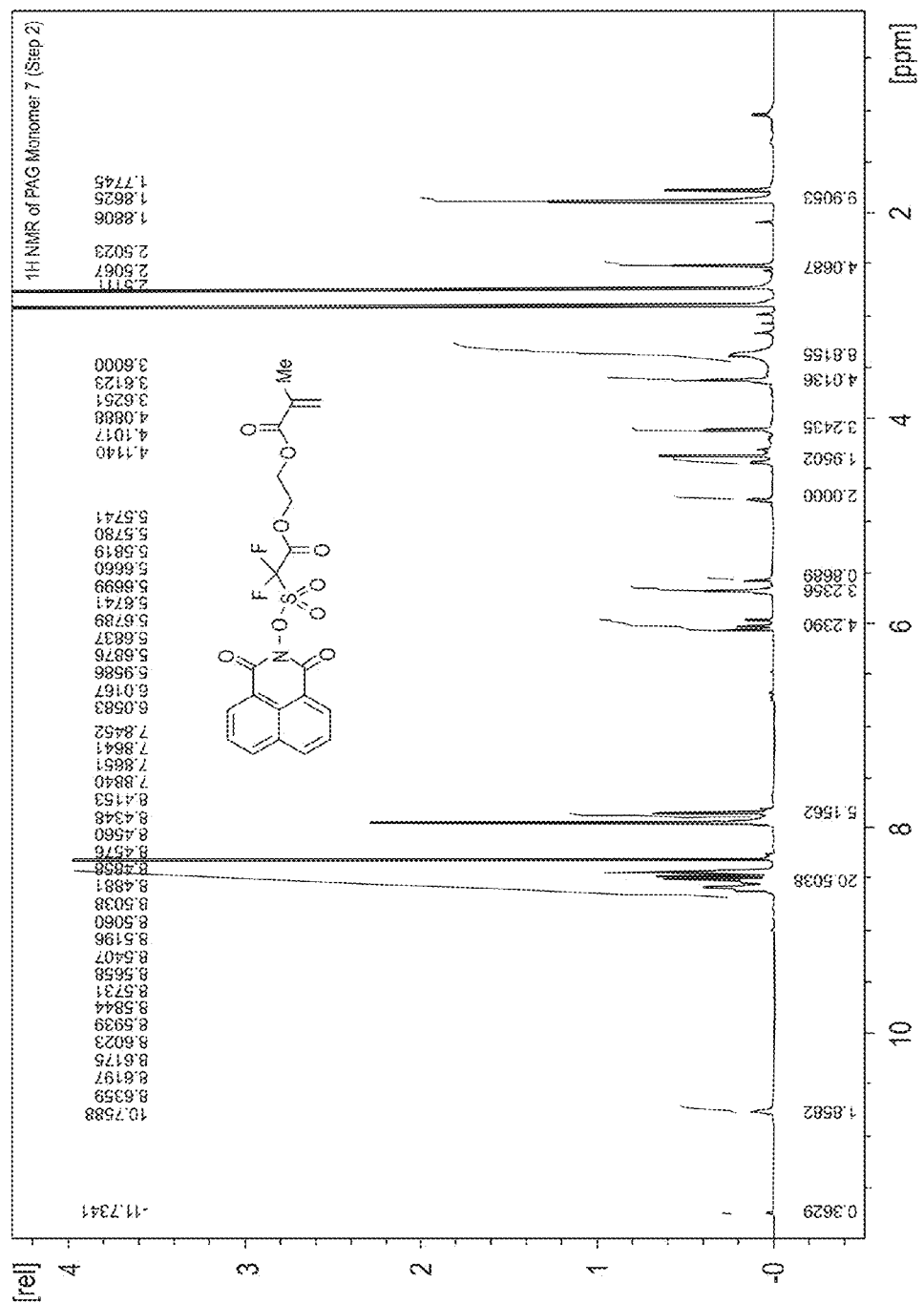
FIG. 16 is a $^1$H-NMR of crude PAG-7.
Figure 17:
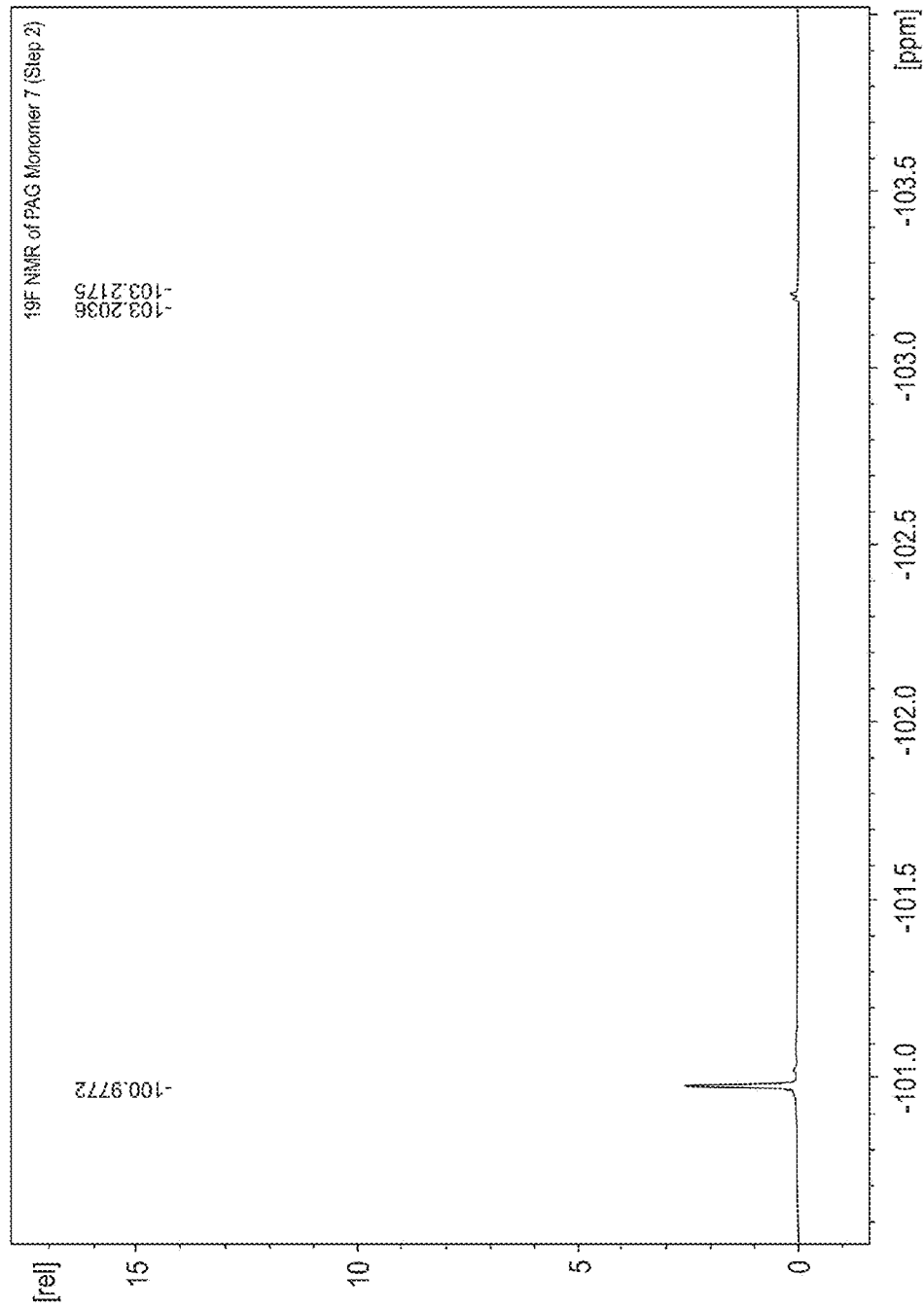
FIG. 17 is a $^{19}$F-NMR of crude PAG-7.

N-hydroxy 1,8-naphthalimide (14.7 g, 68.9 mmol, 1.0 eq.) and potassium carbonate (14.3 g, 103.5 mmol, 1.5 eq.) were dissolved in N,N-dimethylformamide (180 g). To the obtained solution, compound A from step 1 (20.0 g, 68.9 mmol, 1.0 eq.) was added followed by a small amount of pyridine (200 mg, 1.0 wt % of compound A) and a small amount of p-methoxyphenol (100 mg, 0.5 wt % of compound A) as a polymerization inhibitor. The resultant mixture was stirred for 2 hours at 30° C. The obtained reaction mixture was filtrated to separate the insoluble matters. The insoluble matters were washed with chloroform (300 g). The filtrate was diluted with 1% aqueous oxalic acid solution (500 g) and chloroform (300 g) to conduct an extraction. The obtained organic layer was washed with ion-exchanged water five times and the solution was dried over $Na_2SO_4$ and then concentrated to obtain crude PAG-7 (9.9 g, 29.7%). The sample included a lot of impurities (FIG. 16, $^1$H NMR; FIG. 17, $^{19}$F NMR).

Step 3. Purification of PAG-7. Chloroform (100 ml) was added to crude PAG-7 (4.54 g) and the mixture was stirred for 2 hours at room temperature. The mixture was filtered to separate insoluble material. The filtrate was washed with saturated $NaHCO_3$ (25 ml) three times and brine (25 ml) two times and then the solution was dried over $MgSO_4$. Chloroform was removed by an evaporator and ethyl acetate (30 ml) and hexane (70 ml) were added to the residue. The insoluble material were filtrated and the filtrate was concentrated. The residue was washed by hexane (50 ml) three times. The obtained crude PAG-7 was purified by short column chromatography followed by hexane (50 ml) washing two times to obtain PAG-7 (0.47 g). Unfortunately, the final compound included an impurity which was not able to be identified. It was estimated that the targeted compound was 85 wt % pure. Yield: 2.6%. 9.9 (crude)/4.54×0.47×0.85 (wt %)=0.87 g. 0.87/[483.40 (MW)×68.9 (mmol)]×100=2.6%.

Figure 18:
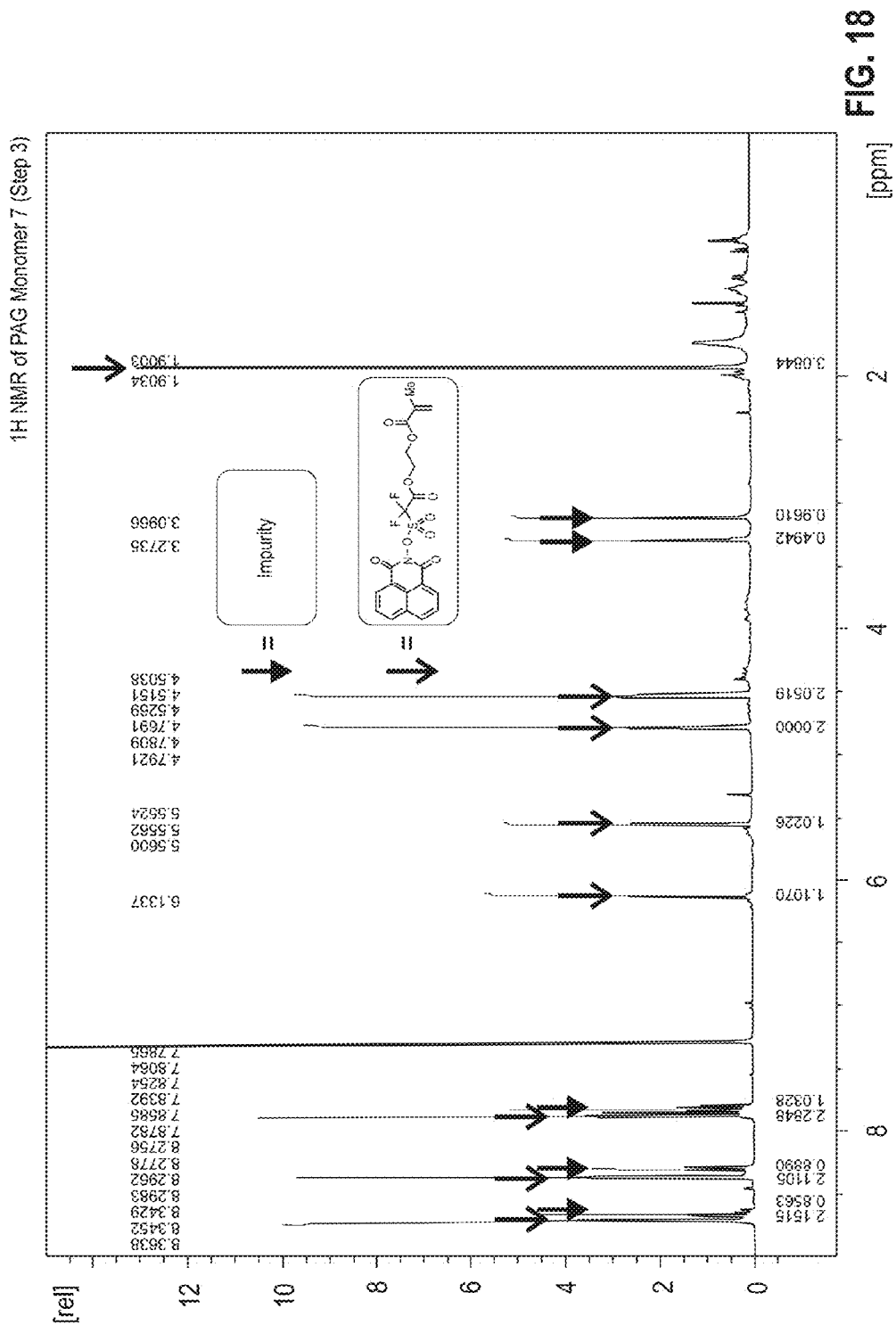
FIG. 18 is a $^1$H-NMR of PAG-7 of about 85% purity. Angled arrowhead peaks correspond to PAG-7. Solid arrowhead peaks correspond to an impurity.
Figure 19:
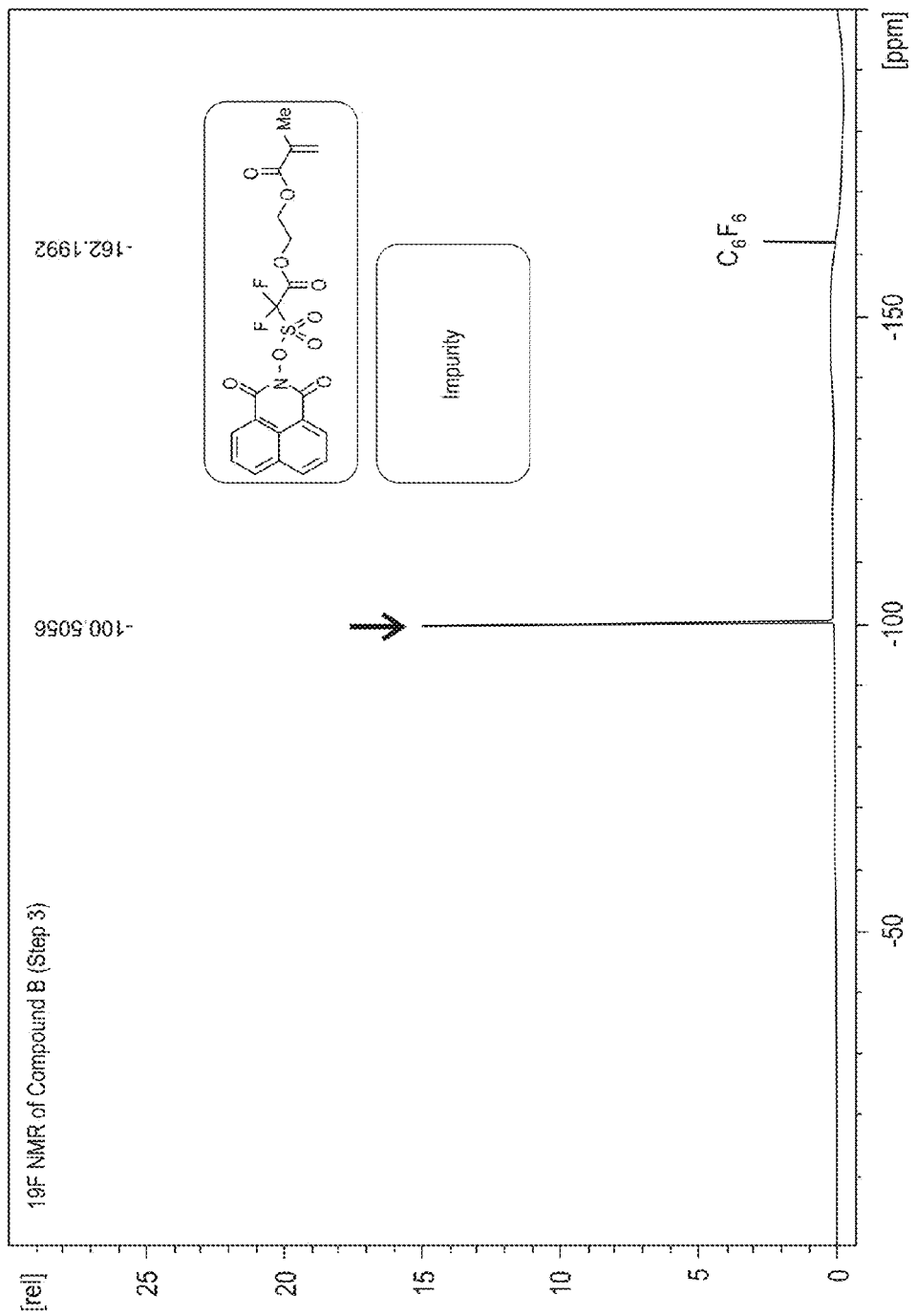
FIG. 19 is a $^{19}$F-NMR of PAG-7 of about 85% purity.
Figure 20:
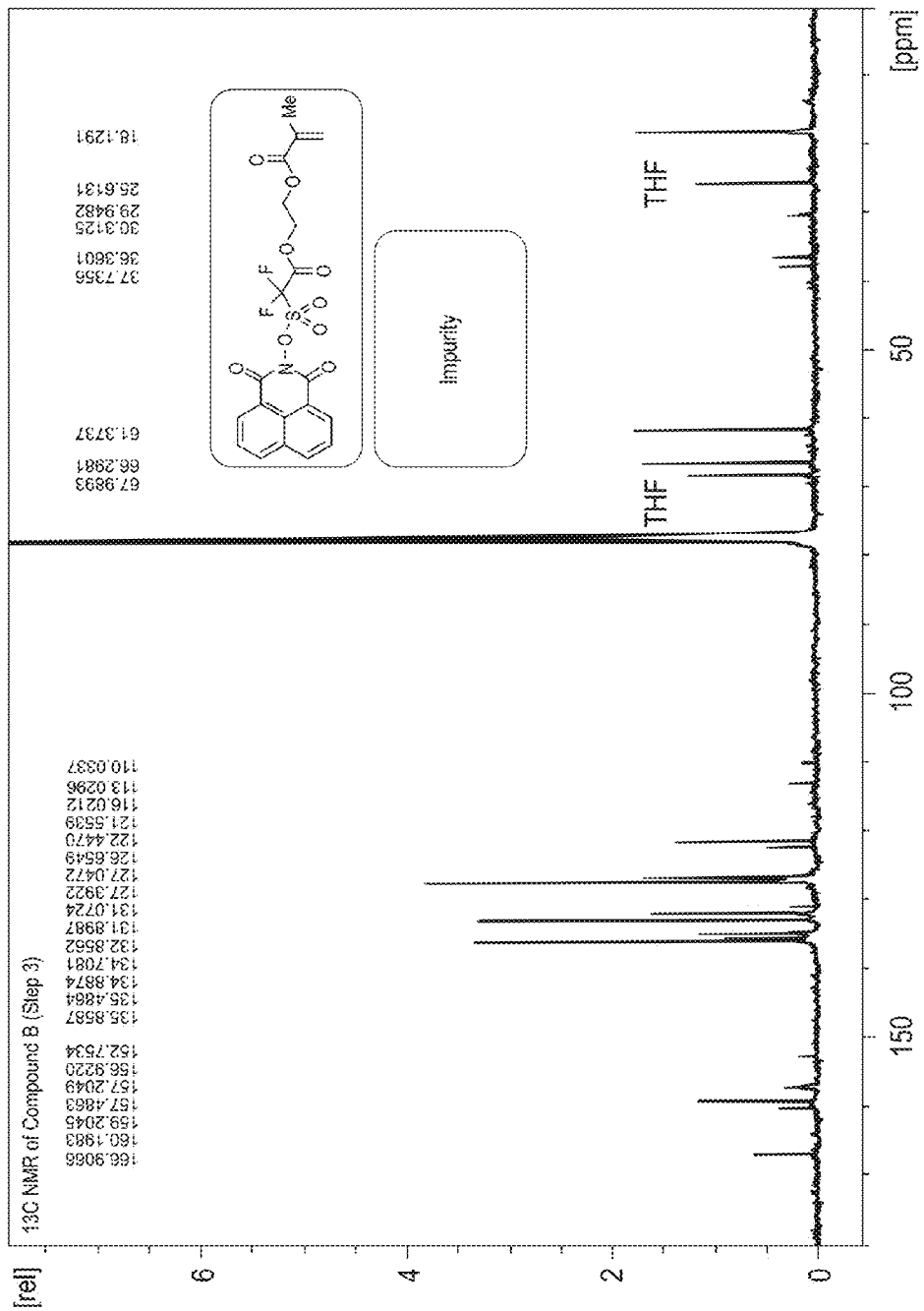
FIG. 20 is a $^{13}$C-NMR of PAG-7 of about 85% purity.

PAG-7 spectra. $^1$H-NMR (FIG. 18, angled arrowhead peaks, (400 MHz, $CDCl_3$); delta=1.90 (t, J=1.0 Hz, 3H), 4.52 (t, J=4.6 Hz, 2H), 4.78 (t, J=4.6 Hz, 2H), 5.56 (t, J=1.5 Hz, 1H), 6.13 (s, 1H), 7.86 (dd, J=7.7, 7.9 Hz, 2H), 8.35 (dd, J=0.9, 8.3 Hz, 2H), 8.70 (dd, J=1.0, 7.4 Hz, 2H). $^{19}$F-NMR (FIG. 19, thin arrow peaks, 376 MHz, $CDCl_3$, $C_6F_6$ as standard); delta=−100.51 (s, 2F). $^{13}$C-NMR (FIG. 20, thin arrow peaks, 100 MHz, $CDCl_3$); delta=18.1, 61.4, 66.3, 113.0 (t, J=299.4 Hz), 121.6, 126.7, 127.0, 127.4, 131.9, 132.9, 134.9, 135.9, 157.2 (t, J=28.2 Hz), 159.2, 166.9.

PAG-7 impurity. ¹H-NMR (FIG. 18, solid arrowhead peaks, 400 MHz, CDCl₃); delta=3.10 (s, 3H), 3.27 (s, 3H), 7.81 (dd, J=7.6, 8.0 Hz, 2H), 8.29 (dd, J=0.9, 8.2 Hz, 2H), 8.66 (dd, J=1.0, 7.3 Hz, 2H).
The PAG monomers are summarized below.
PAG-1
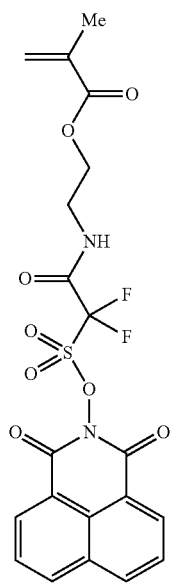
PAG-2
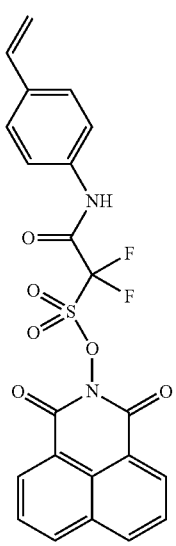
PAG-3
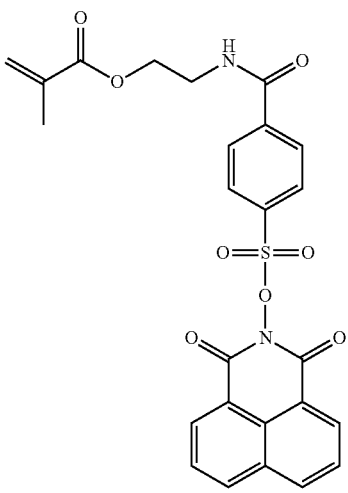
PAG-4
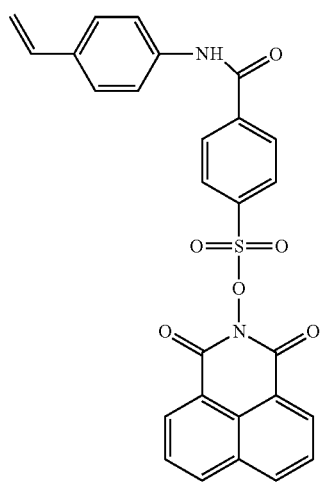
PAG-5
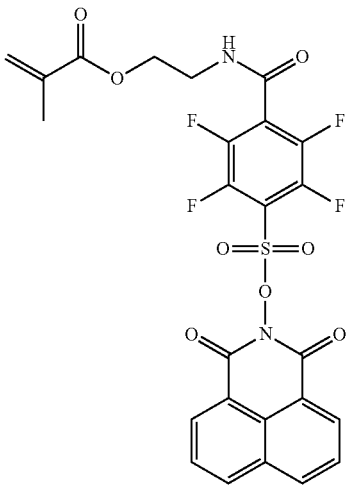

-continued

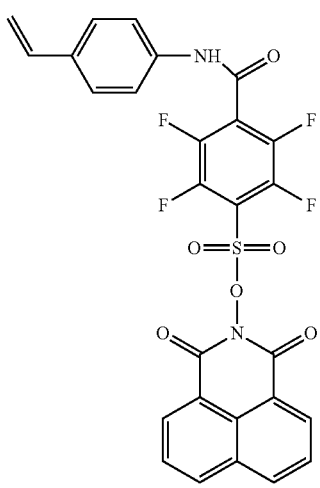

PAG-6

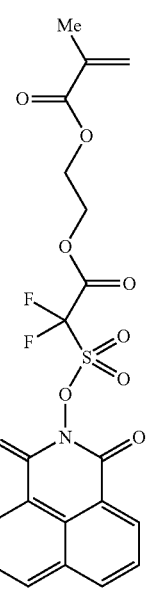

PAG-7 (comp)

PAG Polymer Synthesis

In addition to the PAG monomers, the following polymerizable vinyl co-monomers were utilized in the synthesis of PAG-bound polymers. NBHFAMA is a mixture of structural isomers in which the butenone fragment is linked to carbon 1 or carbon 6 of the norbornyl ring, as shown below.

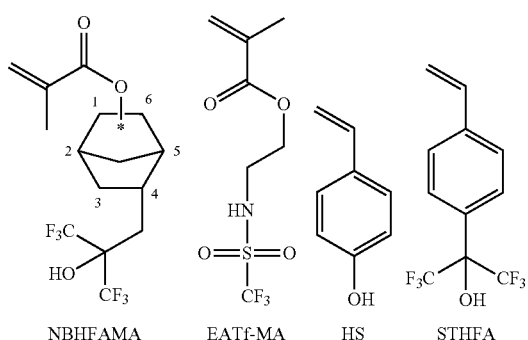

NBHFAMA  EATf-MA  HS  STHFA

-continued

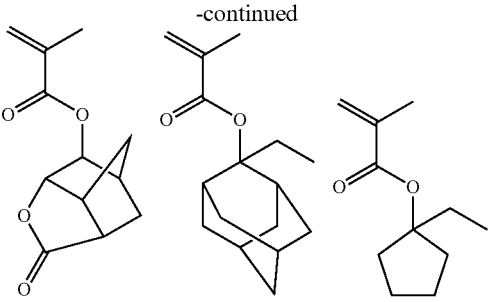

NLM  EAdMA  ECPMA

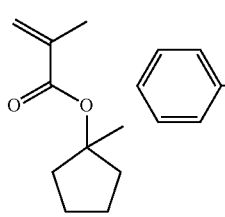

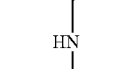

MCPMA  TPS-UMA

Examples 7 to 20

The following general procedure was used to prepare PAG polymers P-1 to P-13 from non-ionic PAG monomers by free radical polymerization. A 20 wt % (weight percent) solution of the desired monomers, 4 mole % of azobisobutyronitrile (AIBN) and 3 mol % of dodecanethiol in tetrahydrofuran (THF) was degassed using four vacuum/nitrogen purges. The mixture was then heated at 70° C. in an oil bath for about 18 hours. The reaction mixture was cooled to room temperature and added to a 20-fold excess of stirred hexanes. The precipitated polymer was collected by filtration, washed with several portions of hexanes, and dried in a vacuum oven at 50° C. to constant weight. The yield typically was about 60%. The compositional analysis of the polymers by Inverse Gated $^{13}$C NMR indicated that the polymer compositions were similar to the feed ratio.

The preparation of PAG polymer P-1 is representative. NBHFAMA (1.98 grams, 0.0055 mole), ECPMA (0.73 grams, 0.004 mole), PAG-1 (0.24 grams, 0.0005 mole) and 11.8 grams of tetrahydrofuran (THF) were placed in a round bottom flask equipped with a condenser and a nitrogen inlet. To this solution, 2,2'-azobisisobutyronitrile (AIBN) (0.066 gram, 0.0004 mole) and 1-dodecanethiol (0.060 gram, 0.0003 mole) were added and stirred until dissolved. Then, the solution was degassed using four vacuum/nitrogen purges. The solution was then heated at 70° C. in an oil bath for 18 hours.

Afterwards, the solution was added drop-wise into hexanes (350 ml). The precipitated polymer was filtered through a medium frit funnel, washed with 100 ml hexanes, and dried under suction. This polymer was then dried in a vacuum oven at 60° C. Yield: 1.74 grams. Molecular weight: Mw 8646; Mn 6370; polydispersity (PDI): 1.36; Tg: 134.6° C.

PAG polymer P-14 was prepared using ionic PAG monomer TPS-UMA in methyl ethyl ketone according to the procedure described in US20130260313 A1.

Preparation of PAG Polymer P-15 (Comparative) Using PAG-7.

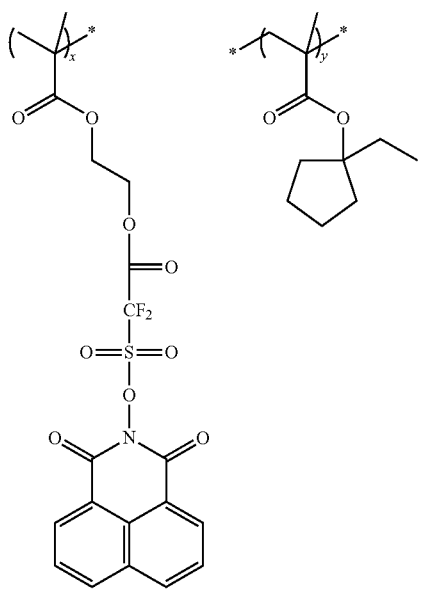

-continued x:y:z = 5:40:55

NBHFAMA (1.98 grams, 0.0055 mole), ECPMA (0.73 grams, 0.004 mole), PAG-7 (0.28 g 85% pure, 0.0005 mole) and tetrahydrofuran (THF, 11.8 grams) were placed in a round bottom flask equipped with a condenser and a nitrogen inlet. To this solution, 2,2'-azobisisobutyronitrile (AIBN) (0.066 gram, 0.0004 mole) and 1-dodecanethiol (0.060 gram, 0.0003 mole) were added and stirred until dissolved. Then, the solution was degassed using four vacuum/nitrogen purges. The solution was then heated at 70° C. in an oil bath for 18 hours. Afterwards, the solution was added drop wise into hexanes (350 ml). The precipitated polymer was filtered through a medium frit funnel, washed with 100 ml hexanes, and dried under suction. This polymer was then dried in a vacuum oven at 50° C. Yield: 1.75 grams. Mw 10125; Mn 7465; polydispersity: 1.36; and Tg: 129.8° C.

The preparations and properties of PAG polymers P-1 to P-15 are summarized in Table 2. Examples 7-11 and 13-21 utilized 3 monomers denoted by M1, M2, and M3; Example 12 further utilized a fourth monomer denoted by M4. The molar feed ratios of M1, M2, M3, and M4 are also listed (mol %=mole percent). PDI refers to polydispersity index of the polymer. $T_d$ is the decomposition temperature by thermogravimetric analysis.

TABLE 2

| Example | PAG Polymer | M1 | M2 | M3 | M4 | Monomer Feed (mol %) M1/M2/M3/M4 | Mn | Mw | PDI | $T_d$ (° C.) |
|---|---|---|---|---|---|---|---|---|---|---|
| 7 | P-1 | PAG-1 | ECPMA | NBHFAMA | | 5/40/55/0 | 6370 | 8646 | 1.36 | 158 |
| 8 | P-2 | PAG-1 | ECPMA | NBHFAMA | | 10/40/50/0 | 5075 | 7353 | 1.45 | 154 |
| 9 | P-3 | PAG-1 | ECPMA | NBHFAMA | | 15/40/45/0 | 5187 | 7594 | 1.46 | 155 |
| 10 | P-4 | PAG-2 | ECPMA | NBHFAMA | | 5/40/55/0 | 5461 | 7765 | 1.42 | 160 |
| 11 | P-5 | PAG-1 | ECPMA | HS | | 5/40/55/0 | 2758 | 5071 | 1.84 | 109 |
| 12 | P-6 | PAG-1 | ECPMA | NBHFAMA | NLM | 5/40/15/40 | 4892 | 7824 | 1.60 | 184 |
| 13 | P-7 | PAG-1 | MCPMA | NBHFAMA | | 5/40/55/0 | 8037 | 10876 | 1.35 | 170 |
| 14 | P-8 | PAG-1 | EADMA | STHFA | | 5/45/50/0 | 4391 | 7023 | 1.60 | 135 |
| 15 | P-9 | PAG-1 | ECPMA | EATf-MA | | 5/40/55/0 | 1342 | 2120 | 1.58 | 166 |
| 16 | P-10 | PAG-3 | ECPMA | NBHFAMA | | 5/40/55/0 | 2797 | 3682 | 1.32 | |
| 17 | P-11 | PAG-4 | ECPMA | NBHFAMA | | 5/40/55/0 | 6084 | 8781 | 1.44 | 200 |
| 18 | P-12 | PAG-5 | ECPMA | NBHFAMA | | 5/40/55/0 | 7030 | 9567 | 1.36 | 160 |
| 19 | P-13 | PAG-6 | ECPMA | NBHFAMA | | 5/40/55/0 | 6553 | 9569 | 1.46 | 160 |
| 20 (comp) | P-14 | TPS-UMA | ECPMA | NBHFAMA | | 5/40/55/0 | 2053 | 2792 | 2.60 | 174 |
| 21 (Comp) | P-15 | PAG-7 | ECPMA | NBHFAMA | | 5/40/55/0 | 7465 | 10125 | 1.36 | 140 |

The repeating unit structures of PAG polymers P-1 to P-15 are listed in Table 3 below. It should be understood that the P-1 to P-15 are random copolymers comprising the repeating units shown in Table 3. End groups of the PAG polymers are not listed. Starred bonds of the repeating units indicate attachment points, not methyl groups. Subscripts x, y, z, and z' indicate mole percent (mol %) of the corresponding parenthesized repeating unit of the PAG polymer (i.e., not a block polymer chain).

TABLE 3

| Example | PAG Polymer | Repeating Units (mole ratio)[a] |
|---|---|---|
| 7 | P-1 | 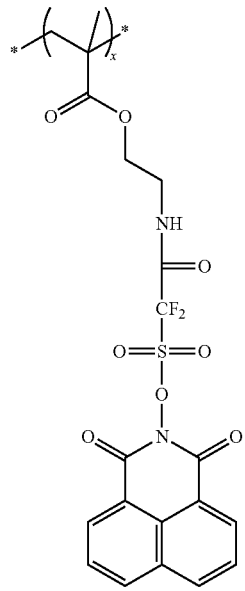 x/y/z = 5/40/55 |
| 8 | P-2 | 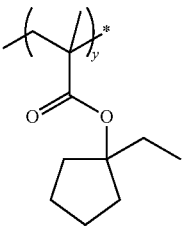 x/y/z = 10/40/50 |

TABLE 3-continued
| Example | PAG Polymer | Repeating Units (mole ratio)[a] |
|---|---|---|
| 9 | P-3 | 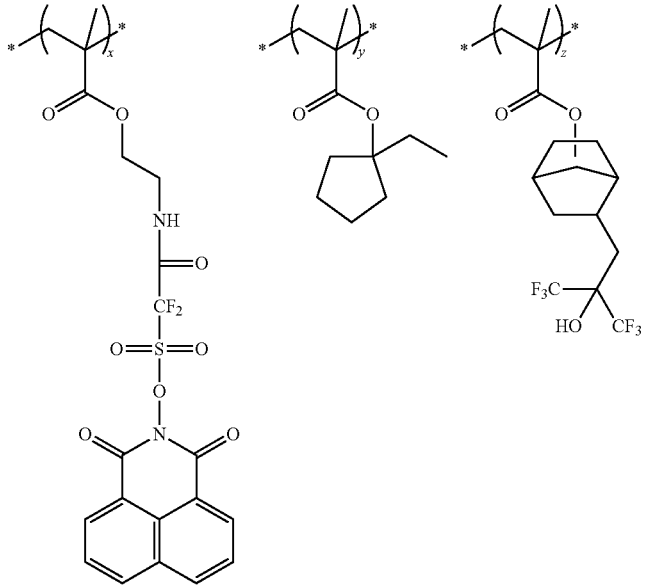 x/y/z = 15/40/45 |
| 10 | P-4 | 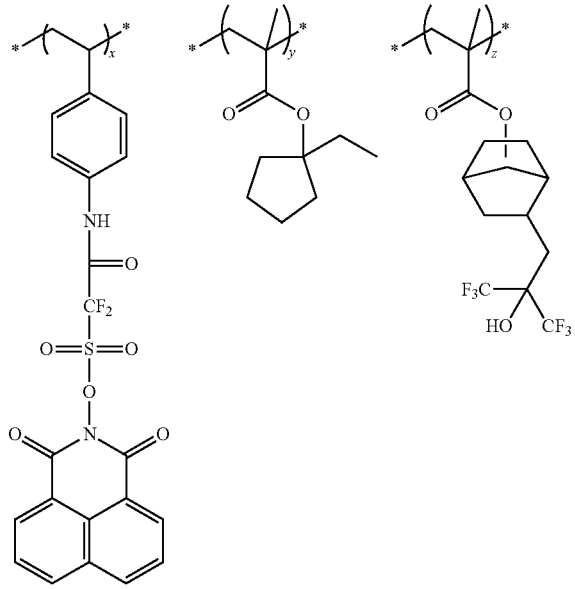 x/y/z = 5/40/55 |

TABLE 3-continued

| Example | PAG Polymer | Repeating Units (mole ratio)[a] |
|---|---|---|
| 11 | P-5 | [structures of three repeating units: x unit with ester-ethyl-NH-C(O)-CF2-SO2-O-N(naphthalimide); y unit with ester-1-ethylcyclopentyl; z unit with 4-hydroxyphenyl] x/y/z = 5/40/55 |
| 12 | P-6 | [structures of four repeating units: x unit with ester-ethyl-NH-C(O)-CF2-SO2-O-N(naphthalimide); y unit with ester-1-ethylcyclopentyl; z unit with ester-norbornyl-CH2-C(CF3)2-OH; z' unit with ester-norbornane lactone] x/y/z/z' = 5/40/15/40 |

TABLE 3-continued
| Example | PAG Polymer | Repeating Units (mole ratio)[a] |
|---|---|---|
| 13 | P-7 |   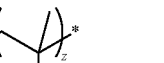<br>x/y/z = 5/40/55 |
| 14 | P-8 | 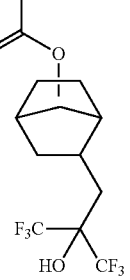  <br>x/y/z = 5/45/50 |

TABLE 3-continued
| Example | PAG Polymer | Repeating Units (mole ratio)[a] |
|---|---|---|
| 15 | P-9 | 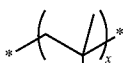  <br>x/y/z = 5/40/55 |
| 16 | P-10 | 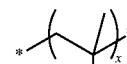 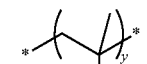 <br>x/y/z = 5/40/55 |

TABLE 3-continued
| | PAG | Repeating Units |
|---|---|---|
| Example | Polymer | (mole ratio)[a] |
17    P-11
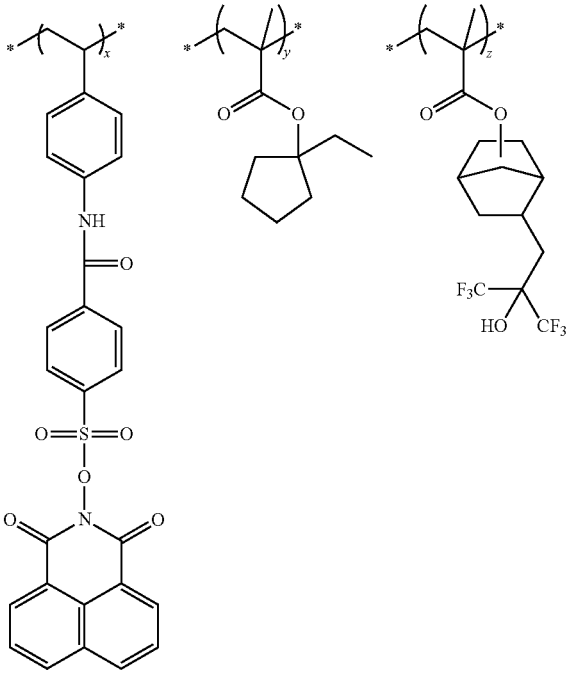
x/y/z = 5/40/55
18    P-12
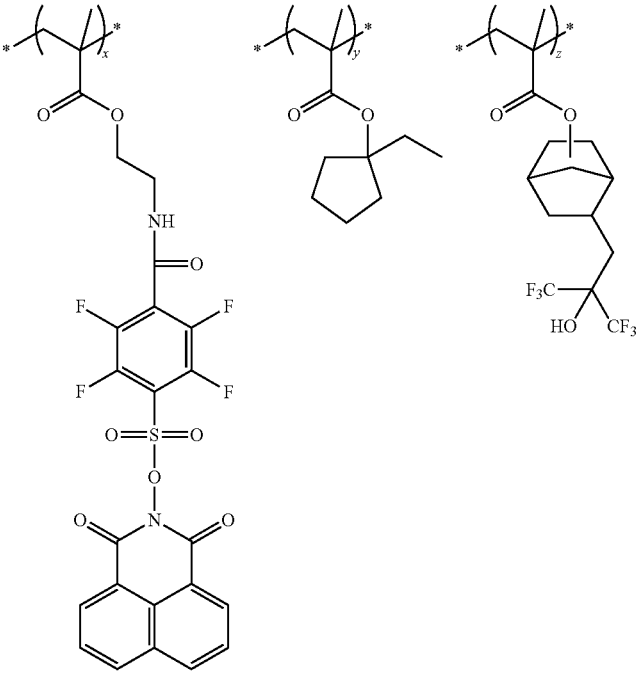
x/y/z = 5/40/55

TABLE 3-continued
| Example | PAG Polymer | Repeating Units (mole ratio)[a] |
|---|---|---|
| 19 | P-13 | 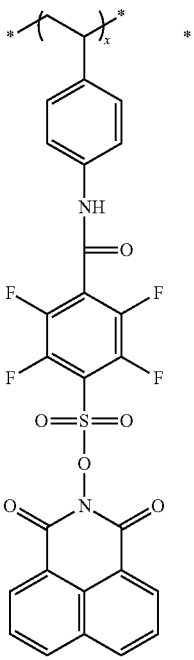  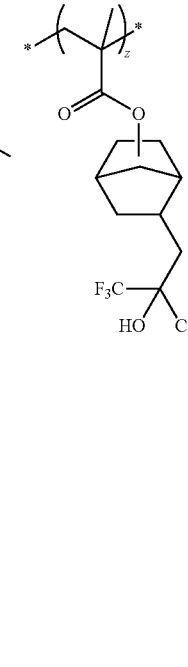 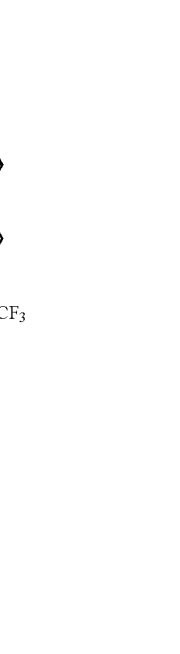<br>x/y/z = 5/40/55 |
| 20 (comp) | P-14 (comp) | 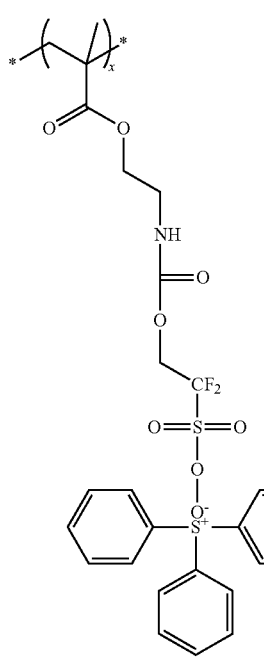 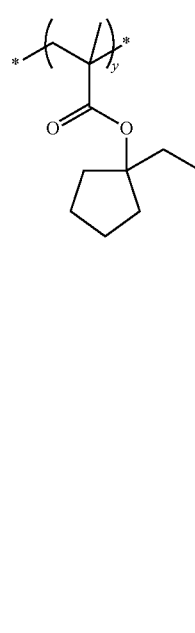 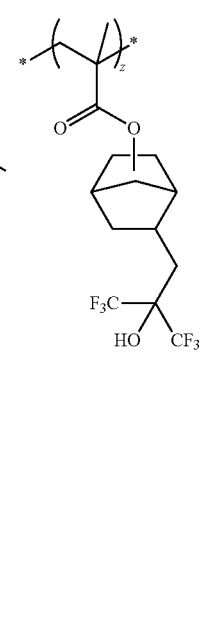 <br>x/y/z = 5/40/55 |

TABLE 3-continued

| Example | PAG Polymer | Repeating Units (mole ratio)[a] |
|---|---|---|
| 21 (comp) | P-15 | 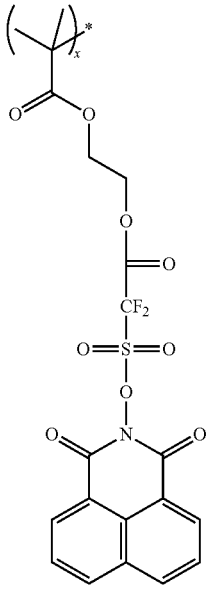 x/y/z = 5/40/55 |

Each of the random copolymer structures of P-1 to P-15 listed in Table 3 can be written using the following notation, exemplified by P-1:

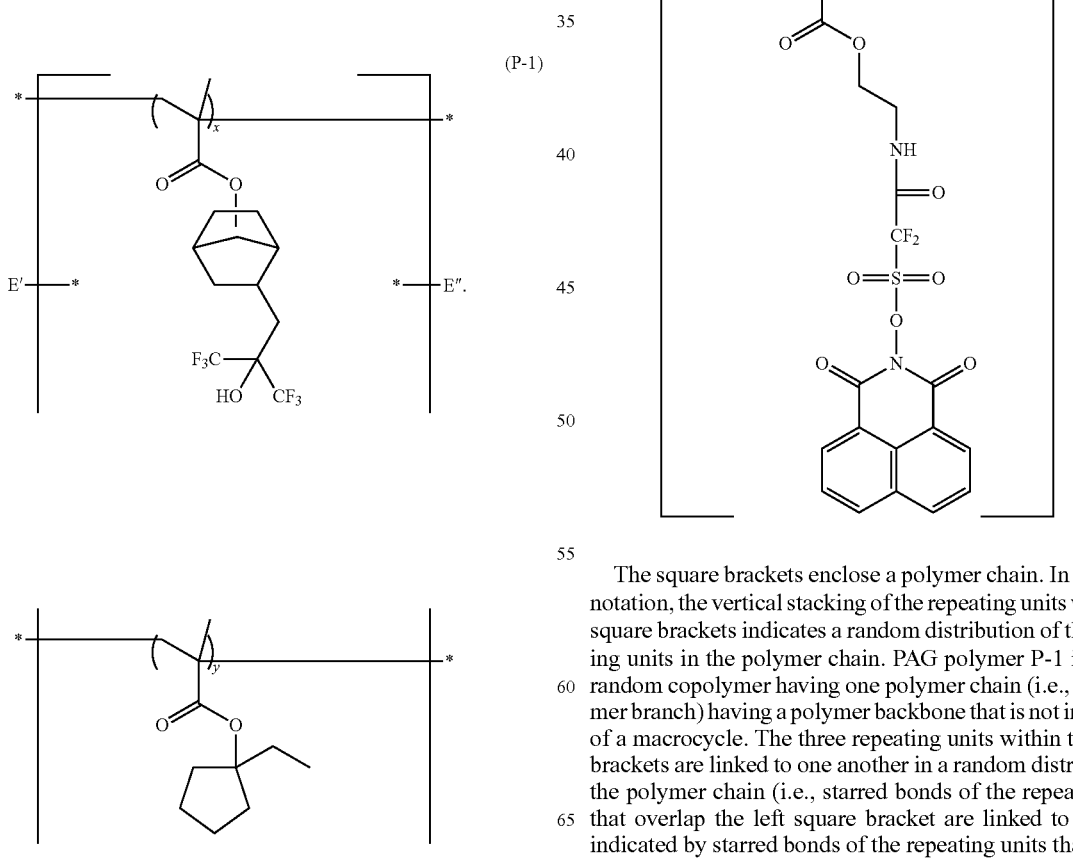

(P-1)

The square brackets enclose a polymer chain. In the above notation, the vertical stacking of the repeating units within the square brackets indicates a random distribution of the repeating units in the polymer chain. PAG polymer P-1 is a linear random copolymer having one polymer chain (i.e., one polymer branch) having a polymer backbone that is not in the form of a macrocycle. The three repeating units within the square brackets are linked to one another in a random distribution in the polymer chain (i.e., starred bonds of the repeating units that overlap the left square bracket are linked to positions indicated by starred bonds of the repeating units that overlap the right square bracket, and vice versa). Each of the subscripts x, y, and z indicates mole percent of the respective repeating unit present in the PAG polymer. E' and E" are monovalent end groups. In each polymer macromolecule, any one of the repeating units can be linked to E', and any one of the repeating units can be linked to E". End group E' is linked to one of the repeating units at a position indicated by the starred bonds of the repeating units overlapping the left square bracket. Likewise, end group E" is linked to one of the repeating units at a position indicated by the starred bonds of the repeating units that overlap the right square bracket.

In the above preparations, E' and E" can independently be 2-cyanoprop-2-yl $(CH_3)_2C(CN)$—*, dodecanethio $(CH_3(CH_2)_{10}CH_2S$—*), hydrogen, disproportion products of monomers, or a combination thereof.

Polymer Properties

The non-ionic PAG polymers (P-1 to P-13) were readily soluble in propylene glycol monomethyl ether acetate (PGMEA), one of the desired solvents for resist formulations. The non-ionic PAG polymers have a polydispersity in a range of 1.32 to 1.77 by gel permeation chromatography (GPC). About 15 mol % of non-ionic PAG monomer was incorporated without precipitating the PAG polymer in the polymerization solvent (e.g., tetrahydrofuran (THF)) and/or in the resist formulation solvent (PGMEA).

Ionic PAG polymers, on the other hand, usually require solvents such as cyclohexanone that are not widely used in resist formulations. Additionally, ionic PAG polymers containing greater than 5 mol % of ionic PAG monomer (e.g., TPS-UMA) typically precipitated during polymerization and were difficult to dissolve in common coating solvents after isolation of the PAG polymer.

Thermal Stability

Figure 3:
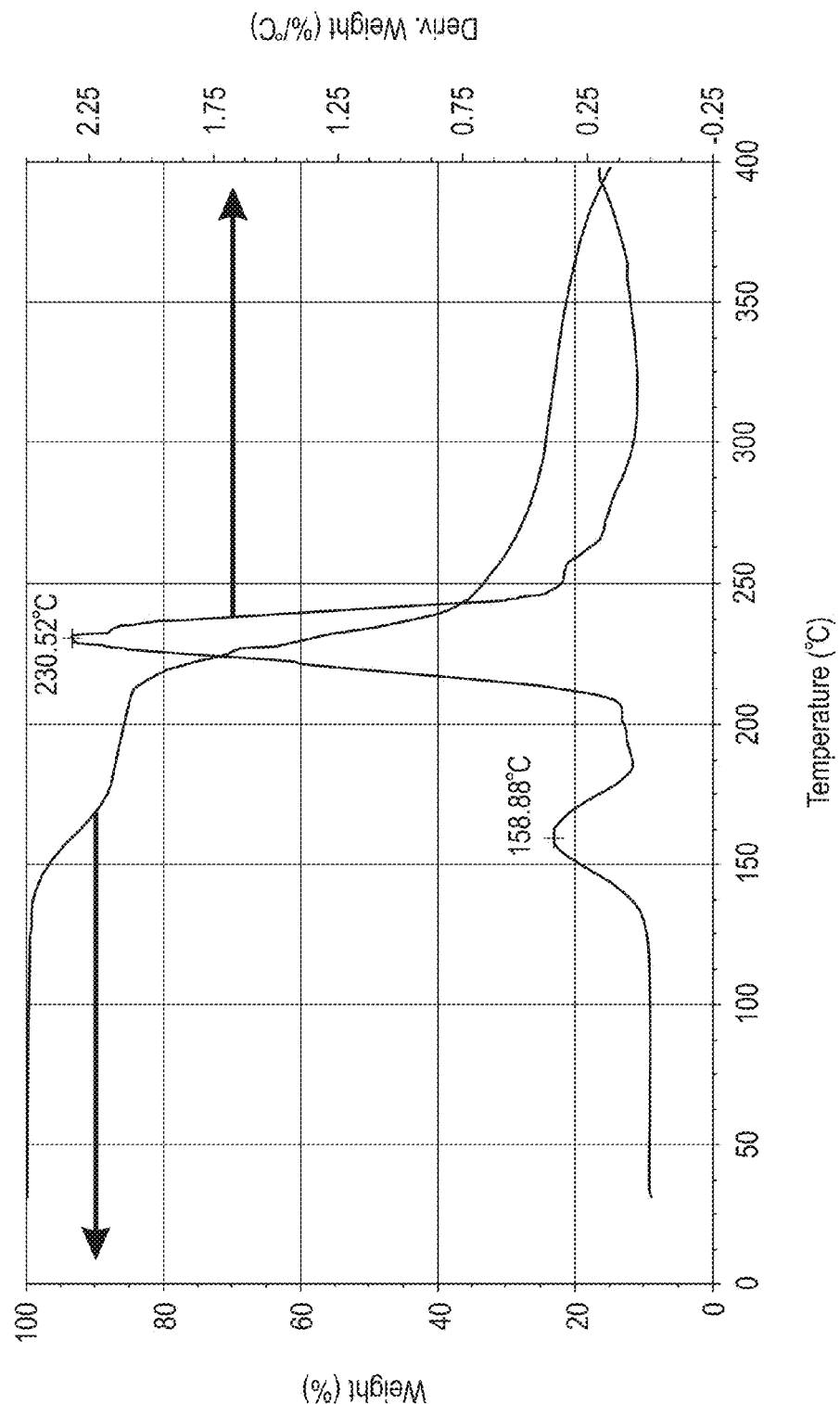
FIG. 3 is a thermal gravimetric analysis (TGA) plot for P-1. The decomposition temperature $T_d$ (i.e., the temperature at which thermolysis of the sulfonate ester PAG produces strong acid resulting in the deprotection of the acid-labile group) is about 159° C.

Non-ionic PAG polymers comprising a hexafluoroalcohol (HFA) group (P-1 to P-4 and P-6 to P-13) were thermally stable at least to 130° C. The thermogravimetric analysis (TGA) plot of polymer P-1 is shown in FIG. 3 as an example. The thermal decomposition temperature $(T_d)$ for P-1 is about 159° C., at which deprotection of the acid-labile group occurs.

Phenol-containing polymer P-5 has a thermal decomposition temperature $(T_d)$ of 109° C. As shown further below, P-5 was not suitable for lithographic patterning.

Resist Compositions

Resist compositions for non-ionic PAG polymers P-1 to P-13 were prepared by forming a 3.5 wt % (weight percent) solution, based on total weight of the solution, of a given PAG polymer in propylene glycol methyl ether acetate (PGMEA). An organic base, 2-phenyl benzimidazole, was added to the solution in an amount of 0.33 wt % or 0.66 wt % based on total weight of the PAG polymer as a quencher. The solution was then filtered through a 0.2 micrometer poly(tetrafluoroethylene) (PTFE) syringe filter.

For ionic PAG polymer P-14, cyclohexanone was the formulating solvent.

Resist Processing

Resist compositions were made by dissolving the PAG polymers in an organic solvent or an organic solvent mixture. The formulations can contain organic base, surfactant, and/or other additives.

Pattern formation using the resist composition of the invention can be performed by well-known lithographic processes. The process generally involves coating, prebaking, exposing to high-energy radiation (typically E-Beam or EUV), post exposure baking (PEB), and developing with alkaline developer. These steps are described in more detail below.

The resist composition is first applied onto a substrate (e.g., silicon wafer having a surface layer of Si, $SiO_2$, SiN, SiON, TiN, WSi, BPSG, SOG, organic antireflective coating or the like) for integrated circuit (IC) fabrication, or a substrate for mask circuit fabrication (e.g., quartz substrate having a surface layer of Cr, CrO, CrON, MoSi or the like) by a suitable coating technique such as spin coating followed by a prebake, also known as post apply bake (PAB).

Then, the resist film is exposed to high-energy radiation, such as deep UV, excimer laser, x-ray or EUV through a mask having a desired pattern. Alternatively, a pattern is written on the resist film directly with E-Beam. The exposure dose is preferably on the order of about 1 $mJ/cm^2$ to about 200 $mJ/cm^2$, more preferably about 10 $mJ/cm^2$ to about 100 $mJ/cm^2$. Alternatively, a pattern is written on the resist film directly with E-beam radiation, in which case the exposure dose is generally in the range of about 1 $\mu C/cm^2$ to about 400 $\mu C/cm^2$. The exposure can be performed by conventional lithography or by immersion lithography of holding a liquid between the mask and the resist film. In this case, a protective film which is insoluble in water can be applied on the resist film.

The exposed resist film is given a post-exposure bake (PEB) on a hot plate at 60 to 150° C. for 1 to 10 minutes, preferably 80 to 140° C. for 1 to 5 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

The resist formulation was spin coated to a thickness between 30 to 50 nm onto silicon wafers having a bottom anti-reflective coating (BARC). The BARC underlayer was used for adhesion purposes. The wafer was given a post-apply bake at 110° C. for 60 seconds on a hot plate. The wafer was then exposed on a 0.3-NA extreme ultraviolet (EUV) micro exposure tool (MET) at variable doses. The exposed wafer was given a post-exposure bake at 110° C. for 60 seconds. Both bakes were done with the wafer in contact with the hot plate. A 60-second development of the resist was carried out using a gentle spray of 0.26 N aqueous TMAH to puddle followed by water rinse and spin dry. Top and cross-sectional images were inspected using a LEO Carl Zeiss scanning electron micrograph (SEM) tool. Cross sectional samples were coated with thin PdAu to avoid sample charging.

E-beam exposures were performed using a 100 KeV Leica VB6 at variable doses and processed as described above.

Radiation Sensitivity of PAG-Bound Polymers

Figure 4:
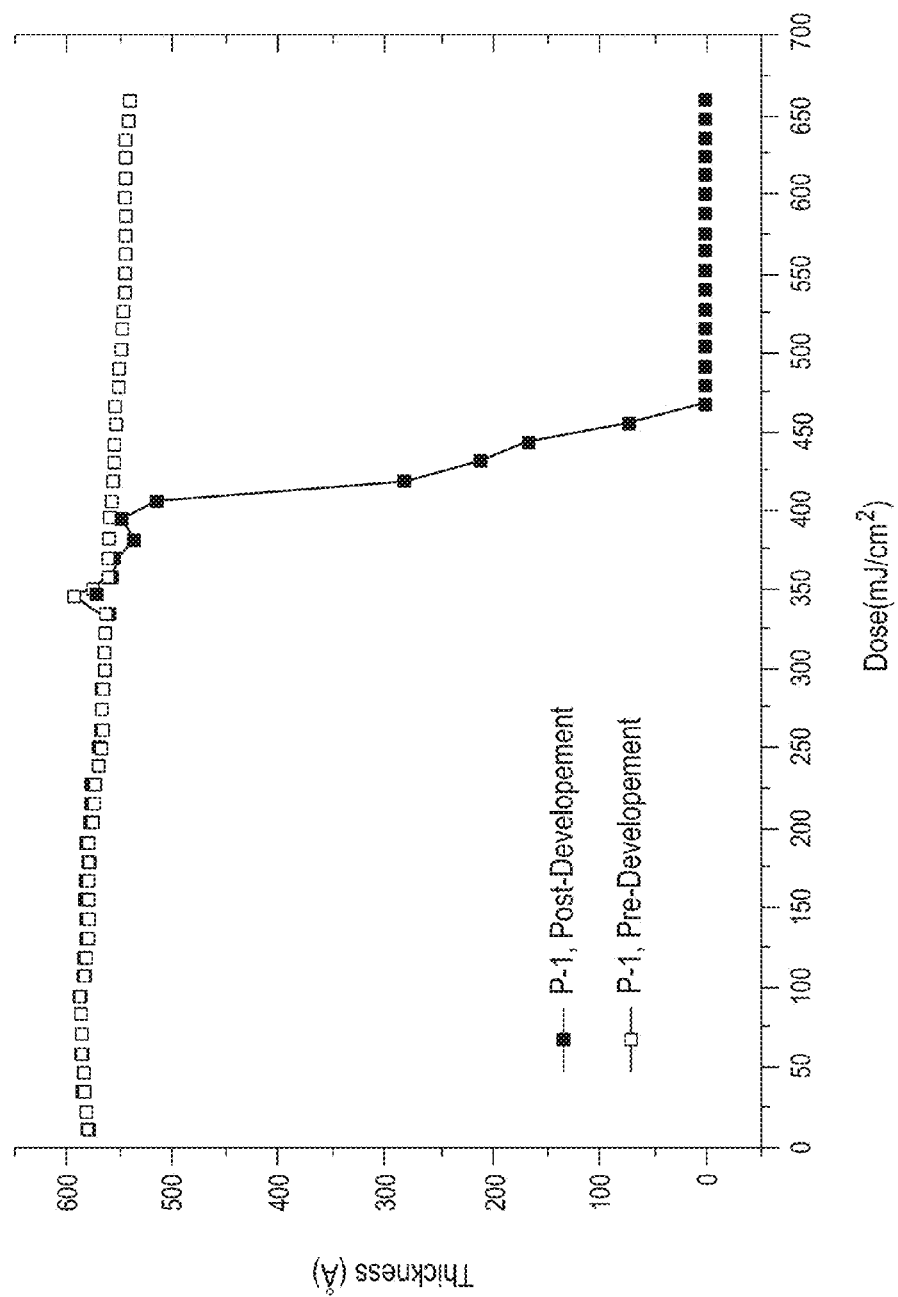
FIG. 4 is a graph showing the contrast curve obtained for a resist layer formed with P-1 exposed at 248 nm ($E_o$~450 mJ/cm$^2$). Closed squares represent post-development and open squares represent pre-development.
Figure 5:
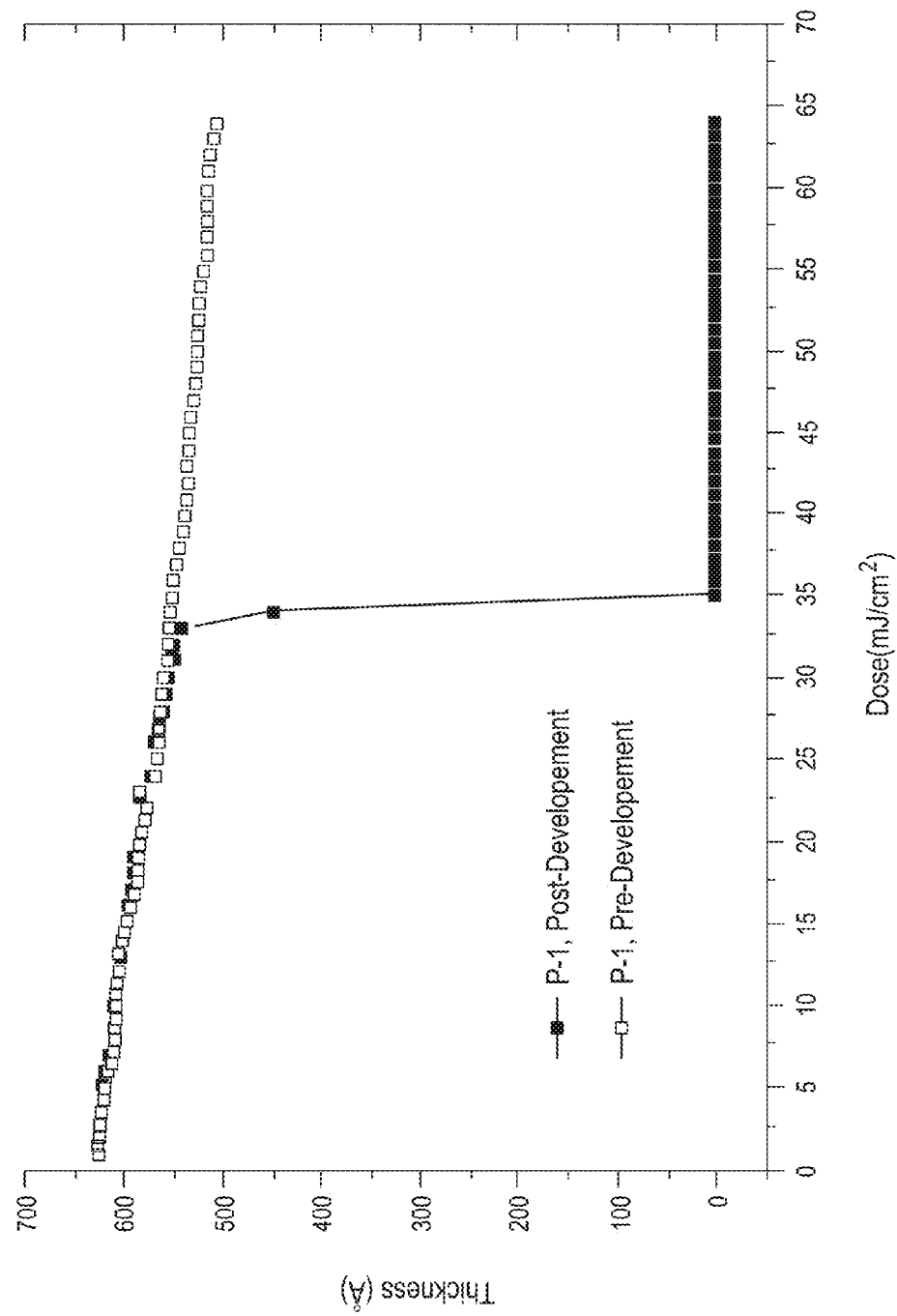
FIG. 5 is a graph showing the contrast curve obtained for a resist layer formed with P-1 exposed at 193 nm ($E_o$~35 mJ/cm$^2$). Closed squares represent post-development and open squares represent pre-development.
Figure 6:
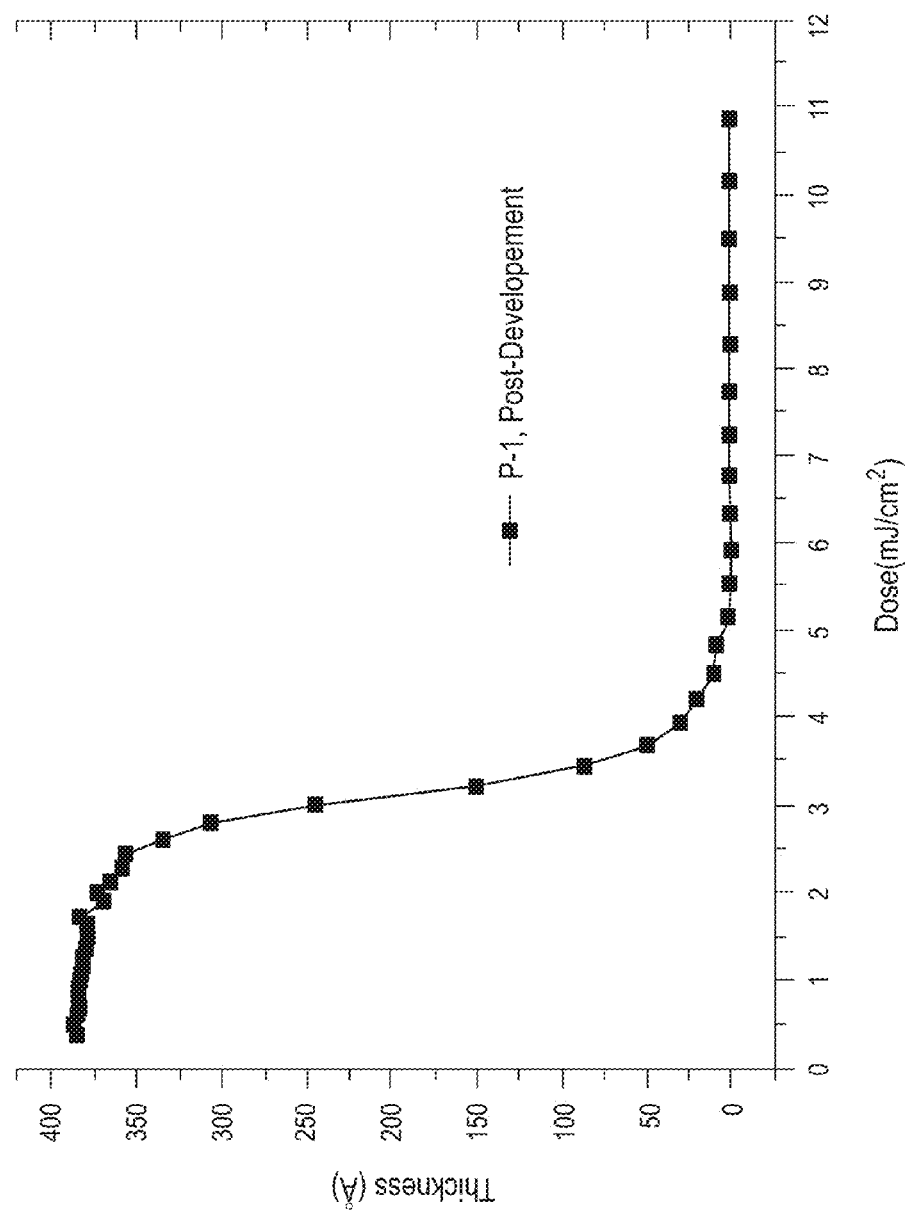
FIG. 6 is a graph showing the contrast curve obtained for a resist layer formed with P-1 exposed at 13.5 nm (EUV, $E_o$~5 mJ/cm$^2$). Closed squares represent post-development.
Figure 7:
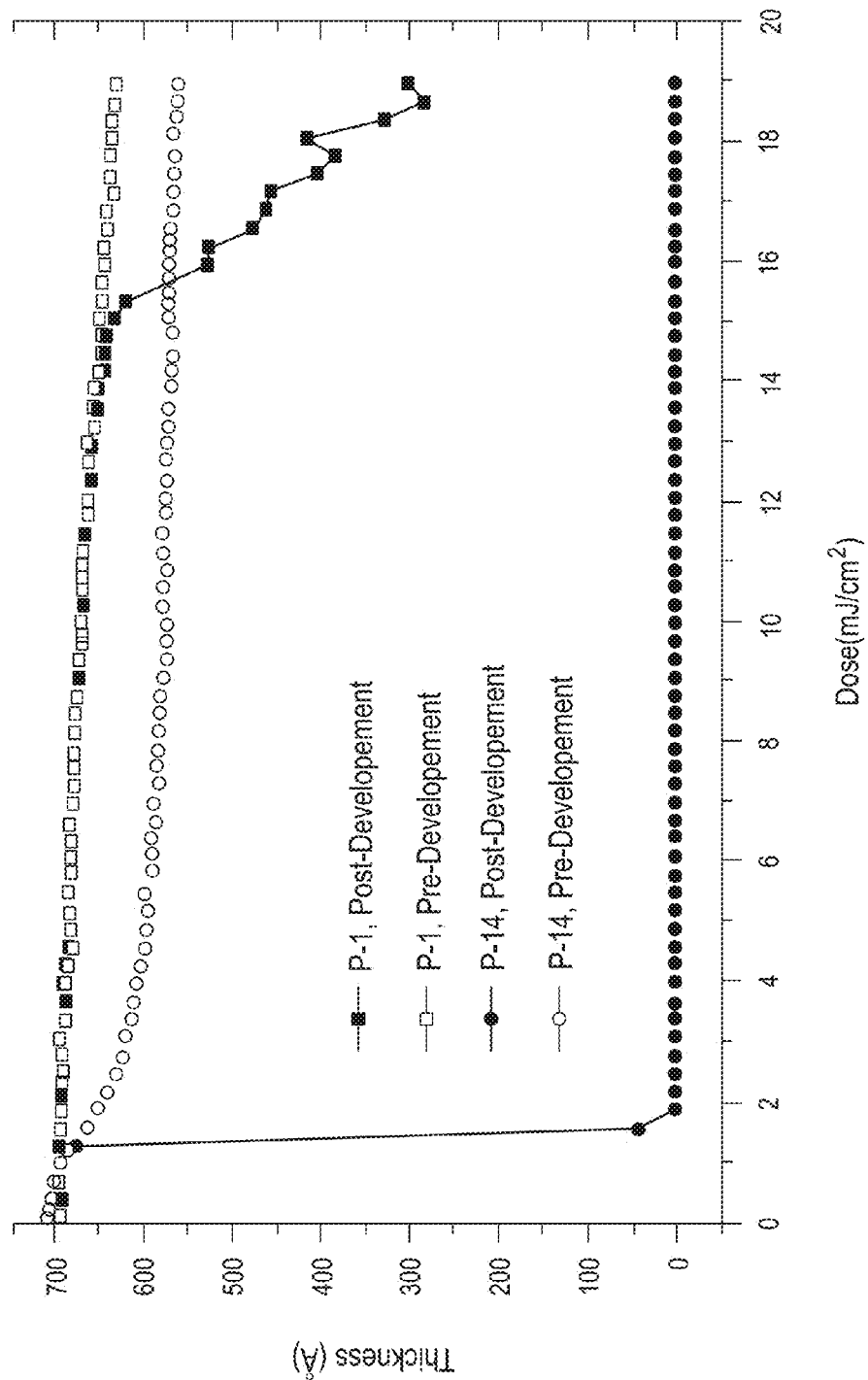
FIG. 7 is a graph showing the contrast curves obtained for a resist layers formed with P-1 and P-14 exposed at 193 nm. Closed squares represent post-development and open squares represent pre-development of P-1. Closed circles represent post-development and open circles represent pre-development of P-14.
Figure 8:
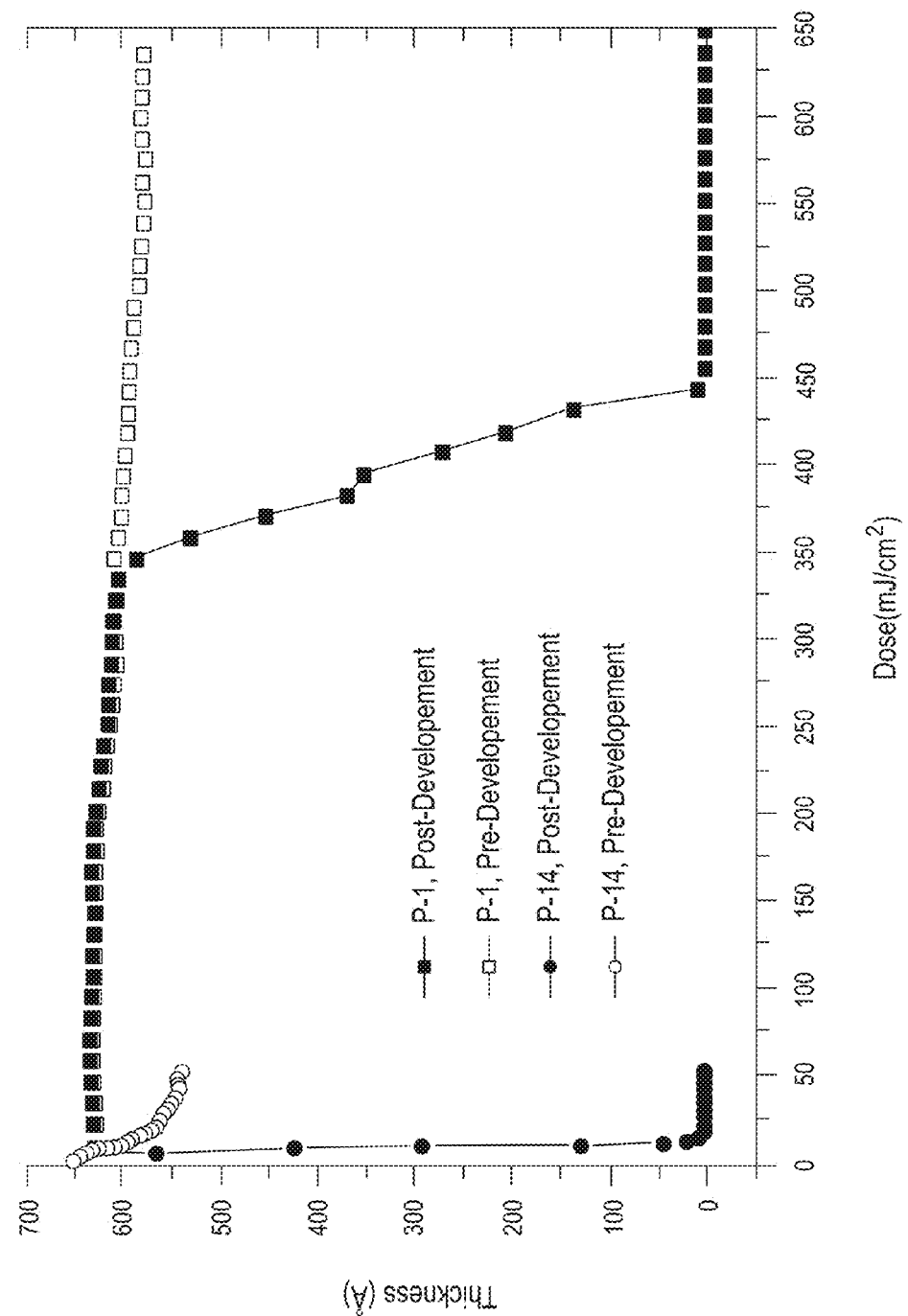
FIG. 8 is a graph showing the contrast curves obtained for a resist layers formed with P-1 and P-14 exposed at 248 nm. Closed squares represent post-development and open squares represent pre-development of P-1. Closed circles represent post-development and open circles represent pre-development of P-14.
Figure 9:
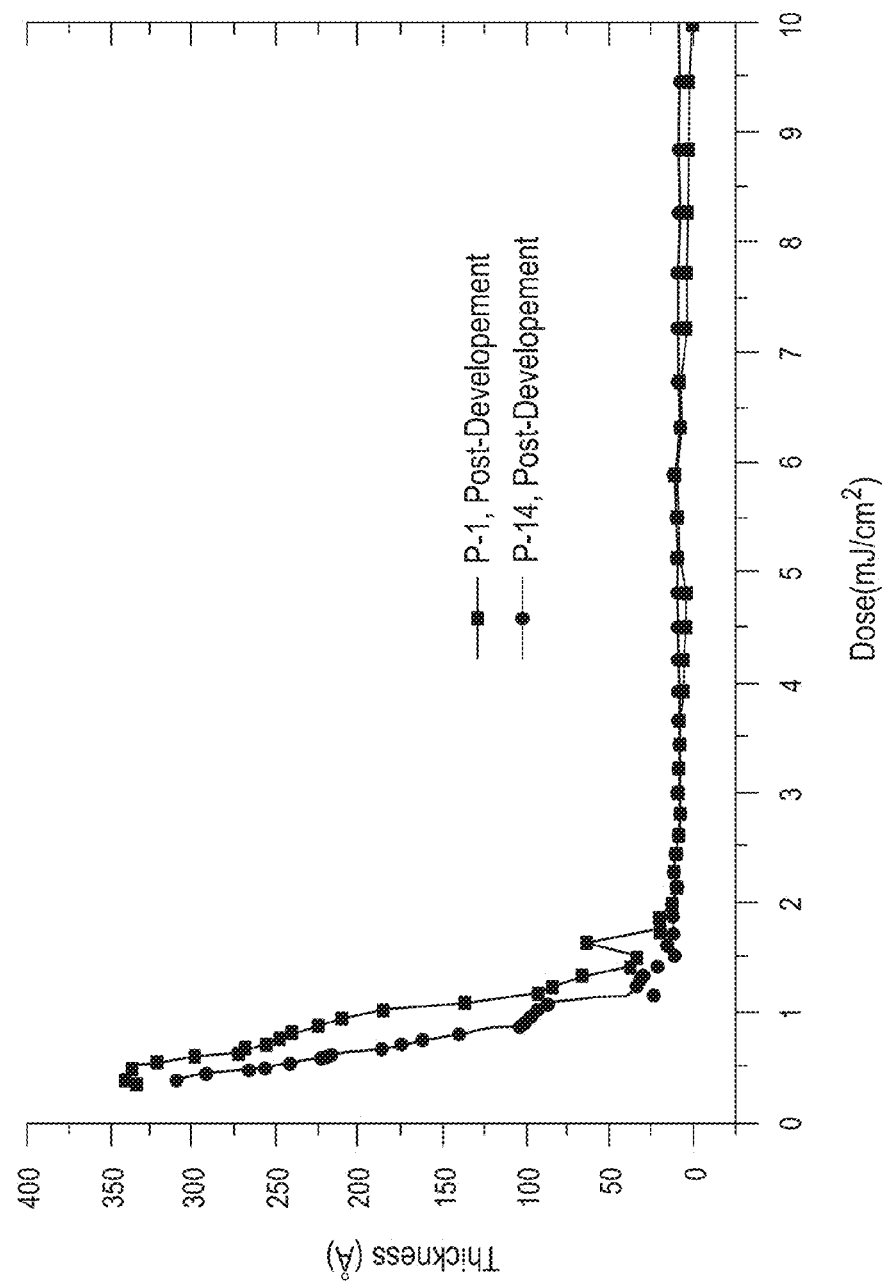
FIG. 9 is a graph showing the contrast curves obtained for a resist layers formed with P-1 and P-14 exposed at 13.5 nm (EUV).

The resist compositions comprising non-ionic PAG-bound polymers (except Polymer 3) were generally insensitive to 193 nm and 248 nm radiations while highly sensitive to EUV radiation, as shown by the contrast curves obtained for the resist formulation comprising P-1 using exposures at 248 nm (FIG. 4, $E_o$ about 450 $mJ/cm^2$), 193 nm (FIG. 5, $E_o$ about 35 $mJ/cm^2$), and 13.5 nm (EUV, FIG. 6, $E_o$ about 5 $mJ/cm^2$). This attribute of the non-ionic PAG polymer is useful in circumventing the effect of out-of band radiation emitted during a EUV exposure. This attribute is also specific to non-ionic PAG polymers. FIGS. 7-9 are contrast curves comparing the sensitivity of P-1 and P-14 at 193 nm, 248 nm, and EUV, respectively. The ionic PAG polymer P-14 had high sensitivity to 193 nm, 248 nm, and EUV radiation.

Figure 10:
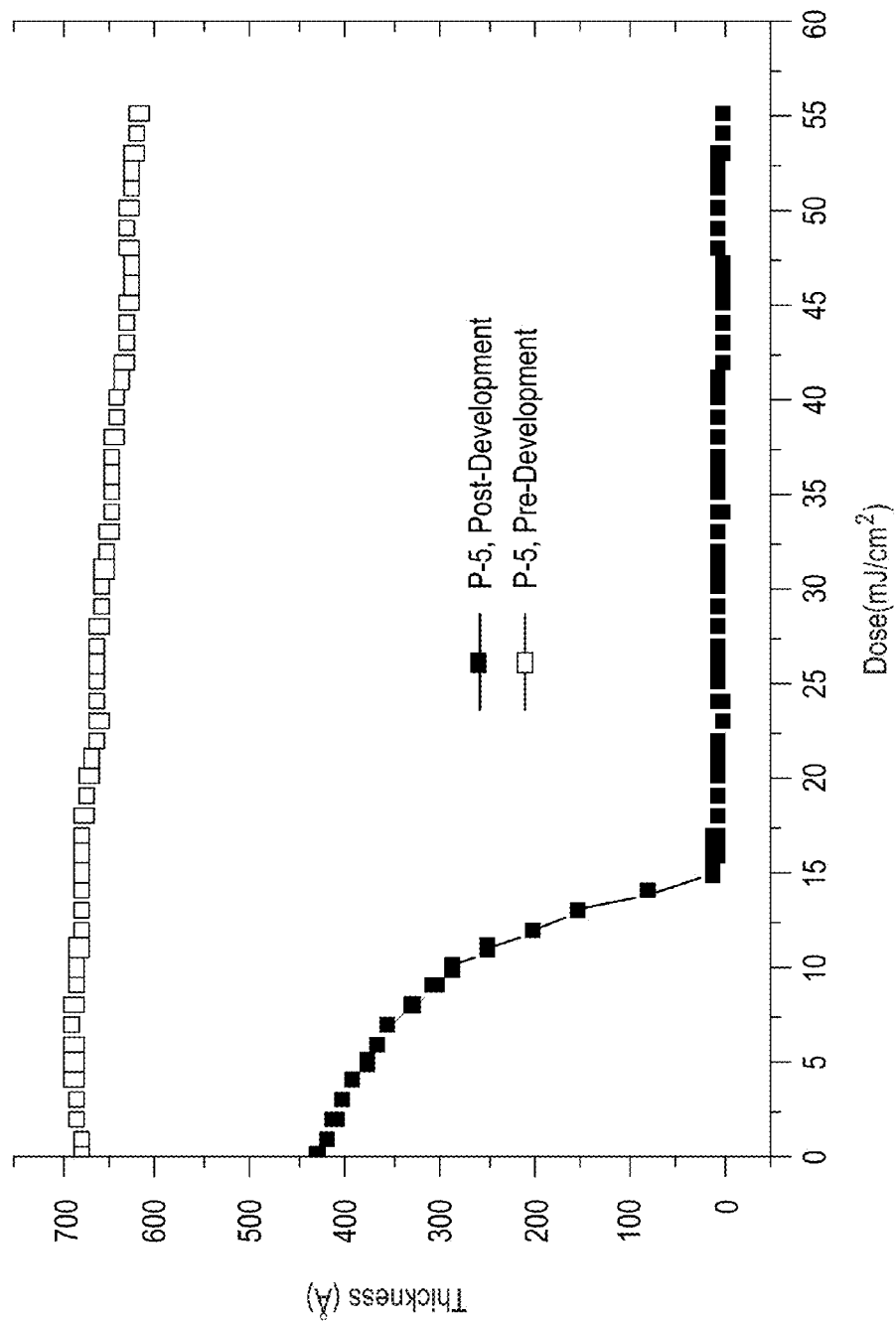
FIG. 10 is a graph showing the contrast curve obtained for a resist layer formed with P-5 where the post-apply bake (PAB) and post exposure bake (PEB) were 90° C., the exposure wavelength was 248 nm, and the dosage range was 0 to 55 mJ/cm$^2$. Closed rectangles represent post-development and open squares represent pre-development of P-5.

FIG. 10 depicts the contrast curve for a resist formulation of P-5 where the post-apply bake (PAB) and post exposure bake (PEB) were 90° C., the exposure wavelength was 248 nm, and the dosage range was 0 to 55 $mJ/cm^2$. Undesirable substantial thinning of the resist was observed even when the post exposure bake (PEB) was at 90° C.

Figure 11:
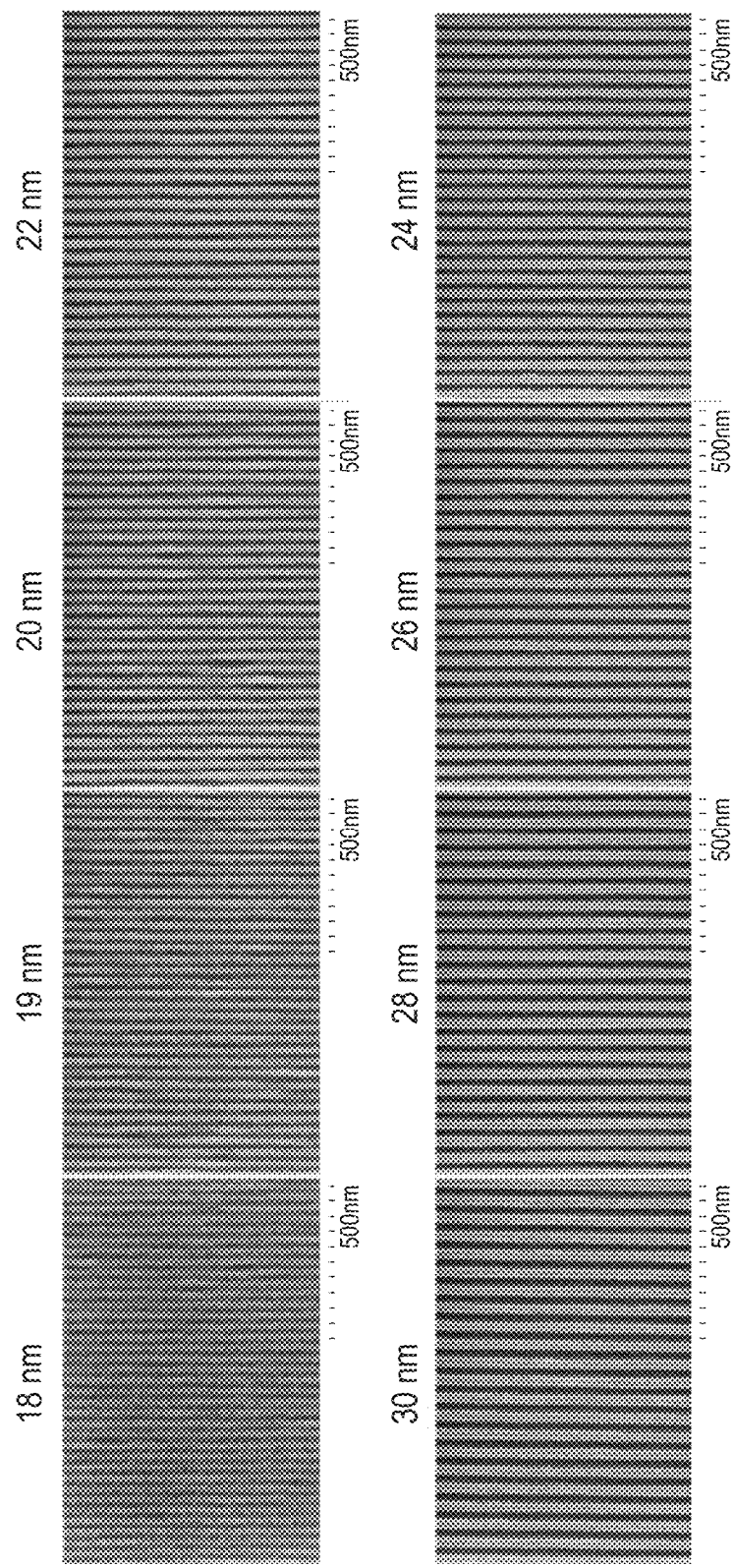
FIG. 11 is a series of SEM images of line/space patterns formed at resolutions of 18, 19, 20, 22, 24, 26, 28, and 30 nanometers using P-1 and EUV exposure.

The resist formulations containing non-ionic PAG polymer that comprised a hexafluoroalcohol moiety (HFA, *—C(CF$_3$)$_2$OH) were highly sensitive to EUV, showed good resolution, and produced line patterns having low line edge roughness (LER). FIG. 11 is a series of SEM images of line/space patterns having a critical dimension (CD) of 18, 19, 20, 22, 24, 26, 28, and 30 nm using P-1 and 0.66 wt % of the organic base 2-phenyl benzimidazole. The exposure and process conditions were as follows: film thickness (FT)=40 nm, PAB=110° C./60 seconds, exposure by EUV MET with rotated dipole, dose=18.37 mJ/cm$^2$, PEB=110° C./60 seconds, MF-26A developer/60 seconds.

Figure 12:
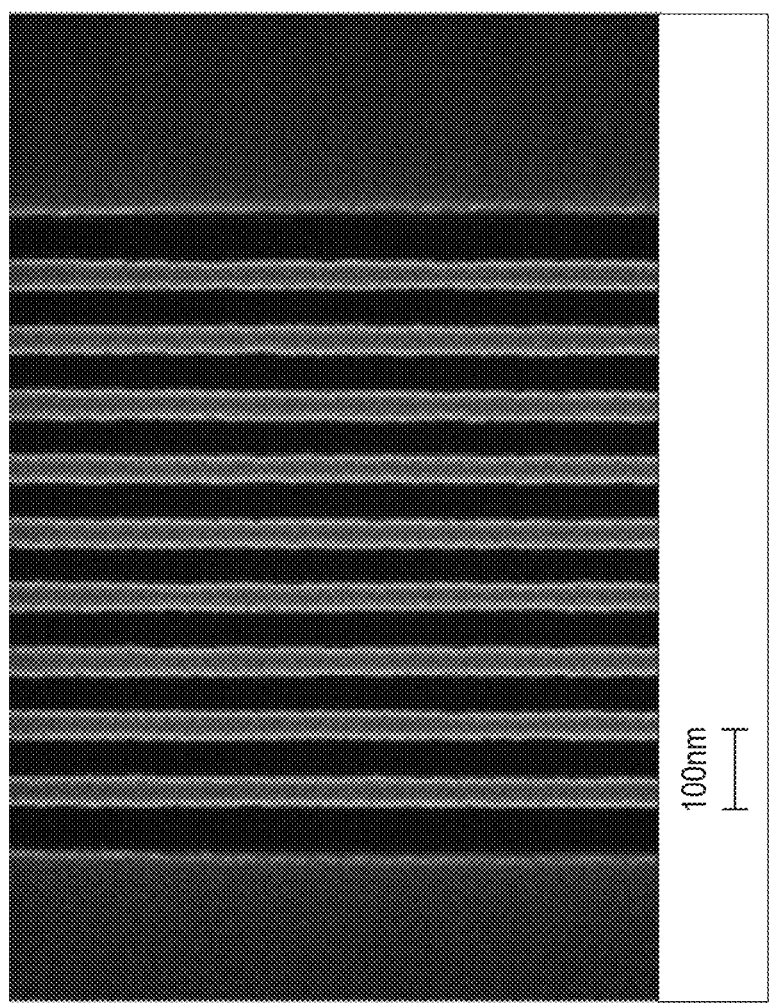
FIG. 12 is an SEM image of a line/space pattern formed at a resolution of 40 nanometer (1:1) with P-1 and E-beam exposure.
Figure 13:
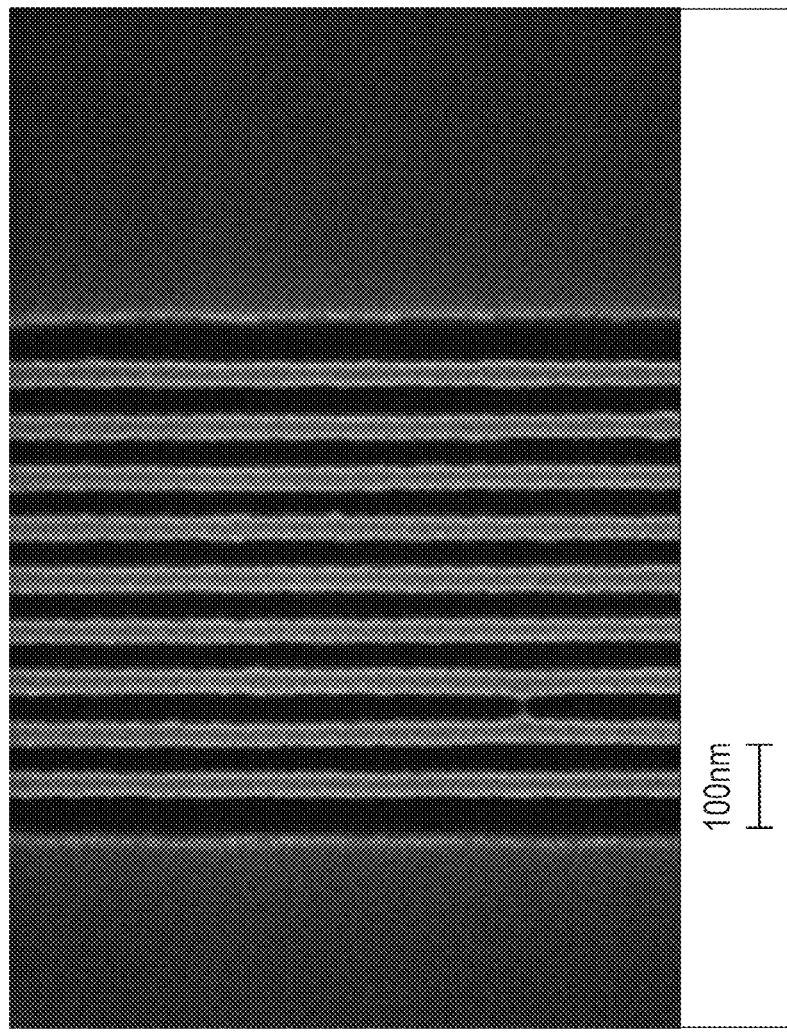
FIG. 13 is an SEM image of a line/space pattern formed at a resolution of 30 nanometer (1:1) with P-1 and E-beam exposure.

With E-beam, P-1 also gave high resolution line patterns having low line edge roughness (LER). However, the sensitivity was low (310 microCoulombs). FIGS. 12 and 13 are SEM images of line/space (1:1) patterns formed by E-beam exposures using a Leica 10 kV tool. In FIG. 12, the critical dimension (CD) was 35.5 nm, the line width roughness (LWR) was 3.0 nm, and the line edge roughness (LER) was 2.0 nm. In FIG. 13, the critical dimension (CD) was 28.95 nm, the line width roughness (LWR) was 3.4 nm, and the line edge roughness (LER) was 2.1 nm.

When the amount of non-ionic PAG monomer was greater than 5 mol % of the PAG polymer (e.g., P-2) the sensitivity of the otherwise identical resist formulations in EUV increased only moderately, allowing about 10% lower dose. Without being bound by theory, the dissolution inhibition effect of the polymer-bound PAG can have an influence when there is more PAG. That is, the increased concentration of the bulky PAG monomer can cause lower overall solubility in TMAH, offsetting the increased number of ionic groups formed by a given exposure. This should be taken into consideration when optimizing the polymer and resist compositions.

Discussion of Amide (PAG-1), Ester (PAG-7), and Carbamate Linkages

As taught by DeRuiter, J., Principles of Drug Action 1, Spring 2005, Amides, available at "www[dot]auburn.edu/~deruija/pda1_amides.pdf", the amide linkage of PAG-1 is less reactive towards nucleophilic attack (hydrolysis, etc.) than the ester linkage (of PAG-7) and the urethane (carbamate) linkage (used in US20120328985 A1). This is an important factor in the synthesis of these monomers because the procedures involve water work-up under basic conditions. The preparation of a comparative monomer PAG-7 clearly has a lower yield (2%) compared to the amide based monomer PAG-1 (46%). This reactivity also influences shelf stability of the resist formulations which usually have basic additives and some water (in the solvent). Therefore, monomer PAG-1 having the amide linkage is advantaged in terms of yield and stability over PAG-7.

Figure 21:
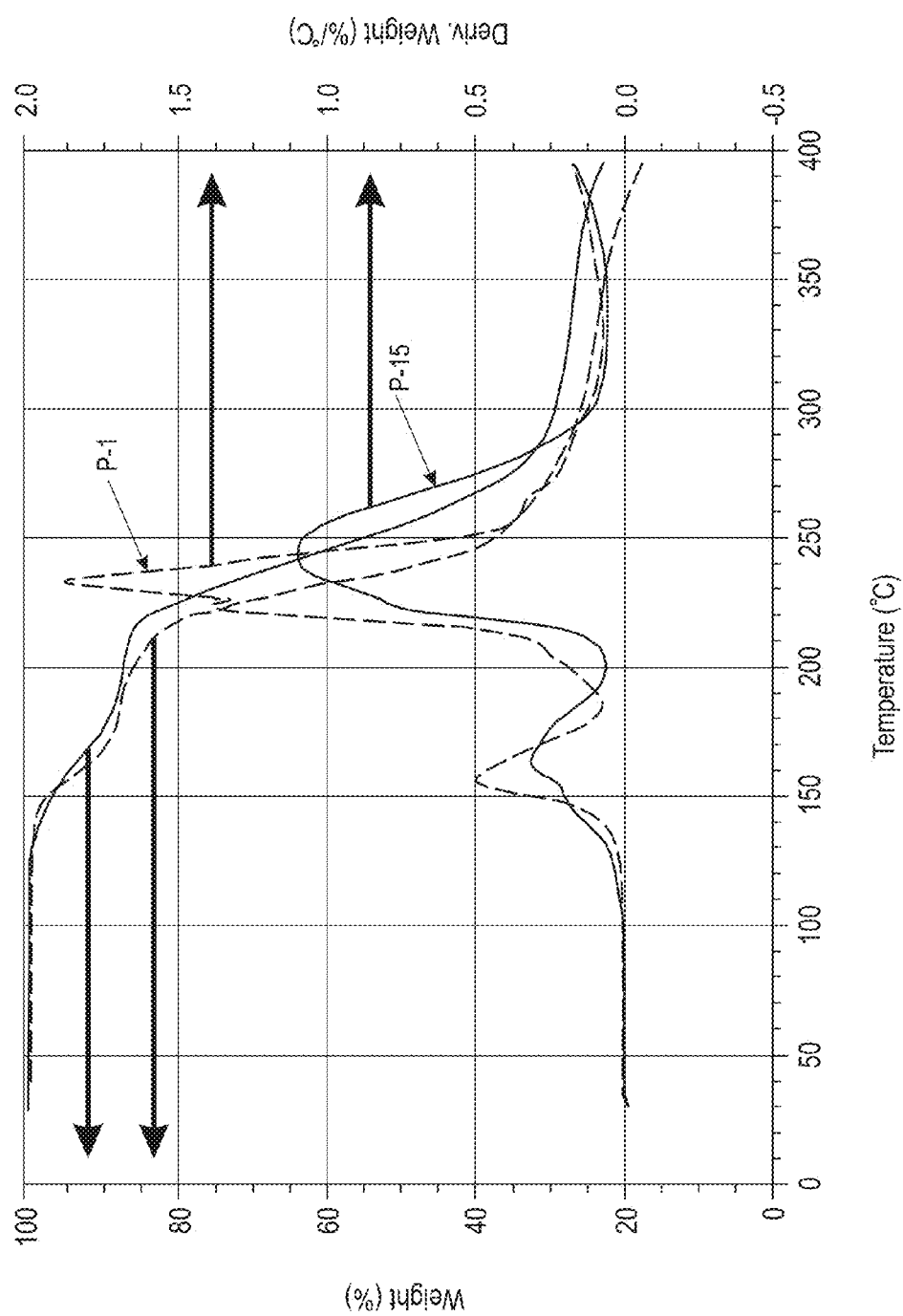
FIG. 21 is graph of the thermal gravimetric analysis (TGA) plots for P-1 and P-15 (comparative).

FIG. 21 is a graph showing the thermogravimetric analysis (TGA) of P-1 (from PAG-1) and P-15 (from PAG-7). P-1 is more thermal stable by about 15° C. over P-15.

Figure 22:
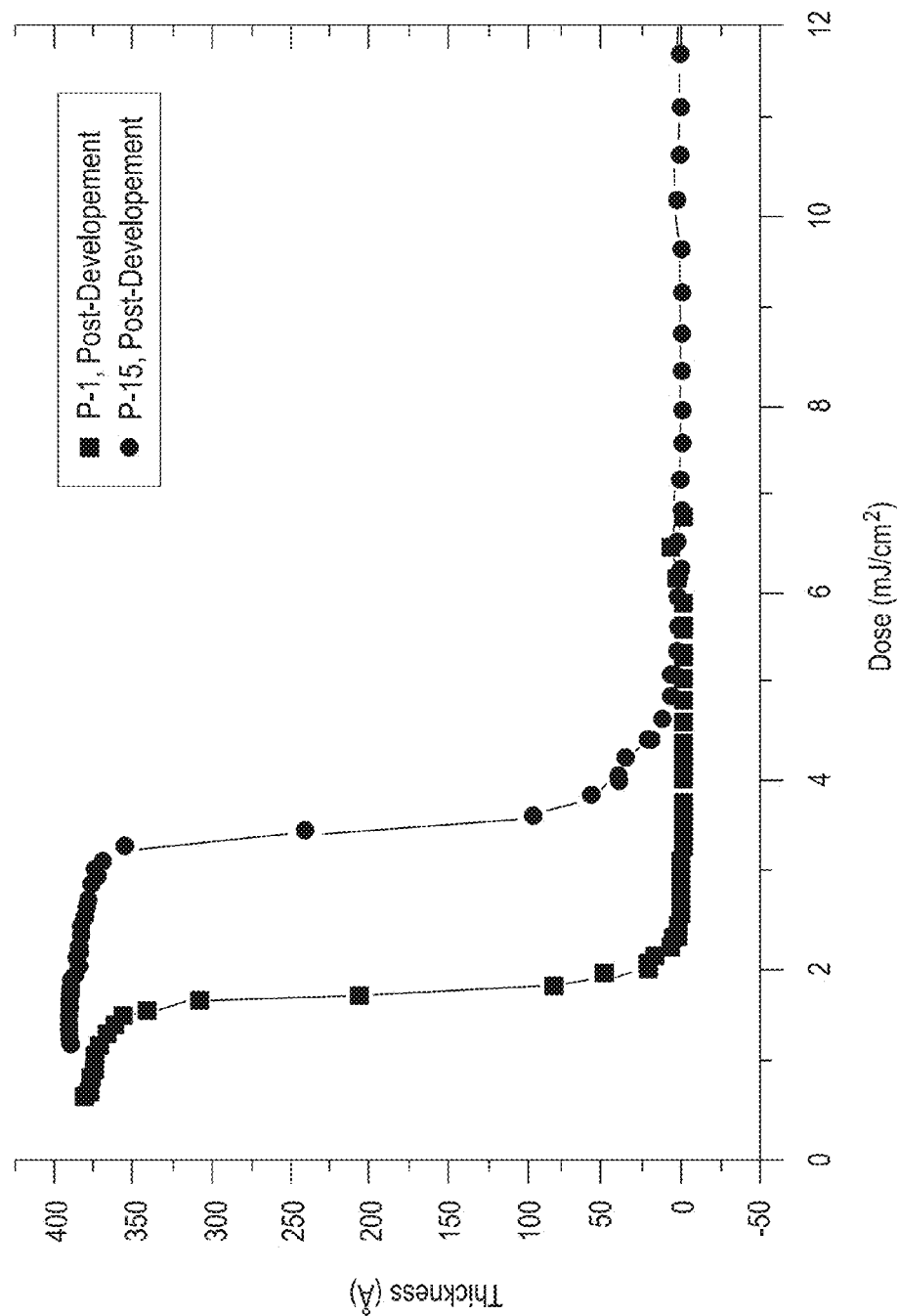
FIG. 22 is graph of contrast curves for formulations of P-1 and P-15 (comparative) containing 0.33 parts base quencher.
Figure 23:
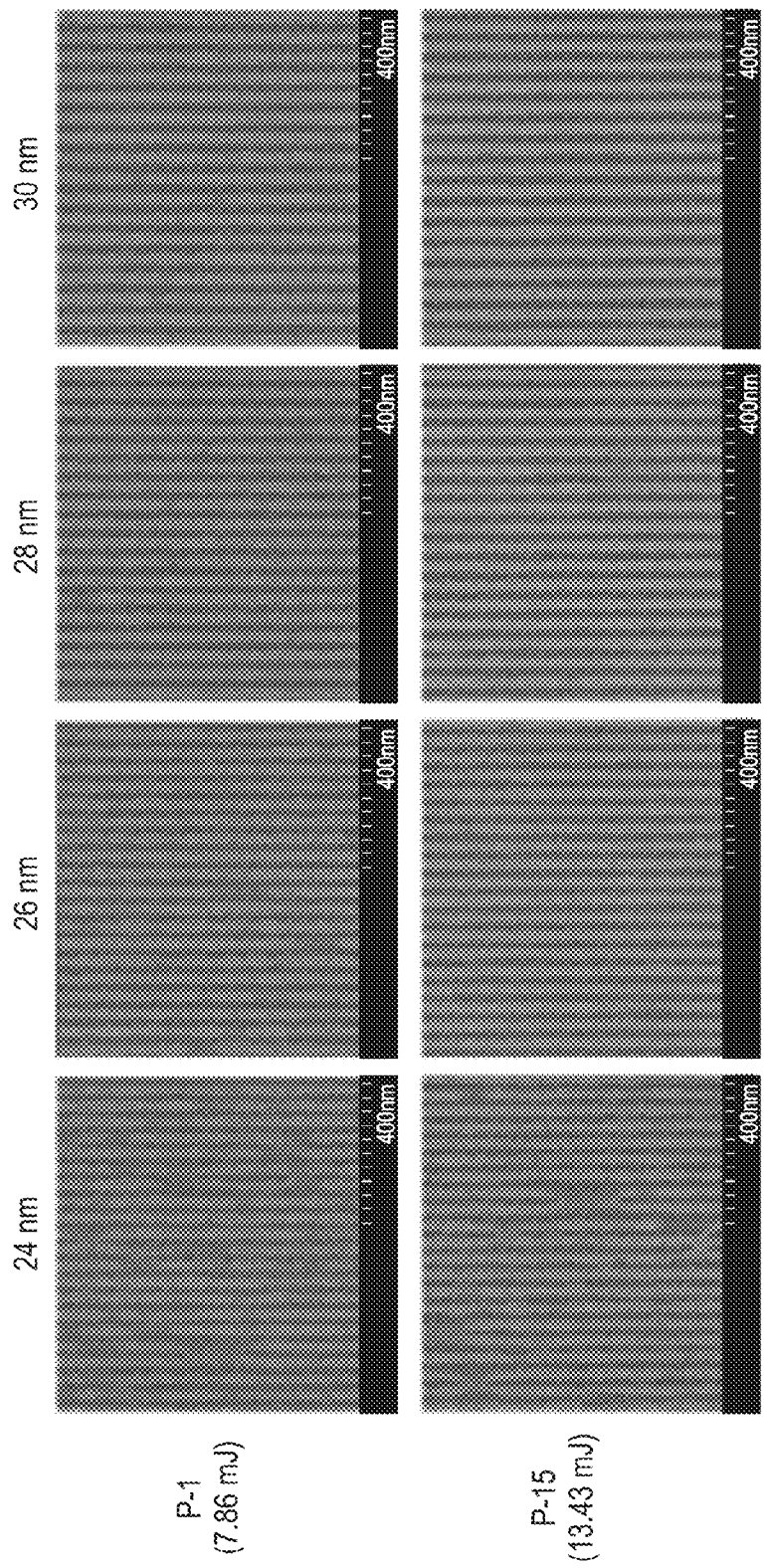
FIG. 23 is a series of SEM images of line/space patterns obtained with formulations of P-1 and P-15 (comparative) containing 0.33 parts base quencher (having unmatched sensitivities). For a comparison of matched sensitivities, compare FIG. 11 (P-1) and the bottom series of SEMs of FIG. 23 (P-15). Higher resolution was obtained with P-1.

FIG. 22 shows the contrast curves obtained using the EUV-MET exposure device for formulations of P1 and P-15. The formulations were identical except for the PAG polymer (both formulations used 0.33 parts quencher). The main observation was that the P-15 formulation was less sensitive than P-1. The resolutions were similar for these identical formulations (FIG. 23, SEM). However, when the sensitivities were brought closer (by adding 0.66 parts base to P-1 formulation), the P-1 formulation had much better resolution (see FIG. 11, SEM) compared to the P-15 formulation.

In summary, non-ionic PAG polymers of high sensitivity to EUV were prepared from non-ionic PAG monomers that contain an amide linking group. PAG polymers further comprising an auxiliary repeat unit having a pendant hexafluoroalcohol HFA group exhibited greatest thermal stability. The non-ionic PAG polymers were highly sensitive to 13.5 nm EUV radiation and much less sensitive to 193 nm and 248 nm UV radiation compared to an ionic PAG polymer P-14 (comparative Example 20) that was highly sensitive to all three wavelengths. These properties allow the PAG polymer to circumvent the detrimental effects of out-of-band radiation. Improved thermal stability, sensitivity, and line resolution were also obtained with PAG polymer P-1 (amide linkage) over PAG polymer P-15 (ester linkage, comparative).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A compound of formula (1):

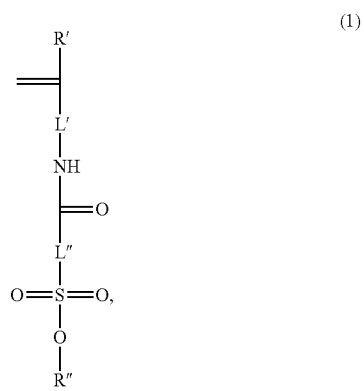

wherein
R' is a monovalent radical selected from the group consisting of H, F, C$_1$-C$_3$ alkyl groups, fluorine-containing C$_1$-C$_3$ alkyl groups, and cyano,
L' and L" are independently divalent radicals comprising 1 to 10 carbons,
a carbon of L" is linked to the carbonyl,
*—SO$_3$—R" represents a sulfonate ester of an N-hydroxy imide,
the compound is capable of polymerization, and the compound is capable of generating an acid upon exposure to radiation.

2. The compound of claim 1, wherein L' has a structure according to formula (2):

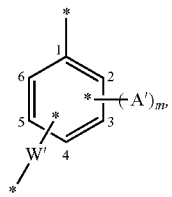

wherein
- m is an integer having a value of 0 to 4, and
- each A' when present is an independent monovalent radical having 0 to 2 carbons,
- W' is a single bond or a divalent radical selected from the group consisting of alkylene groups comprising 1 to 4 carbons, and fluorinated alkylene groups comprising 1 to 4 carbons, and
- W' is linked to the amide nitrogen of formula (1).

3. The compound of claim 2, wherein A' is selected from the group consisting of fluorine, bromine, chlorine, methyl, ethyl, methoxy, ethoxy, and acetoxy.

4. The compound of claim 1, wherein L' has a structure according to formula (3):

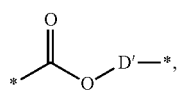

wherein
- the carbonyl starred bond is linked to the vinyl group of formula (1),
- D' is a divalent radical selected from the group consisting of alkylene groups comprising 2 to 9 carbons, and
- D' is linked to the amide nitrogen of formula (1).

5. The compound of claim 4, wherein D' is 1,2-ethylene (*—CH$_2$CH$_2$—*).

6. The compound of claim 5, wherein L" is 1,4-phenylene (*—C$_6$H$_4$—*).

7. The compound of claim 5, wherein L" is tetrafluoro-1,4-phenylene (*—C$_6$F$_4$—*).

8. The compound of claim 1, wherein L" is selected from the group consisting of methylene (*—CH$_2$—*), difluoromethylene (*—CF$_2$—*), 1,4-phenylene (*—C$_6$H$_4$—*), fluoro-1,4-phenylene (*—C$_6$H$_3$F—*), difluoro-1,4-phenylene (*—C$_6$H$_2$F$_2$—*), trifluoro-1,4-phenylene (*—C$_6$HF$_3$—*), tetrafluoro-1,4-phenylene (*—C$_6$F$_4$—*), trifluoromethyl-1,4-phenylene (*—C$_6$H$_3$(CF$_3$)—*), and bis-trifluoromethyl-1,4-phenylene (*—C$_6$H$_2$(CF$_3$)$_2$—*), and any positional isomers of the foregoing groups with respect to the fluorine and trifluoromethyl groups.

9. The compound of claim 1, wherein R" has a structure according to formula (4):

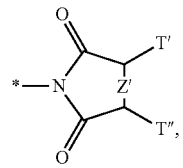

wherein
- the nitrogen starred bond is linked to the sulfonate oxygen of formula (1),
- Z' represents a single bond, a double bond, a methylene group, an aromatic carbon atom, or an oxygen atom,
- T' is hydrogen or a group comprising 1 to 10 carbons, and
- T" is hydrogen or a group comprising 1 to 10 carbons.

10. The compound of claim 1, wherein R" is:

11. The compound of claim 1, wherein the compound is selected from the group consisting of:

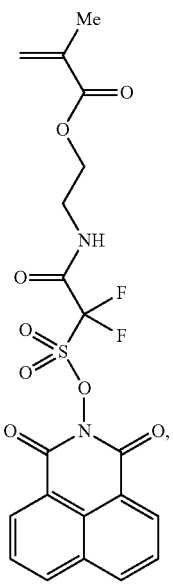

PAG-1

-continued

PAG-2
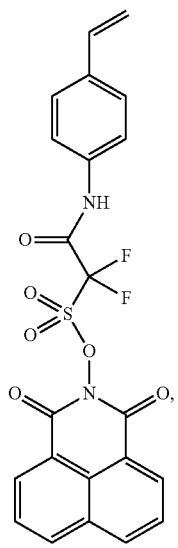

PAG-3
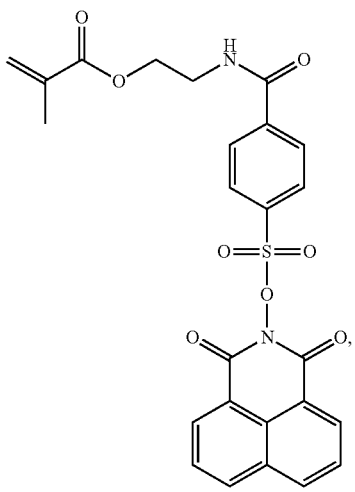

PAG-4
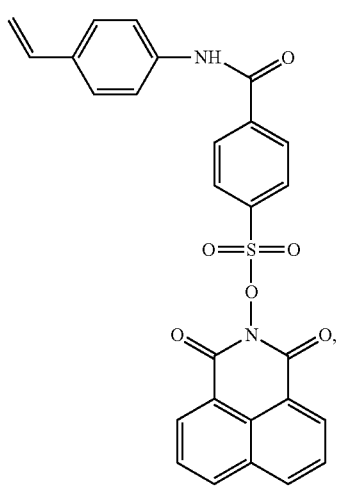

-continued

PAG-5
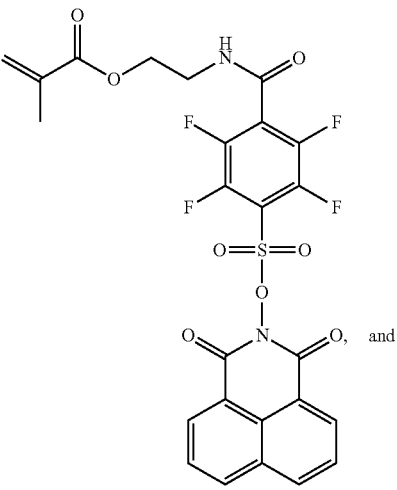
and

PAG-6
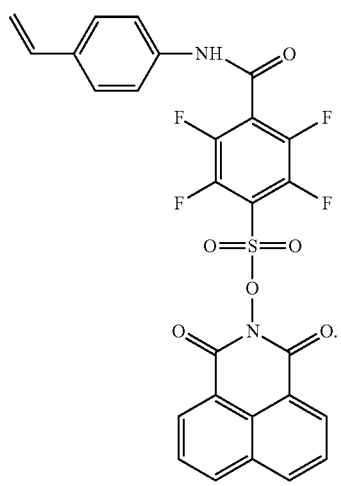

12. The compound of claim 1, wherein L" is difluoromethylene (*—CF$_2$—*).

13. The compound of claim 1, wherein L" is 1,4-phenylene (*—C$_6$H$_4$—*).

14. The compound of claim 1, wherein L" is tetrafluoro-1,4-phenylene (*—C$_6$F$_4$—*).

15. The compound of claim 1, wherein L' is 1,4-phenylene (*—C$_6$H$_4$—*).

16. A photo-acid generating polymer (PAG polymer), comprising a non-ionic first repeating unit of formula (11):

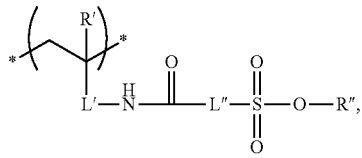

wherein

R' is a monovalent radical selected from the group consisting of H, F, C$_1$-C$_3$ alkyl, fluorine-containing C$_1$-C$_3$ alkyl groups, and cyano, L' and L" are independently divalent radicals comprising 1 to 10 carbons, a carbon of L" is linked to the carbonyl,

*—SO₃—R" represents a sulfonate ester of an N-hydroxy imide, and the first repeating unit is capable of generating an acid upon exposure to radiation.

17. The PAG polymer of claim 16, wherein the PAG polymer is thermally stable in a lithographic process up to at least 130° C.

18. The PAG polymer of claim 16, wherein R" is

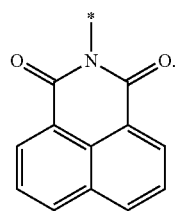 [SMILES: *N1C(=O)c2cccc3cccc(c23)C1=O]

19. The PAG polymer of claim 16, wherein the first repeating unit is selected from the group consisting of:

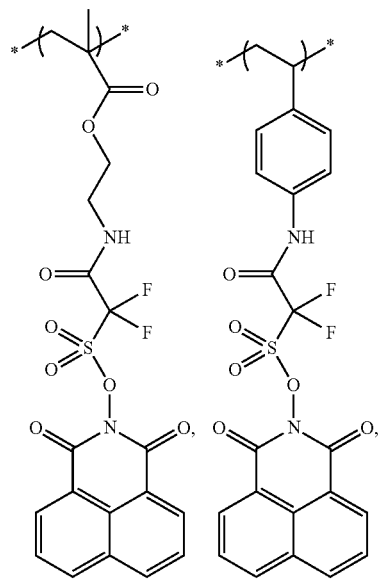

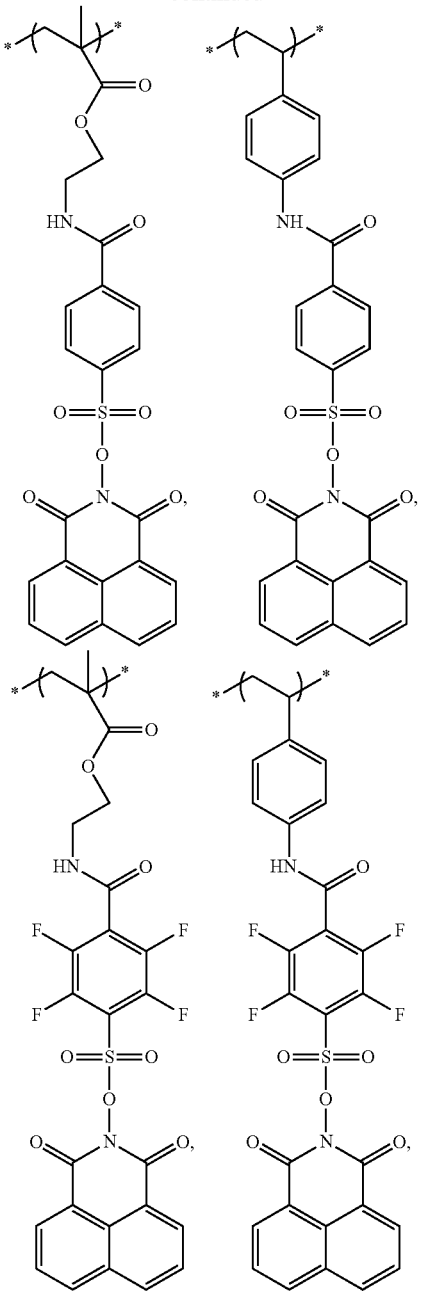

and combinations thereof.

20. The PAG polymer of claim 16, wherein the PAG polymer further comprises a second repeating unit comprising an acid labile group, the acid labile group comprising a protected acid group capable of being deprotected by an acid, and the PAG polymer is capable of chemical amplification in a lithographic process.

21. The PAG polymer of claim 20, wherein the protected acid of the second repeating unit is a carboxylic acid group protected with an acid-labile functionality selected from the group consisting of tertiary esters, acetals, ketals, and orthoesters.

22. The PAG polymer of claim 20, wherein the PAG polymer further comprises an auxiliary repeating unit comprising a moiety selected from the group consisting of fluoroalcohols, fluorosulfonamides, lactones, alcohols, and combinations thereof.

23. The PAG polymer of claim 16, wherein the PAG polymer comprises:
- 1 mol % to 15 mol % of the first repeating unit,
- 10 mol % to 50 mol % of a second repeating unit having a protected acid group capable of being deprotected by an acid, and
- 89 mol % to 35 mol % of an auxiliary repeating unit comprising a moiety selected from the group consisting of fluoroalcohols, fluorosulfonamides, lactones, alcohols and combinations thereof, wherein mol % is based on total moles of monomers of the polymer.

24. A resist composition, comprising:
the PAG polymer of claim 16; and
an organic solvent, wherein the PAG polymer is dissolved in the organic solvent, and the resist composition is suitable for forming a resist patterns in a lithographic process.

25. A method, comprising:
providing a layered structure comprising a resist layer disposed on a surface of a substrate, the resist layer comprising the PAG polymer of claim 16;
pattern-wise exposing the resist layer to radiation, thereby forming an exposed resist layer;
baking the exposed resist layer at about 90° C. to about 130° C. for at least 1 second, thereby forming a treated resist layer; and
selectively removing a region of the treated resist layer using a developer, thereby forming a patterned resist layer.

26. The method of claim 25, wherein the developer is an aqueous alkaline developer that selectively removes an exposed region of the treated resist layer, leaving a positive tone patterned resist layer.

27. The method of claim 25, wherein the developer is an organic solvent developer that selectively removes a non-exposed region of the treated resist layer, leaving a negative tone patterned resist layer.

28. The method of claim 25, wherein the radiation has a wavelength between 0 nm and 300 nm.

29. The method of claim 25, wherein the radiation has a wavelength of about 4 nm to about 124 nm.

30. The method of claim 25, wherein the radiation has a wavelength of 13.5 nm.

31. The method of claim 25, wherein the resist layer is thermally stable up to at least 130° C. prior to said pattern-wise exposing.

32. The PAG polymer of claim 16, wherein L" is difluoromethylene (*—$CF_2$—*).

33. The PAG polymer of claim 16, wherein L" is 1,4-phenylene (*—$C_6H_4$—*).

34. The PAG polymer of claim 16, wherein L" is tetrafluoro-1,4-phenylene (*—$C_6F_4$—*).

35. The PAG polymer of claim 16, wherein L' is 1,4-phenylene (*—$C_6H_4$—*).

36. The PAG polymer of claim 16, wherein L' has a structure according to formula (3):

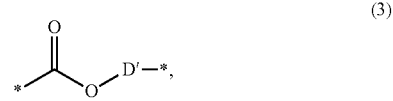

(3)

wherein
the carbonyl carbon is linked to the carbon bearing R' of formula (11),
D' is a divalent radical selected from the group consisting of alkylene groups comprising 2 to 9 carbons, and
D' is linked to the amide nitrogen of formula (11).

37. The PAG polymer of claim 36, wherein D' is 1,2-ethylene (*—$CH_2CH_2$—*).

* * * * *